(12) United States Patent
Schiemann et al.

(10) Patent No.: US 7,816,365 B2
(45) Date of Patent: Oct. 19, 2010

(54) AMINE DERIVATIVES

(75) Inventors: Kai Schiemann, Seeheim-Jugenheim (DE); Guenter Hoelzemann, Seeheim-Jugenheim (DE); Wilfried Rautenberg, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 766 days.

(21) Appl. No.: 10/581,499

(22) PCT Filed: Nov. 5, 2004

(86) PCT No.: PCT/EP2004/012523

§ 371 (c)(1),
(2), (4) Date: Jun. 2, 2006

(87) PCT Pub. No.: WO2005/054246

PCT Pub. Date: Jun. 16, 2005

(65) Prior Publication Data

US 2007/0112006 A1    May 17, 2007

(30) Foreign Application Priority Data

Dec. 4, 2003    (DE) ................. 103 56 579

(51) Int. Cl.
| | | |
|---|---|---|
| C07D 487/04 | (2006.01) | |
| C07D 231/38 | (2006.01) | |
| C07D 249/14 | (2006.01) | |
| C07D 471/14 | (2006.01) | |
| A61K 31/519 | (2006.01) | |
| A61P 35/00 | (2006.01) | |
| A61K 31/53 | (2006.01) | |

(52) U.S. Cl. .................. 514/259.3; 514/259.31; 514/246; 544/256; 544/280; 544/180; 544/194

(58) Field of Classification Search ............... 544/256, 544/280; 514/259.3, 259.31
See application file for complete search history.

(56) References Cited

U.S. PATENT DOCUMENTS

| 4,576,943 A | 3/1986 | Tomcufcik et al. |
| 4,582,833 A | 4/1986 | Tomcufcik et al. |

FOREIGN PATENT DOCUMENTS

| DE | 4008181 A1 * | 9/1991 |
| WO | WO 96/31510 A | 10/1996 |
| WO | WO 98/54093 A | 12/1998 |
| WO | WO 02/50079 A | 6/2002 |
| WO | WO 02/064211 A | 8/2002 |
| WO | WO 02064211 A1 * | 8/2002 |

OTHER PUBLICATIONS

Reiter et al. Journal of Heterocyclic Chemistry (1995), 32(2), 407-17; CA 123:112014, 1995.*
West, Anthony R., Solid State Chemistry and its Applications, Wiley, New York, 1988, pp. 358 & 365.*
Vippagunta et al., Advanced Drug Delivery Reviews 48: 3-26, 2001.*
Reiter, et al: "On Triazoles. XXXV. The Reaction of 5-Amino-1,2,4-Triazoles with Di- and Triketones" Journal of Heterocyclic Chemistry 1995, United States, Bd. 32, Nr. 2, 1992, pp. 407-417, XP002322758; ISSN: 0022-152X.
Okabe, et al.: "Di Alkyl Bi Cyclic Hetero Cycles With a Bridgehead Nitrogen as Purine Analogs Possessing Significant Cardiac Inotropic Activity" Journal of Heterocyclic Chemistry, Bd. 20, Nr. 3, 1983, pp. 735-751, XP002322759; ISSN: 0022-152X.

* cited by examiner

Primary Examiner—Venkataraman Balasubramanian
(74) Attorney, Agent, or Firm—Millen, White, Zelano & Branigan, P.C.

(57) ABSTRACT

Disclosed are compounds of formula (I),

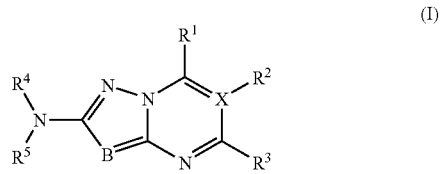

which are inhibitors of tyrosine kinases, in particular TIE-2, and Raf kinases and which can be employed, inter alia, for the treatment of tumours.

47 Claims, No Drawings

AMINE DERIVATIVES

BACKGROUND OF THE INVENTION

The invention had the object of finding novel compounds having valuable properties, in particular those which can be used for the preparation of medicaments.

The present invention relates to compounds and the use of compounds in which the inhibition, regulation and/or modulation of kinase signal transduction, in particular tyrosine kinase and/or serine/threonine kinase signal transduction, plays a role, furthermore to pharmaceutical compositions which comprise these compounds, and to the use of the compounds for the treatment of kinase-induced diseases.

Specifically, the present invention relates to compounds of the formula I which inhibit, regulate and/or modulate tyrosine kinase signal transduction, to compositions which comprise these compounds, and to methods for the use thereof for the treatment of tyrosine kinase-induced diseases and conditions, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic disorders and diseases of the immune system, also auto-immune diseases, cirrhosis, diabetes and diseases of the blood vessels, including instability and permeability, and the like, in mammals.

Tyrosine kinases are a class of enzymes with at least 400 members which catalyse the transfer of the terminal phosphate of adenosine triphosphate (gamma-phosphate) to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important factors in cell proliferation, carcinogenesis and cell differentiation (see reviews by Schlessinger and Ullrich, Neuron 9, 383-391 (1992) and 1-20 (1992)).

Tyrosine kinases can be divided into receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular.

Receptor-type tyrosine kinases consist of a multiplicity of transmembrane receptors with different biological activity. Thus, about 20 different subfamilies of receptor-type tyrosine kinases have been identified. One tyrosine kinase subfamily, known as the HER subfamily, consists of EGFR, HER2, HER3 and HER4. Ligands from this subfamily of receptors include epithelial growth factor, TGF-α, amphiregulin, HB-EGF, betacellulin and heregulin. Another subfamily of these receptor-type tyrosine kinases is the insulin subfamily, which includes INS-R, IGF-IR and IR-R. The PDGF subfamily includes the PDGF-α and -β, receptors, CSFIR, c-kit and FLK-II. In addition, there is the FLK family, which consists of the kinase insert domain receptor (KDR), foetal liver kinase-1 (FLK-1), foetal liver kinase-4 (FLK-4) and fms tyrosine kinase-1 (flt-1). The PDGF and FLK families are usually discussed together due to the similarities between the two groups. For a detailed discussion of receptor-type tyrosine kinases, see the paper by Plowman et al., *DN & P* 7(6):334-339, 1994, which is hereby incorporated by way of reference.

The RTKs (receptor tyrosine kinases) also include TIE2 and its ligands angiopoietin 1 and 2. More and more homologues of these ligands have now been found, the action of which has not yet been demonstrated clearly in detail. TIE1 is known as a homologue of TIE2. The TIE RTKs are expressed selectively on endothelial cells and are involved in processes of angiogenesis and maturing of the blood vessels. They may consequently be a valuable aim, in particular, in diseases of the vascular system and in pathologies in which vessels are utilised or even reformed. In addition to prevention of neovascularisation and maturing, stimulation of neovascularisation may also be a valuable aim for active compounds. Reference is made to review papers on angiogenesis, tumour development and kinase signal transduction by G. Breier Placenta (2000) 21, Suppl A, Trophoblasr Res 14, S11-S15

F. Bussolino et al. TIBS 22, 251-256 (1997)

G. Bergers & L. E. Benjamin Nature Rev Cancer 3, 401-410 (2003)

P. Blume-Jensen & . Hunter Nature 411, 355-365 (2001)

M. Ramsauer & P. D'Amore J. Clin. INvest. 110, 1615-1617 (2002)

S. Tsigkos et al. Expert Opin. Investig. Drugs 12, 933-941 (2003)

Examples of kinase inhibitors which have already been tested in cancer therapy are given in L. K. Shawyer et al. Cancer Cell 1, 117-123 (2002) and D. Fabbro & C. Garcia-Echeverria Current Opin. Drug Discovery & Development 5, 701-712 (2002).

Non-receptor-type tyrosine kinases likewise consist of a multiplicity of subfamilies, including Src, Frk, Btk, Csk, Abl, Zap70, Fes/Fps, Fak, Jak, Ack, and LIMK. Each of these subfamilies is further sub-divided into different receptors. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor-type tyrosine kinases, see the paper by Bolen *Oncogene*, 8:2025-2031 (1993), which is hereby incorporated by way of reference.

Both receptor-type tyrosine kinases and non-receptor-type tyrosine kinases are involved in cellular signalling pathways leading to various pathogenic conditions, including cancer, psoriasis and hyperimmune responses. It has been proposed that various receptor-type tyrosine kinases, and the growth factors binding to them, play a role in angiogenesis, although some may promote angiogenesis indirectly (Mustonen and Alitalo, *J. Cell Biol.* 129:895-898, 1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11-15, 1993). VEGF and KDR are a ligand-receptor pair which plays a vital role in the proliferation of vascular endothelial cells and the formation and sprouting of blood vessels, referred to as vasculogenesis and angiogenesis respectively.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilisation of endothelial cells; (v) reorganisation of mobilised endothelial cells to form functional capillaries; (vi)

capillary loop formation; and (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogenesis is also activated during wound healing and at certain stages of the female reproductive cycle. Inappropriate or pathological angiogenesis has been associated with several conditions, including various retinopathies; ischemic disease; atherosclerosis; chronic inflammatory disorders; rheumatoid arthritis, and cancer. The role of angiogenesis in conditions is discussed, for instance, in Fan et al, Trends in Pharmacol Sci. 16:54 66; Shawver et al, DOT Vol. 2, No. 2 February 1997; Folkmann, 1995, Nature Medicine 1:27-31.

In cancer, the growth of solid tumors has been shown to be angiogenesis-dependent. (see Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Angiogenesis is characterised by excessive activity of vascular endothelial growth factor (VEGF). VEGF actually consists of a family of ligands (Klagsburn and D'Amore, *Cytokine & Growth Factor Reviews* 7:259-270, 1996). VEGF binds the high affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be susceptible to the antiangiogenic effect of VEGF receptor antagonists (Kim et al., Nature 362, pp. 841-844, 1993).

Three PTK (protein tyrosinkinase) receptors for VEGFR have been identified: VEGFR-1 (Flt-1); VEGRF-2 (Flk-1 or KDR) and VEGFR-3 (Flt-4). VEGFR-2 is of particular interest.

Solid tumours can therefore be treated with tyrosine kinase inhibitors since these tumours depend on angiogenesis for the formation of the blood vessels that are necessary to support their growth. These solid tumours include monocytic leukaemia, brain, urogenital tract, lymphatic system, stomach, laryngeal and lung carcinoma, including lung adenocarcinoma and small cell lung carcinoma. Further examples include carcinomas in which overexpression or activation of Raf-activating oncogenes (for example K-ras, erb-B) is observed. These carcinomas include pancreatic and breast carcinoma. Inhibitors of these tyrosine kinases are therefore suitable for the prevention and treatment of proliferative diseases caused by these enzymes.

The angiogenic activity of VEGF is not limited to tumours. VEGF accounts for the angiogenic activity produced in or near the retina in diabetic retinopathy. This vascular growth in the retina leads to visual degeneration culminating in blindness. Ocular VEGF mRNA and protein levels are elevated by conditions such as retinal vein occlusion in primates and decreased $PO_2$ level in mice that lead to neovascularisation. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

Expression of VEGF is also significantly increased in hypoxic regions of animal and human tumours adjacent to areas of necrosis. In addition, VEGF is upregulated by the expression of the oncogenes Ras, Raf, Src and mutant p53 (all of which are important in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activities. These monoclonal antibodies also inhibit the growth of typically less well vascularised human colon carcinomas in athymic mice and decrease the number of tumours arising from inoculated cells.

The expression of a VEGF-binding construct of Flk-1, Flt-1, the mouse KDR receptor homologue truncated to eliminate the cytoplasmic tyrosine kinase domains but retaining a membrane anchor, in viruses virtually stops the growth of a transplantable glioblastoma in mice, presumably by the dominant negative mechanism of heterodimer formation with membrane-spanning endothelial cell VEGF receptors. Embryonic stem cells, which normally grow as solid tumours in nude mice, do not produce detectable tumours if both VEGF alleles are knocked out. Taken together, these data indicate the role of VEGF in the growth of solid tumours. Inhibition of KDR or Flt-1 is involved in pathological angiogenesis, and these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp. 1-8, 1991).

Angiopoietin 1 (Ang1), a ligand for the endothelium-specific receptor-type tyrosine kinase TIE-2, is a novel angiogenic factor (Davis et al, Cell, 1996, 87:1161-1169; Partanen et al, Mol. Cell Biol., 12:1698-1707 (1992); U.S. Pat. Nos. 5,521,073; 5,879,672; 5,877,020; and 6,030,831). The acronym TIE stands for "tyrosine kinase with Ig and EGF homology domains". TIE is used for the identification of a class of receptor-type tyrosine kinases which are expressed exclusively in vascular endothelial cells and early haemopoietic cells. TIE receptor kinases are typically characterised by the presence of an EGF-like domain and an immunoglobulin (Ig)-like domain which consists of extracellular fold units stabilised by disulfide bridge bonds between the chains (Partanen et al Curr. Topics Microbiol. Immunol., 1999, 237:159-172). In contrast to VEGF, which exerts its function during the early stages of vascular development, Ang1 and its receptor TIE-2 act during the later stages of vascular development, i.e. during vascular transformation (transformation relates to the formation of a vascular lumen) and maturing (Yancopoulos et al, Cell, 1998, 93:661-664; Peters, K. G., Circ. Res., 1998, 83(3):342-3; Suri et al, Cell 87, 1171-1180 (1996)).

Accordingly, it would be expected that inhibition of TIE-2 should interrupt the transformation and maturing of a new vascular system initiated by angiogenesis and should thus interrupt the angiogenesis process. Furthermore, inhibition at the kinase domain binding site of VEGFR-2 would block phosphorylation of tyrosine residues and serve to interrupt initiation of angiogenesis. It must therefore be assumed that inhibition of TIE-2 and/or VEGFR-2 should prevent tumour angiogenesis and serve to slow or completely eliminate tumour growth.

Accordingly, treatment of cancer and other diseases associated with inappropriate angiogenesis could be provided.

As discussed herein, the signalling pathways described are relevant for various diseases. Accordingly, the compounds according to the invention are useful in the prophylaxis and/or treatment of diseases that are dependent on the said signalling pathways through interaction with one or more of the said signalling pathways.

The present invention is directed to methods for the regulation, modulation or inhibition of TIE-2 for the prevention and/or treatment of diseases in connection with unregulated or disturbed TIE-2 activity. In particular, the compounds of the formula I can also be employed in the treatment of certain forms of cancer. Furthermore, the compounds of the formula I can be used to provide additive or synergistic effects in certain existing cancer chemotherapies and/or can be used to restore the efficacy of certain existing cancer chemotherapies and radiotherapies.

The compounds of the formula I can furthermore be used for the isolation and investigation of the activity or expression of TIE-2. In addition, they are particularly suitable for use in diagnostic methods for diseases associated with irregular or disturbed TIE-2 activity.

The present invention is furthermore directed to methods for the regulation, modulation or inhibition of VEGFR-2 for the prevention and/or treatment of diseases associated with irregular or disturbed VEGFR-2 activity.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of conditions and/or diseases are attributable to either aberrant activation or functional mutations in the molecular components of kinase cascades. Consequently, considerable attention has been devoted to the characterisation of these proteins and compounds that are able to modulate their activity (review article see: Weinstmono-Oppenheimer et al. Pharma. &. Therap., 2000, 88, 229-279).

The protein kinase PKB (also known as AKT and RAC-PK) is a member of the AKT/PKB family of serine/threonine kinases and has been shown to be involved in a diverse set of signalling pathways in human malignancy (Nicholson et al., Cell. Signal., 2002, 14, 381-395). PKB, like other members of the AKT/PKB family, is located in the cytosol of unstimulated cells and translocates to the cell membrane following stimulation. PKB translocation can be activated by a number of ligands, including platelet derived growth factor, epidermal growth factor, basic fibroblast growth factor, cellular stress, such as, for example, heat shock and hyperosmolarity, as well as insulin (Bos, Trends Biochem. Sci., 1995, 20, 441-442), and other studies have shown that this activation is through PI3 kinase which is wortmannin sensitive (Franke et al., Science, 1997, 275, 665-668). Once localised to the plasma membrane, PKB has been shown to mediate several functions within the cell, including apoptosis, the metabolic effects of insulin, induction of differentiation and/or proliferation, protein synthesis and stress responses (Alessi and Cohen, Curr. Opin. Genet. Dev., 1998, 8, 55-62; Downward, Curr. Opin. Cell Biol., 1998, 10, 262-267).

PKB was cloned independently in 1991 by three groups (Bellacosa et al., Science, 1991, 254, 274-277; Coffer and Woodgett, Eur. J. Biochem., 1991, 201, 475-481; Jones et al., Cell Regul., 1991, 2, 1001-1009), but its association with primary human gastric carcinoma was recognised as early as 1987 (Staal et al., Proc. Natl. Acad. Sci. USA, 1987, 84, 5034-5037). Sequencing of PKBα revealed homology within the kinase domains to the PKA (about 68%) and PKC isozymes (about 73%) (Jones et al., Proc. Natl. Acad. Sci. U.S.A., 1991, 88, 4171-5), a fact that lead to its renaming as PKB. There are three cellular isoforms of PKB and two splice variants (PKBα, β, γ, $β_1$, $γ_1$; Brazil et al. Trends in Bio Sci, 2001, 26, 657-663). PKBα was found to be amplified or overexpressed in gastric adenocarcinomas and in a breast cancer cell line (Staal et al., Proc. Natl. Acad. Sci. U.S.A., 1987, 84, 5034-7; Jones et al., Cell Regul., 1991, 2, 1001-9). PKBβ is amplified or overexpressed in 3% of breast (Bellacosa et al., Int. J. Cancer, 1995 64, 280-5), 12% of pancreatic (Cheng et al., Proc. Natl. Acad. Sci. U.S.A., 1996, 93, 3636-41) and 15% of ovarian cancers (Bellacosa et al., Int. J. Cancer, 1995, 64, 280-5; Cheng et al., Proc. Natl. Acad. Sci. U.S.A., 1992, 89, 9267-71).

PKBγ is overexpressed in oestrogen receptor-deficient breast cancer and in androgen-independent prostate cell lines (Nakatani et al., J. Biol. Chem. 1999, 274, 21528-32).

It has been proposed that PKB is a gene which is involved in chromosomal rearrangement at chromosome band 14q32. This locus is known to undergo rearrangement in human T-cell malignancies, such as, for example, prolymphocytic leukaemias and mixed lineage childhood leukaemias (Staal et al., Genomics, 1988, 2, 96-98).

PKB also plays a role in the prevention of "programmed cell death" or apoptosis by inhibitory phosphorylation of ASK-1, Bad, Caspase9 and FKHR (for review see Nicholson et al., Cell Signalling 2001, 14, 281-395). It has been shown that PKB provides a survival signal (for review see Lawlor et al., J. of Cell Science 2001, 114, 2903-2910) to cells in order to protect them from a number of agents, including UV radiation (Dudek et al., Science, 1997, 275, 661-665), withdrawal of IGF1 from neuronal cells, detachment from the extracellular matrix, stress and heat shock (Alessi and Cohen, Curr. Opin. Genet. Dev., 1998, 8, 55-62).

The dual-specific phosphatase PTEN (phosphatase and tensin homologue deleted on chromosome ten) increases the Ptdlns(3, 4, 5)$P_3$ level in the cell by dephosphorylation of Ptdlns(3, 4, 5)$P_3$. Ptdlns(3, 4, 5)$P_3$ binds to the PH domain (Pleckstrin homology domain) of PKB. This binding is an essential step for membrane translocation and activation of PKB. PTEN is a tumour suppressor gene mutated in a large proportion of glioblastoma and melanoma cell lines, advanced prostate carcinomas and endometrial carcinomas. Furthermore, it is deleted in >80% of patients with hereditary conditions, such as, for example, Cowden's disease, Lhermitte-Duclose disease and Bannayan-Zonana Syndrome. The patients display a number of similar features, including multiple benign tumours (harmatomas) and increased susceptibility to breast and thyroid malignancies (Di Cristofano et al. Cell, 2000, 100, 387-390).

Cell lines derived from PTEN$^{+/-}$ heterozygous mice (PTEN$^{-/-}$ heterozygous mice are not viable) show increased PtdIns(3, 4, 5)P$_3$ levels paralleled by increased PKB activity, with concomitant decreased sensitivity to apoptosis (Di Christofano et al. Nat. Genet. 1998, 19, 348-355; Stambolic et al., Cell, 1998, 95, 29-39, Myers et al., Proc. Natl. Acad. Si. U.S.A., 1998, 96 13513-13518).

PKB is also able to promote cell cycle progression by inhibiting p21 cell cycle inhibitor (Zhou et al.; Nat. Cell Biol., 2002, 3, 245-252).

These findings may explain the overexpression of PKB observed in cancer cells which allows preferential survival and proliferation of the carcinomas by avoiding the normal progression to apoptosis.

At present, there are no known therapeutic agents which effectively inhibit the activity of PKB. Consequently, there remains a long felt need for additional agents which are capable of effectively inhibiting PKB function for the activation of pro-apoptotic proteins in all kinds of cancer as chemotherapeutic agents.

The synthesis of small compounds which specifically inhibit, regulate and/or modulate tyrosine kinase signal transduction is therefore desirable and an aim of the present invention.

It has been found that the compounds according to the invention and salts thereof have very valuable pharmacological properties while being well tolerated.

Surprisingly, it has been found that the compounds according to the invention are able to interact with signalling pathways, especially the signalling pathways described herein. The compounds according to the invention preferably exhibit an advantageous biological activity which can easily be demonstrated in enzyme-based assays, for example assays as described herein. In such enzyme-based assays, the compounds according to the invention preferably exhibit and cause an inhibiting effect, which is usually documented by IC$_{50}$ values in a suitable range, preferably in the micromolar range and more preferably in the nanomolar range.

As discussed herein, these signalling pathways are relevant for various diseases. Accordingly, the compounds according to the invention are suitable for the prophylaxis and/or treatment of diseases that are dependent on the said signalling pathways by interacting with one or more of the said signalling pathways.

The present invention therefore relates to compounds according to the invention as promoters or inhibitors.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

In a comparative measurement, it has furthermore been found that the compounds of the formula I act as PKB inhibitors. This action can be demonstrated, for example, by a method described by Alessi et al. EMBO L. 1996, 15, 6541-6551.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein are described in the literature (for example Campos-González, R. and Glenney, Jr., J. R. 1992, J. Biol. Chem. 267, page 14535).

For the identification of kinase inhibitors, various assay systems are available. In the scintillation proximity assay (Sorg et al., J. of. Biomolecular Screening, 2002, 7, 11-19) and the flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

There are many diseases associated with deregulation of cell proliferation and cell death (apoptosis). The conditions of interest include, but are not limited to, the following. The compounds according to the invention are suitable for the treatment of a variety of conditions where there is proliferation and/or migration of smooth muscle cells and/or inflammatory cells into the intimal layer of a vessel, resulting in restricted blood flow through that vessel, for example in the case of neointimal occlusive lesions. Occlusive transplant vascular diseases of interest include atherosclerosis, coronary vascular disease after transplantation, vein graft stenosis, peri-anastomotic prosthetic restenosis, restenosis after angioplasty or stent placement, and the like.

The compounds according to the invention are also suitable as p38 kinase inhibitors.

Heteroarylureas which inhibit p38 kinase are described in WO 02/85859.

PRIOR ART

Triazolo[1,5-a]pyrimidin-2-ylamine derivatives are described as thrombin inhibitors in WO 02/064211.

SUMMARY OF THE INVENTION

The invention relates to compounds of the formula I

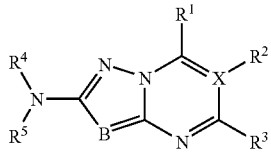

I in which
X denotes C or N,
B denotes N, CH or C—CN,
$R^1$ denotes H, A, OH, $NH_2$, —$(CH_2)_m$—Ar or —$(CH_2)_m$-$Het^2$,
$R^2$ if X=N is absent or
   if X=C denotes H, A, Hal, CN, —$(CH_2)_p$—Ar, —$(CH_2)_p$—COOH, —$(CH_2)_p$—COOS, —$(CH_2)_p$-$Het^3$, —$(CH_2)_p$—$NH_2$, $SO_2A$, CHO or COA,
$R^3$ denotes H, A, —S—A, —$(CH_2)_p$—Ar, —$(CH_2)_p$-Het, NH—$(CH_2)_p$—Ar, NH—$(CH_2)_p$-Het, $NH_2$, NHA, $NA_2$, NH-alkylene-$NH_2$, NH-alkylene-NHA, NH-alkylene-$NA_2$ or NA-alkylene-$NA_2$,
$R^4$ denotes —$(CH_2)_s$—$(Ar^1)_n$—Y—$R^6$,
$R^5$ denotes H or $CH_3$,
$R^4$ and $R^5$ together also denote

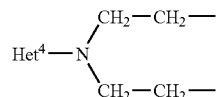

$R^6$ denotes $Het^4$, —$(CH_2)_r$—$NH_2$, —$(CH_2)_r$—NHA or —$(CH_2)_r$—$NA_2$,
Y denotes O, S, $(CH_2)_q$ or NH,
Ar denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH,
$Ar^1$ denotes phenylene or piperazinediyl,
Het denotes a mono- or bicyclic saturated, unsaturated or aromatic heterocycle having 1 to 4 N, O and/or S atoms, which may be unsubstituted or mono-, di- or trisubstituted by Hal, A, NHA, $NA_2$, OA, COOA, CN, —$(CH_2)_p$—Ar, —$(CH_2)_t$—OH, —$(CH_2)_p$-$Het^1$ or carbonyl oxygen (=O),
$Het^1$ denotes a mono- or bicyclic saturated, unsaturated or aromatic heterocycle having 1 to 4 N, O and/or S atoms, which may be unsubstituted or mono- or disubstituted by A or carbonyl oxygen (=O),
$Het^2$ denotes a monocyclic aromatic heterocycle having 1 to 3 N, O and/or S atoms, which may be unsubstituted or mono- or disubstituted by A,
$Het^3$ denotes a monocyclic saturated or aromatic heterocycle having 1 to 3 N, O and/or S atoms, which may be unsubstituted or mono- or disubstituted by A,
$Het^4$ denotes a mono- or bicyclic saturated, unsaturated or aromatic heterocycle having 1 to 4 N, O and/or S atoms, which may be unsubstituted or mono-, di- or trisubstituted by Hal, A, $CONH_2$, CONHA, $CONA_2$ or $Ar^2$,
$Ar^2$ denotes phenyl which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$ or $SO_2A$,
$R^7$, $R^8$, $R^9$, $R^{10}$ each, independently of one another, denote H, A or —$(CH_2)_p$—Ar,
A denotes alkyl having 1 to 10 C atoms, where, in addition, 1-7 H atoms may be replaced by F and/or chlorine,
m denotes 0, 1, 2, 3 or 4,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
Hal denotes F, Cl, Br or I,
and, if X=C,
   $R^1$ and $R^2$ together may also denote —$(CH_2)_4$— or
   $R^2$ and $R^3$ together may also denote —$(CHR^7$—$NR^8$—$CHR^9$—$CHR^{10})$—,
and, if $Ar^1$ denotes piperazinediyl, $R^6$ may also denote H or alkyl having 1-6 C atoms, and pharmaceutically usable derivatives, solvates, tautomers, salts and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to aspects 1-33 as provided below and pharmaceutically usable derivatives, salts, solvates and stereoisomers thereof, in aspect 1, to compounds of the formula I

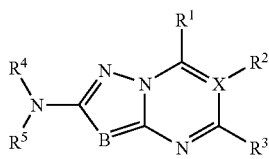

in which
X denotes C or N,
B denotes N, CH or C—CN,
$R^1$ denotes H, A, OH, $NH_2$, —$(CH_2)_m$—Ar or —$(CH_2)_m$—$Het^2$,
$R^2$ if X=N is absent or if X=C denotes H, A, Hal, CN, —$(CH_2)_p$—Ar, —$(CH_2)_p$—COOH, —$(CH_2)_p$—COOA, —$(CH_2)_p$—$Het^3$, —$(CH_2)_p$—$NH_2$, $SO_2A$, CHO or COA,
$R^3$ denotes H, A, —S—A, —$(CH_2)_p$—Ar, —$(CH_2)_p$—Het, NH—$(CH_2)_p$—Ar, NH—$(CH_2)_p$—Het, $NH_2$, NHA, $NA_2$, NH-alkylene-$NH_2$, NH-alkylene-NHA, NH-alkylene-$NA_2$ or NA-alkylene-$NA_2$,
$R^4$ denotes —$(CH_2)_s$—$(Ar^1)_n$—Y—$R^6$,
$R^5$ denotes H or $CH_3$,
$R^4$ and $R^5$ together also denote

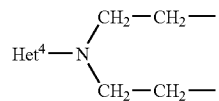

$R^6$ denotes $Het^4$, —$(CH_2)_r$—$NH_2$, —$(CH_2)_r$—NHA or —$(CH_2)_r$—$NA_2$,
Y denotes O, S, $(CH_2)_q$ or NH,
Ar denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH,
$Ar^1$ denotes phenylene or piperazinediyl,
Het denotes a mono- or bicyclic saturated, unsaturated or aromatic heterocycle having 1 to 4 N, O and/or S atoms, which may be unsubstituted or mono-, di- or trisubstituted by Hal, A, NHA, $NA_2$, OA, COOA, CN, —$(CH_2)_p$—Ar, —$(CH_2)_t$—OH, —$(CH_2)_p$—$Het^1$ or carbonyl oxygen (=O),
$Het^1$ denotes a mono- or bicyclic saturated, unsaturated or aromatic heterocycle having 1 to 4 N, O and/or S atoms, which may be unsubstituted or mono- or disubstituted by A or carbonyl oxygen (=O),
$Het^2$ denotes a monocyclic aromatic heterocycle having 1 to 3 N, O and/or S atoms, which may be unsubstituted or mono- or disubstituted by A,
$Het^3$ denotes a monocyclic saturated or aromatic heterocycle having 1 to 3 N, O and/or S atoms, which may be unsubstituted or mono- or disubstituted by A,
$Het^4$ denotes a mono- or bicyclic saturated, unsaturated or aromatic heterocycle having 1 to 4 N, O and/or S atoms, which may be unsubstituted or mono-, di- or trisubstituted by Hal, A, $CONH_2$, CONHA, $CONA_2$ or $Ar^2$,
$Ar^2$ denotes phenyl which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$ or $SO_2A$,
$R^7, R^8, R^9, R^{10}$ each, independently of one another, denote H, A or —$(CH_2)_p$—Ar,
A denotes alkyl having 1 to 10 C atoms, where, in addition, 1-7 H atoms may be replaced by F and/or chlorine,
m denotes 0, 1, 2, 3 or 4,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
Hal denotes F, Cl, Br or I,
and, if X=C,
$R^1$ and $R^2$ together may also denote —$(CH_2)_4$— or
$R^2$ and $R^3$ together may also denote —$(CHR^7$—$CHR^8$—$NR^9$—$CHR^{10})$—,
and, if $Ar^1$ denotes piperazinediyl, $R^6$ may also denote H or alkyl having 1-6 C atoms,
and pharmaceutically usable derivatives, solvates, tautomers, salts and stereoisomers thereof, including mixtures thereof in all ratios;

in aspect 2, to compounds according to aspect 1 in which
$R^1$ denotes A, OH, $NH_2$, —$(CH_2)_m$—Ar or —$(CH_2)_m$—$Het^2$,
Ar denotes phenyl which is unsubstituted or mono-, di- or trisubstituted by Hal, A, OA, COOH or COOA,
m denotes 0,
and pharmaceutically usable derivatives, solvates, tautomers, salts and stereoisomers thereof, including mixtures thereof in all ratios;

in aspect 3, to compounds according to aspect 1 or 2 in which
$R^4$ denotes —$(CH_2)_s$—$(Ar^1)_n$—Y—$R^6$,
s denotes 0 or 1,
n denotes 1, Ar¹ denotes phenylene,
R⁶ denotes Het⁴,
Y denotes O,
Het⁴ denotes pyridyl which is unsubstituted or monosubstituted by CONHA,
or benzo-1,2,5-thiadiazol-5-yl,
and pharmaceutically usable derivatives, solvates, tautomers, salts and stereoisomers thereof, including mixtures thereof in all ratios;

in aspect 4, to compounds according to aspects 1-3 in which
R⁴ denotes —(CH$_2$)$_s$—(Ar¹)$_n$—Y—R⁶,
s denotes 1,
n denotes 0,
Y denotes (CH$_2$)$_q$,
q denotes 0,
R⁶ denotes Het⁴,
Het⁴ denotes pyridyl, benzo-1,2,5-thiadiazol-5-yl, thiazole, 1,2,3-triazole, thienyl or furyl, each of which is unsubstituted or monosubstituted by CONHA, A and/or Ar²,
Ar² denotes phenyl which is unsubstituted or mono-, di- or trisubstituted by A,
and pharmaceutically usable derivatives, solvates, tautomers, salts and stereoisomers thereof, including mixtures thereof in all ratios;

in aspect 5, to compounds according to aspects 1-4 in which
R⁴ denotes —(CH$_2$)$_s$—(Ar¹)$_n$—Y—R⁶,
s denotes 0,
n denotes 0,
Y denotes (CH$_2$)$_q$,
q denotes 0,
R⁶ denotes —(CH$_2$)$_r$—NH$_2$, —(CH$_2$)$_r$—NHA or —(CH$_2$)$_r$—NA$_2$,
r denotes 1, 2, 3 or 4,
and pharmaceutically usable derivatives, solvates, tautomers, salts and stereoisomers thereof, including mixtures thereof in all ratios;

in aspect 6, to compounds according to aspects 1-5 in which
R⁴ denotes —(CH$_2$)$_s$—(Ar¹)$_n$—Y—R⁶,
s denotes 0,
n denotes 1,
Ar¹ denotes phenylene,
Y denotes O, (CH$_2$)$_q$ or NH,
R⁶ denotes —(CH$_2$)$_r$—NH$_2$, —(CH$_2$)$_r$—NHA or —(CH$_2$)$_r$—NA$_2$,
q denotes 0, 1, 2, 3 or 4,
r denotes 0, 1, 2, 3 or 4,
and pharmaceutically usable derivatives, solvates, tautomers, salts and stereoisomers thereof, including mixtures thereof in all ratios;

in aspect 7, to compounds according to aspects 1-6 in which
R⁴ denotes —(CH$_2$)$_s$—(Ar¹)$_n$—Y—R⁶,
s denotes 1, 2, 3 or 4,
n denotes 0,
Y denotes (CH$_2$)$_q$,
q denotes 0,
R⁶ denotes Het⁴,
Het⁴ denotes a monocyclic saturated heterocycle having 1 to 2 N and/or O atoms, which may be unsubstituted or mono- or disubstituted by A,
and pharmaceutically usable derivatives, solvates, tautomers, salts and stereoisomers thereof, including mixtures thereof in all ratios;

in aspect 8, to compounds according to aspects 1-7 in which
R¹ denotes A, OH, NH$_2$, —(CH$_2$)$_m$—Ar,
m denotes 0,
Ar denotes phenyl which is unsubstituted or mono-, di- or trisubstituted by Hal, A, OA, COOH or COOA,
R² if X=N is absent or
if X=C denotes CN,
R³ denotes H, A, —S—A, phenyl or —(CH$_2$)$_p$—Het,
and pharmaceutically usable derivatives, solvates, tautomers, salts and stereoisomers thereof, including mixtures thereof in all ratios;

in aspect 9, to compounds according to aspects 1-8 in which
R¹ denotes A, OH, NH$_2$, —(CH$_2$)$_m$—Ar,
m denotes 0,
Ar denotes phenyl which is unsubstituted or mono-, di- or trisubstituted by Hal, A, OA, COOH or COOA,
R² if X=N is absent or
if X=C denotes CN,
R³ denotes H, A, —S—A, phenyl or —(CH$_2$)$_p$—Het,
R⁴ denotes —(CH$_2$)$_s$—(Ar¹)$_n$—Y—R⁶,
s denotes 0,
n denotes 0,
Y denotes (CH$_2$)$_q$,
q denotes 0,
R⁶ denotes —(CH$_2$)$_r$—NH$_2$, —(CH$_2$)$_r$—NHA or —(CH$_2$)$_r$—NA$_2$,
r denotes 1, 2, 3 or 4,
and pharmaceutically usable derivatives, solvates, tautomers, salts and stereoisomers thereof, including mixtures thereof in all ratios;

in aspect 10, to compounds according to aspects 1-9 in which
R⁴ denotes —(CH$_2$)$_s$—(Ar¹)$_n$—Y—R⁶,
s denotes 0,
n denotes 1,
Y denotes (CH$_2$)$_q$,
q denotes 0,
R⁶ denotes —(CH$_2$)$_r$—NH$_2$, —(CH$_2$)$_r$—NHA or —(CH$_2$)$_r$—NA$_2$,
r denotes 0,
and pharmaceutically usable derivatives, solvates, tautomers, salts and stereoisomers thereof, including mixtures thereof in all ratios;

in aspect 11, to compounds according to aspects 1-10 in which
R⁴ denotes —(CH$_2$)$_s$—(Ar¹)$_n$—Y—R⁶,
s denotes 0,
n denotes 0 or 1,
Y denotes (CH$_2$)$_q$,
q denotes 0,
R⁶ denotes —(CH$_2$)$_r$—NH$_2$, —(CH$_2$)$_r$—NHA or —(CH$_2$)$_r$—NA$_2$,
r denotes 0, 1, 2, 3 or 4,
and pharmaceutically usable derivatives, solvates, tautomers, salts and stereoisomers thereof, including mixtures thereof in all ratios;

in aspect 12, to compounds according to aspects 1-11 in which
R⁴ denotes —(CH$_2$)$_s$—(Ar¹)$_n$—Y—R⁶,
s denotes 0,
n denotes 0 or 1,
Y denotes (CH$_2$)$_q$,
R⁶ denotes —(CH$_2$)$_r$—NH$_2$, —(CH$_2$)$_r$—NHA or —(CH$_2$)$_r$—NA$_2$,
Ar¹ denotes phenylene,
Y denotes O, (CH$_2$)$_q$ or NH, q denotes 0, 1, 2, 3 or 4,
r denotes 0, 1, 2, 3 or 4,
and pharmaceutically usable derivatives, solvates, tautomers, salts and stereoisomers thereof, including mixtures thereof in all ratios;

in aspect 13, to compounds according to aspects 1-12 in which
$R^1$ denotes A, OH, $NH_2$, —$(CH_2)_m$—Ar,
m denotes 0,
Ar denotes phenyl which is unsubstituted or mono-, di- or trisubstituted by Hal, A, OA, COOH or COOA,
$R^2$ if X=N is absent or
if X=C denotes CN,
$R^3$ denotes H, A, —S—A, phenyl or —$(CH_2)_p$—Het,
$R^4$ denotes —$(CH_2)_s$—$(Ar^1)_n$—Y—$R^6$,
s denotes 0,
n denotes 0 or 1,
Y denotes $(CH_2)_q$,
$R^6$ denotes —$(CH_2)_r$—$NH_2$, —$(CH_2)_r$—NHA or —$(CH_2)_r$—$NA_2$,
$Ar^1$ denotes phenylene,
Y denotes O, $(CH_2)_q$ or NH,
q denotes 0, 1, 2, 3 or 4,
r denotes 0, 1, 2, 3 or 4,
and pharmaceutically usable derivatives, solvates, tautomers, salts and stereoisomers thereof, including mixtures thereof in all ratios;

in aspect 14, to compounds according to aspects 1-13 in which
$R^1$ denotes A, OH, $NH_2$, —$(CH_2)_m$—Ar,
m denotes 0,
Ar denotes phenyl which is unsubstituted or mono-, di- or trisubstituted by Hal, A, OA, COOH or COOA,
$R^2$ if X=N is absent or
if X=C denotes CN,
$R^3$ denotes H, A, —S—A, phenyl or —$(CH_2)_p$—Het,
$R^4$ denotes —$(CH_2)_s$—$(Ar^1)_n$—Y—$R^6$,
s denotes 0,
n denotes 1,
$Ar^1$ denotes phenylene,
$R^6$ denotes $Het^4$,
Y denotes O,
$Het^4$ denotes pyridyl which is unsubstituted or monosubstituted by CONHA,
or benzo-1,2,5-thiadiazol-5-yl,
and pharmaceutically usable derivatives, solvates, tautomers, salts and stereoisomers thereof, including mixtures thereof in all ratios;

in aspect 15, to compounds according to aspects 1-14 in which
$R^4$ denotes —$(CH_2)_2$—$(Ar^1)_n$—Y—$R^6$,
s denotes 0 or 1,
n denotes 0 or 1,
Y denotes O or $(CH_2)_q$,
q denotes 0,
$R^6$ denotes $Het^4$,
$Het^4$ denotes pyridyl, benzo-1,2,5-thiadiazol-5-yl, thiazole, 1,2,3-triazole, thienyl or furyl, each of which is unsubstituted or monosubstituted by CONHA, A and/or $Ar^2$,
$Ar^2$ denotes phenyl which is unsubstituted or mono-, di- or trisubstituted by A,
$A^1$ denotes phenylene,
and pharmaceutically usable derivatives, solvates, tautomers, salts and stereoisomers thereof, including mixtures thereof in all ratios;

in aspect 16, to compounds according to aspects 1-15 in which
Het denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_r$—OH or —$(CH_2)_p$—$Het^1$,
$Het^1$ denotes an unsubstituted monocyclic saturated or aromatic heterocycle having 1 to 3 N and/or O atoms, or

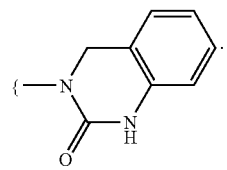

and pharmaceutically usable derivatives, solvates, tautomers, salts and stereoisomers thereof, including mixtures thereof in all ratios;

in aspect 17, to compounds according to aspects 1-16 in which
Het denotes piperazinyl, piperidinyl, morpholinyl, pyrrolidinyl, pyridyl or furyl, which are unsubstituted or may be mono-, di- or trisubstituted by Hal, A, NHA, $NA_2$, COOA, benzyl, —$(CH_2)_r$—OH or —$(CH_2)_p$—$Het^1$,
$Het^1$ denotes morpholinyl, pyrrolidinyl, pyridyl or

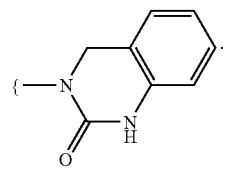

and pharmaceutically usable derivatives, solvates, tautomers, salts and stereoisomers thereof, including mixtures thereof in all ratios;

in aspect 18, to compounds according to aspects 1-17 in which
$R^4$ denotes —$(CH_2)_s$—$(Ar^1)_n$—Y—$R^6$,
s denotes 0 or 1,
n denotes 0 or 1,
Y denotes O, $(CH_2)_q$ or NH,
$Ar^1$ denotes phenylene,
q denotes 0, 1, 2, 3 or 4,
$R^6$ denotes $Het^4$, —$(CH_2)_r$—$NH_2$, —$(CH_2)_4$—NHA or —$(CH_2)_r$—$NA_2$,
r denotes 0, 1, 2, 3 or 4,
$Het^4$ denotes pyridyl, benzo-1,2,5-thiadiazol-5-yl, thiazole, 1,2,3-triazole, thienyl or furyl, each of which is unsubstituted or monosubstituted by CONHA, A and/or $Ar^2$,
$Ar^2$ denotes phenyl which is unsubstituted or mono-, di- or trisubstituted by A,
and pharmaceutically usable derivatives, solvates, tautomers, salts and stereoisomers thereof, including mixtures thereof in all ratios;

in aspect 19, to compounds according to aspects 1-18 in which
$R^1$ denotes A, OH, $NH_2$, —$(CH_2)_m$—Ar,
m denotes 0, Ar denotes phenyl which is unsubstituted or mono-, di- or trisubstituted by Hal, A, OA, COOH or COOA,
$R^2$ if X=N is absent or
if X=C
denotes CN,
$R^3$ denotes H, A, —S—A, phenyl or —$(CH_2)_p$—Het,
Het denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_t$—OH or —$(CH_2)_p$—$Het^1$,
$Het^1$ denotes an unsubstituted monocyclic saturated or aromatic heterocycle having 1 to 2 N and/or O atoms, or

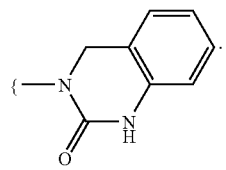

and pharmaceutically usable derivatives, solvates, tautomers, salts and stereoisomers thereof, including mixtures thereof in all ratios;

in aspect 20, to compounds according to aspects 1-19 in which
$R^4$ denotes —$(CH_2)_s$—$(Ar^1)_n$—Y—$R^6$,
s denotes 0, 1, 2, 3 or 4,
n denotes 0 or 1,
Y denotes O or $(CH_2)_q$,
$Ar^1$ denotes phenylene,
q denotes 0,
$R^6$ denotes $Het^4$, —$(CH_2)_r$—$NH_2$, —$(CH_2)_r$—NHA or —$(CH_2)_r$—$NA_2$,
r denotes 0, 1, 2, 3 or 4,
$Het^4$ denotes a monocyclic saturated or aromatic heterocycle having 1 to 3 N, O and/or S atoms, which may be unsubstituted or mono-, di- or trisubstituted by A, $CONH_2$, CONHA, $CONA_2$ or $Ar^2$,
$Ar^2$ denotes phenyl which is unsubstituted or mono-, di- or trisubstituted by A,
and pharmaceutically usable derivatives, solvates, tautomers, salts and stereoisomers thereof, including mixtures thereof in all ratios;

in aspect 21, to compounds according to aspects 1-20 in which
$Het^4$ denotes pyridyl, benzo-1,2,5-thiadiazol-5-yl, piperazine, thiazole or imidazole, each of which is unsubstituted or monosubstituted by CONHA, A and/or $Ar^2$,
and pharmaceutically usable derivatives, solvates, tautomers, salts and stereoisomers thereof, including mixtures thereof in all ratios;

in aspect 22, to compounds according to aspects 1-21 in which
$R^4$ denotes 4-(pyridin-4-yloxy)phenyl, 4-(pyridin-4-yloxy)-phenylmethyl or 4-(benzo-1,2,5-thiadiazol-5-yloxy)phenyl, where the pyridine radical may be substituted by $CONHCH_3$,
and pharmaceutically usable derivatives, solvates, tautomers, salts and stereoisomers thereof, including mixtures thereof in all ratios;

in aspect 23, to compounds according to aspects 1-22 in which
$Het^1$ denotes an unsubstituted monocyclic saturated or aromatic heterocycle having 1 to 2 N and/or O atoms, or

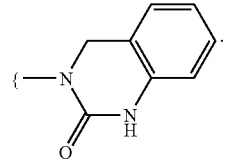

and pharmaceutically usable derivatives, solvates, tautomers, salts and stereoisomers thereof, including mixtures thereof in all ratios;

in aspect 24, to compounds according to aspects 1-23 in which
$Het^1$ denotes morpholinyl, pyrrolidinyl, piperidinyl, pyridyl or

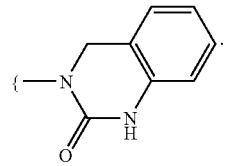

and pharmaceutically usable derivatives, solvates, tautomers, salts and stereoisomers thereof, including mixtures thereof in all ratios;

in aspect 25, to compounds according to aspects 1-24 in which
$Het^2$ denotes an unsubstituted monocyclic aromatic heterocycle having 1-2 N, O and/or S atoms,
and pharmaceutically usable derivatives, solvates, tautomers, salts and stereoisomers thereof, including mixtures thereof in all ratios;

in aspect 26, to compounds according to aspects 1-25 in which
$R^1$ denotes A, OH, $NH_2$, —$(CH_2)_m$—Ar or —$(CH_2)_m$—$Het^2$,
m denotes 0,
Ar denotes phenyl which is unsubstituted or mono-, di- or trisubstituted by Hal, A, OA, COOH or COOA,
$R^2$ if X=N is absent or
if X=C
denotes H, CN, COOA or phenyl,
$R^3$ denotes H, A, —S—A, phenyl, NH-benzyl, —$(CH_2)_p$—Het, NH—$(CH_2)_p$—Het, $NA_2$, NH-alkylene-$NA_2$ or NA-alkylene-$NA_2$,
and pharmaceutically usable derivatives, solvates, tautomers, salts and stereoisomers thereof, including mixtures thereof in all ratios;

in aspect 27, to compounds according to aspects 1-26 in which
$R^2$ if X=N is absent or
if X=C
denotes H, CN, $(CH_2)_o Ar''$, $(CH_2)_o COOA$ or $SO_2A$,
Ar'' denotes phenyl which is unsubstituted or mono-, di- or trisubstituted by Hal or OA,
o denotes 0 or 1, and pharmaceutically usable derivatives, solvates, tautomers, salts and stereoisomers thereof, including mixtures thereof in all ratios;

in aspect 28, to compounds according to aspects 1-27 in which
$R^1$ denotes A, OH, $NH_2$, —$(CH_2)_m$—Ar' or —$(CH_2)_m$—$Het^2$,
Ar' denotes phenyl which is unsubstituted or mono-, di- or trisubstituted by Hal, OA, A or COOA,
m denotes 0,
$Het^2$ denotes thienyl, furyl, imidazolyl, pyrrolyl, thiazolyl or pyridyl,
and pharmaceutically usable derivatives, solvates, tautomers, salts and stereoisomers thereof, including mixtures thereof in all ratios;

in aspect 29, to compounds according to aspects 1-28 in which
X denotes C or N,
B denotes N, CH or C—CN,
$R^1$ denotes A, OH, $NH_2$, —$(CH_2)_m$—Ar' or —$(CH_2)_m$—$Het^2$,
Ar' denotes phenyl which is unsubstituted or mono-, di- or trisubstituted by Hal, OA, A or COOA,
m denotes 0,
$Het^2$ denotes thienyl, furyl, imidazolyl, pyrrolyl, thiazolyl or pyridyl,
$R^2$ if X=N is absent or
if X=C
denotes H, CN, $(CH_2)_o$Ar", $(CH_2)_o$COOA or $SO_2A$,
Ar" denotes phenyl which is unsubstituted or mono-, di- or trisubstituted by Hal or OA,
o denotes 0 or 1,
$R^3$ denotes H, A, —S—A, phenyl, NH-benzyl, —$(CH_2)_p$—Het, NH—$(CH_2)_p$—Het, $NA_2$, NH-alkylene-$NA_2$ or NA-alkylene-$NA_2$,
Het denotes piperazinyl, piperidinyl, morpholinyl, pyrrolidinyl, pyridyl or furyl, which are unsubstituted or may be mono-, di- or trisubstituted by Hal, A, NHA, $NA_2$, COOA, benzyl, —$(CH_2)_t$—OH or —$(CH_2)_p$—$Het^1$,
$Het^1$ denotes morpholinyl, pyrrolidinyl, pyridyl or

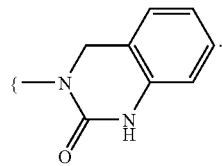

$R^4$ denotes —$(DH_2)_s$—$(Ar^1)_n$—Y—$R^6$,
Y denotes O or $(CH_2)_q$,
$R^5$ denotes H or $CH_3$,
$R^4$ and $R^5$ together also denote

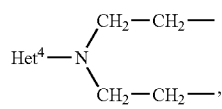

$R^6$ denotes $Het^4$, —$(CH_2)_r$—$NH_2$, —$(CH_2)_r$—NHA or —$(CH_2)_r$—$NA_2$,
$Het^4$ denotes pyridyl, benzo-1,2,5-thiadiazol-5-yl, piperazine, thiazole or imidazole, each of which is unsubstituted or monosubstituted by CONHA, A and/or $Ar^2$, $Ar^1$ denotes phenylene or piperazinediyl,
$Ar^2$ denotes phenyl which is unsubstituted or mono-, di- or trisubstituted by A,
$R^7$, $R^8$, $R^9$, $R^{10}$ each, independently of one another, denote H, A or —$(CH_2)_p$—Ar,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if X=C,
$R^1$ and $R^2$ together may also denote —$(CH_2)_4$— or
$R^2$ and $R^3$ together may also denote —($CHR^7$—$NR^8$—$CHR^9$—$CHR^{10}$)—,
and, if $Ar^1$ denotes piperazinediyl, $R^6$ may also denote H or alkyl having 1-6 C atoms,
and pharmaceutically usable derivatives, solvates, tautomers, salts and stereoisomers thereof, including mixtures thereof in all ratios;

in aspect 30, to compounds according to aspects 1-29 in which
X denotes C or N,
B denotes N, CH or C—CN,
$R^1$ denotes A, OH, $NH_2$, —$(CH_2)_m$—Ar' or —$(CH_2)_m$—$Het^2$,
Ar' denotes phenyl which is unsubstituted or mono-, di- or trisubstituted by Hal, OA, A or COOA,
m denotes 0,
$Het^2$ denotes an unsubstituted monocyclic aromatic heterocycle having 1-2 N, O and/or S atoms,
$R^2$ if X=N is absent or
if X=C
denotes H, CN, $(CH_2)_o$Ar", $(CH_2)_o$COOA or $SO_2A$,
Ar" denotes phenyl which is unsubstituted or mono-, di- or trisubstituted by Hal or OA,
o denotes 0 or 1,
$R^3$ denotes H, A, —S—A, phenyl, NH-benzyl, —$(CH_2)_p$—Het, NH—$(CH_2)_p$—Het, $NA_2$, NH-alkylene-$NA_2$ or NA-alkylene-$NA_2$,
Het denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_t$—OH or —$(CH_2)_p$—$Het^1$,
$Het^1$ denotes morpholinyl, pyrrolidinyl, pyridyl or

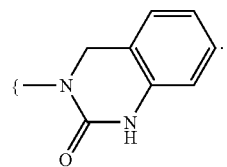

$R^4$ denotes —$(CH_2)_s$—$(Ar^1)_n$—Y—$R^6$,
Y denotes O or $(CH_2)_q$,
$R^5$ denotes H or $CH_3$, $R^4$ and $R^5$ together also denote

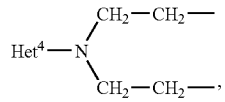

$R^6$ denotes $Het^4$, —$(CH_2)_r$—$NH_2$, —$(CH_2)_r$—NHA or —$(CH_2)_r$—$NA_2$, $Het^4$ denotes a monocyclic saturated or aromatic heterocycle having 1 to 3 N, O and/or S atoms, which may be unsubstituted or mono-, di- or trisubstituted by A, $CONH_2$, CONHA, $CONA_2$ or $Ar^2$, $Ar^1$ denotes phenylene or piperazinediyl, $Ar^2$ denotes phenyl which is unsubstituted or mono-, di- or trisubstituted by A, $R^7, R^8, R^9, R^{10}$ each, independently of one another, denote H, A or —$(CH_2)_p$—Ar, A denotes alkyl having 1 to 10 C atoms, where, in addition, 1-7 H atoms may be replaced by F and/or chlorine, n denotes 0 or 1, p denotes 0, 1, 2, 3 or 4, q denotes 0, 1, 2, 3 or 4, r denotes 0, 1, 2, 3 or 4, s denotes 0, 1, 2, 3 or 4, t denotes 1, 2, 3 or 4, Hal denotes F, Cl, Br or I, and, if X=C, $R^1$ and $R^2$ together ma also denote —$(CH_2)_4$— or $R^2$ and $R^3$ together may also denote —$(CHR^7$—$NR^8$—$CHR^9$—$CHR^{10})$—, and, if $Ar^1$ denotes piperazinediyl, $R^6$ may also denote H or alkyl having 1-6 C atoms, and pharmaceutically usable derivatives, solvates, tautomers, salts and stereoisomers thereof, including mixtures thereof in all ratios;

in aspect 31, to compounds according to aspects 1-30 in which

X denotes N,

B denotes N, CH or C—CN, $R^1$ denotes $NH_2$, $R^2$ is absent, $R^3$ denotes H, A, —S—A, phenyl, NH-benzyl, —$(CH_2)_p$—Het, NH—$(CH_2)_p$—Het, $NA_2$, NH-alkylene-$NA_2$ or NA-alkylene-$NA_2$, Het denotes piperazinyl, piperidinyl, morpholinyl, pyrrolidinyl, pyridyl or furyl, which are unsubstituted or may be mono-, di- or trisubstituted by Hal, A, NHA, $NA_2$, COOA, benzyl, —$(CH_2)_t$—OH or —$(CH_2)_p$—$Het^1$, $Het^1$ denotes morpholinyl, pyrrolidinyl, pyridyl or

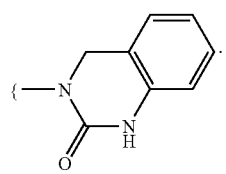

$R^4$ denotes —$(CH_2)_s$—$(Ar^1)_n$—Y—$R^6$,

Y denotes O or $(CH_2)_q$, $R^5$ denotes H or $CH_3$, $R^4$ and $R^5$ together also denote

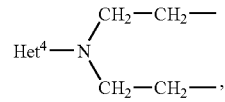

$R^6$ denotes $Het^4$, —$(CH_2)_r$—$NH_2$, —$(CH_2)_r$—NHA or —$(CH_2)_r$—$NA_2$, $Het^4$ denotes pyridyl, benzo-1,2,5-thiadiazol-5-yl, piperazine, thiazole or imidazole, each of which is unsubstituted or monosubstituted by CONHA, A and/or $Ar^2$, $Ar^1$ denotes phenylene or piperazinediyl, $Ar^2$ denotes phenyl which is unsubstituted or mono-, di- or trisubstituted by A, A denotes alkyl having 1 to 10 C atoms, where, in addition, 1-7 H atoms may be replaced by F and/or chlorine, n denotes 0 or 1, p denotes 0, 1, 2, 3 or 4, q denotes 0, 1, 2, 3 or 4, r denotes 0, 1, 2, 3 or 4, s denotes 0, 1, 2, 3 or 4, t denotes 1, 2, 3 or 4, Hal denotes F, Cl, Br or I, and, if $Ar^1$ denotes piperazinediyl, $R^6$ may also denote H or alkyl having 1-6 C atoms, and pharmaceutically usable derivatives, solvates, tautomers, salts and stereoisomers thereof, including mixtures thereof in all ratios;

in aspect 32, to compounds according to aspects 1-31 in which

X denotes N,

B denotes N, CH or C—CN, $R^1$ denotes $NH_2$, $R^2$ is absent, $R^3$ denotes H, A, —S—A, phenyl, NH-benzyl, —$(CH_2)_p$—Het, NH—$(CH_2)_p$—Het, $NA_2$, NH-alkylene-$NA_2$ or NA-alkylene-$NA_2$, Het denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_t$—OH or —$(CH_2)_p$—$Het^1$, $Het^1$ denotes morpholinyl, pyrrolidinyl, pyridyl or

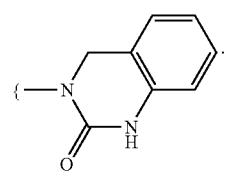

$R^4$ denotes —$(CH_2)_s$—$(Ar^1)_n$—Y—$R^6$,

Y denotes O or $(CH_2)_q$, $R^5$ denotes H or $CH_3$, $R^4$ and $R^5$ together also denote

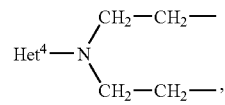

R⁶ denotes Het⁴, —(CH₂)_r—NH₂, —(CH₂)_r—NHA or —(CH₂)_r—NA₂,

Het⁴ denotes a monocyclic saturated or aromatic heterocycle having 1 to 3 N, O and/or S atoms, which may be unsubstituted or mono- di- or trisubstituted by A, CONH₂, CONHA, CONA₂ or Ar², Ar¹ denotes phenylene or piperazinediyl, Ar² denotes phenyl which is unsubstituted or mono-, di- or trisubstituted by A, A denotes alkyl having 1 to 10 C atoms, where, in addition, 1-7 H atoms may be replaced by F and/or chlorine, n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I, and, if Ar¹ denotes piperazinediyl, R⁶ may also denote H or alkyl having 1-6 C atoms, and pharmaceutically usable derivatives, solvates, tautomers, salts and stereoisomers thereof, including mixtures thereof in all ratios; and in aspect 33, to compounds according to aspects 1, selected from the group (7-phenyl-5-trifluoromethyl-1,2,4-triazolo[1, 5-a]pyrimidin-2-yl)-[4-(pyridin-4-yloxy)phenyl]amine,

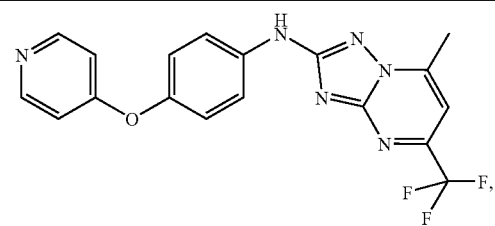

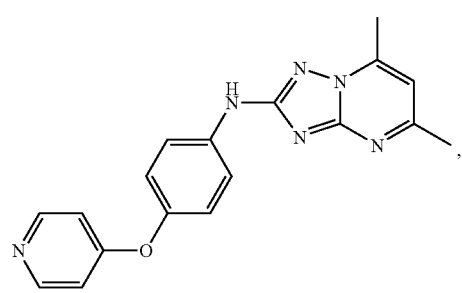

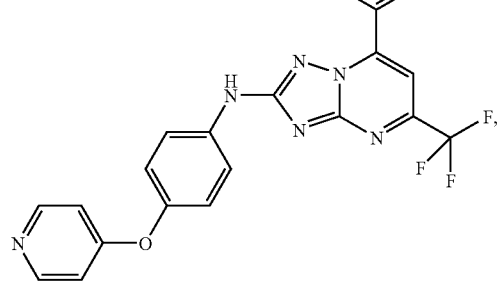

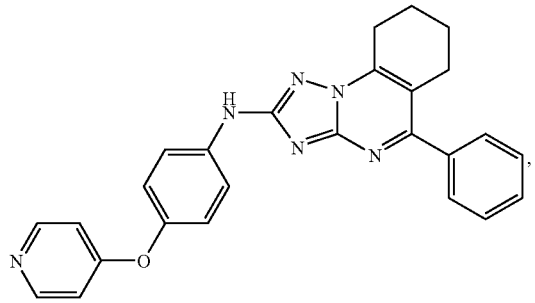

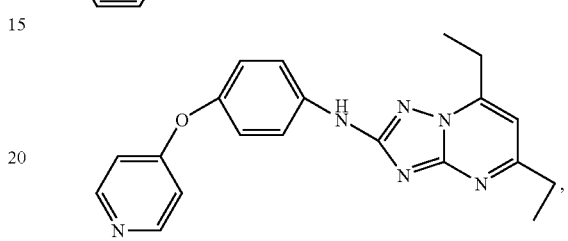

(7-methyl-5-trifluoromethyl-1,2,4-triazolo[1,5-a]pyrimidin-2-yl)-[3-(2-(N-methylaminocarbonyl)pyridin-4yloxy)phenyl]amine, (7-phenyl-5-trifluoromethyl-1,2,4-triazolo[1,5-a]pyrimidin-2-yl)-[3-(2-(N-methylaminocarbonyl)pyridin-4-yloxy)phenyl]amine, (7-methyl-1,2,4-triazolo[1,5-a]pyrimidin-2-yl)-[3-(2-(N-methyl-aminocarbonyl)pyridin-4-yloxy)phenyl]amine, (7-phenyl-5-trifluoromethyl-1,2,4-triazolo[1,5-a]pyrimidin-2-yl)-[4-(2-(N-methylaminocarbonyl)pyridin-4-yloxy)phenyl]amine, (5,7-bistrifluoromethyl-1,2,4-triazolo[1,5-a]pyrimidin-2-yl)-[4-(2-(N-methylaminocarbonyl)pyridin-4-yloxy)phenyl]amine, (5,7-dimethyl-1,2,4-triazolo[1,5-a]pyrimidin-2-yl)-[4-(benzo-1,2,5-thiadiazol-5-yloxy)phenyl]amine, (7-methyl-5-trifluoromethyl-1,2,4-triazolo[1,5-a]pyrimidin-2-yl)-[4-(benzo-1,2,5-thiadiazol-5-yloxy)phenyl]amine, (7-phenyl-5-trifluoromethyl-1,2,4-triazolo[1,5-a]pyrimidin-2-yl)-[4-(benzo-1,2,5-thiadiazol-5-yloxy)phenyl]amine, (2-phenyithiazol-4-ylmethyl)-(7-phenyl-5-trifluoromethyl-1,2,4-triazolo[1,5-a]pyrimidin-2-yl)amine, (2-phenylthiazol-4-ylmethyl)-(7-methyl-5-trifluoromethyl-1,2,4-triazolo[1,5-a]pyrimidin-2-yl)amine, (7-phenyl-5-trifluoromethyl-1,2,4-triazolo[1,5-a]pyrimidin-2-yl)-[4-(pyridin-4-yloxy)benzyl]amine, (3-dimethylaminopropyl)-(7-methyl-5-trifluoromethyl-1,2,4-triazolo-[1,5-a]pyrimidin-2-yl)amine, 7-phenyl-2-[4-(pyridin-4-yloxy)phenylamino]-5-trifluoromethyl-pyrazolo[1,5-a]pyrimidine-3-carbonitrile, 7-methyl-2-[4-(pyridin-4-yloxy)phenylamino]-5-trifluoromethyl-pyrazolo[1,5-a]pyrimidine-3-carbonitrile, 5,7-dimethyl-2-[4-(pyridin-4-yloxy)phenylamino]pyrazolo[1,5-a]-pyrimidine-3-carbonitrile, 7-phenyl-2-[4-(pyridin-4-yloxy)phenylmethylamino]-5-trifluoro-methylpyrazolo[1,5-a]pyrimidine-3-carbonitrile,

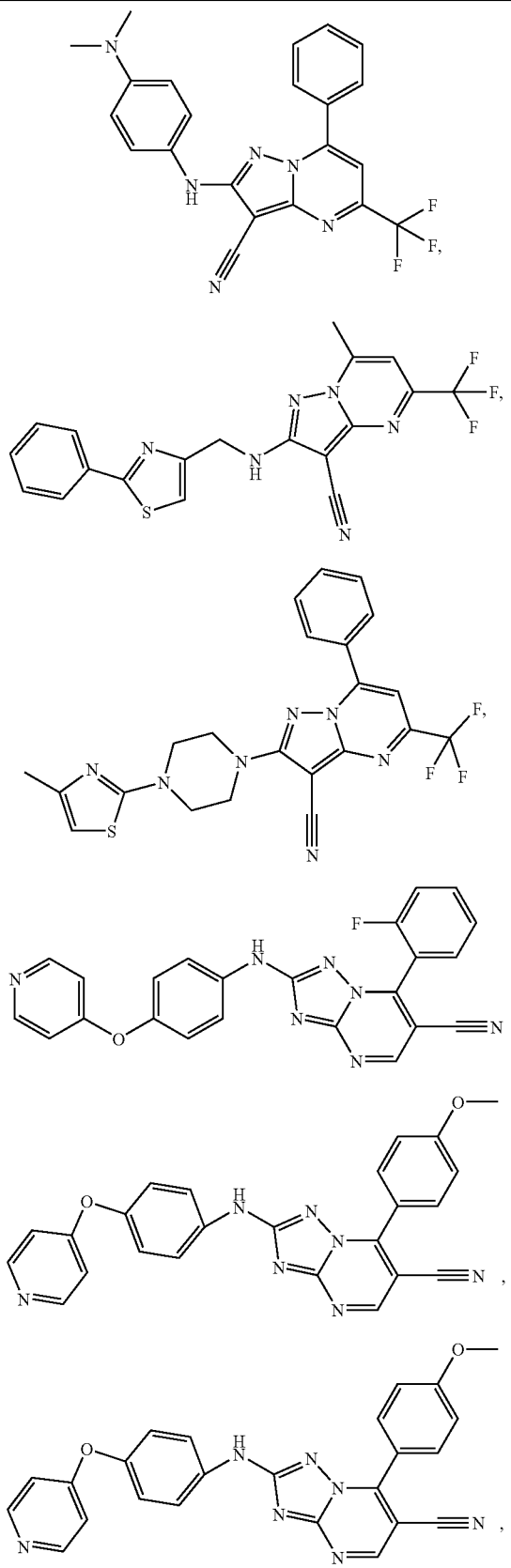
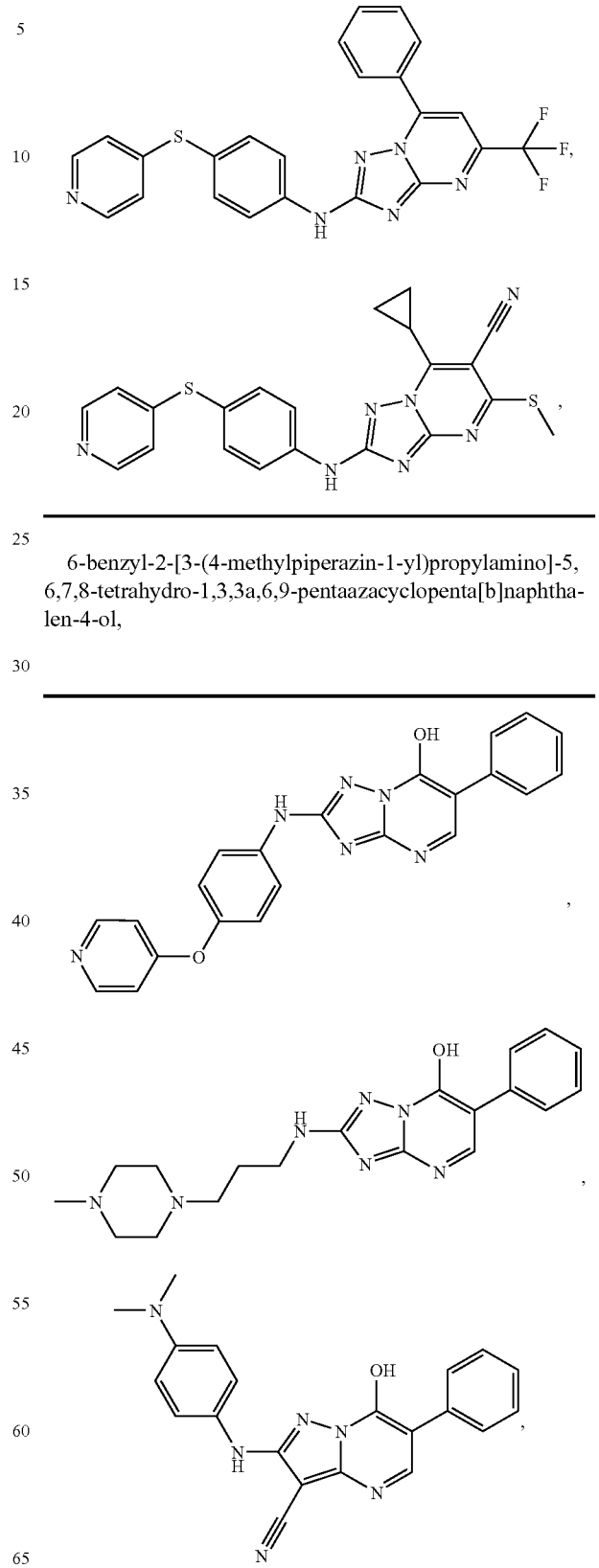
6-benzyl-2-[3-(4-methylpiperazin-1-yl)propylamino]-5,6,7,8-tetrahydro-1,3,3a,6,9-pentaazacyclopenta[b]naphthalen-4-ol,

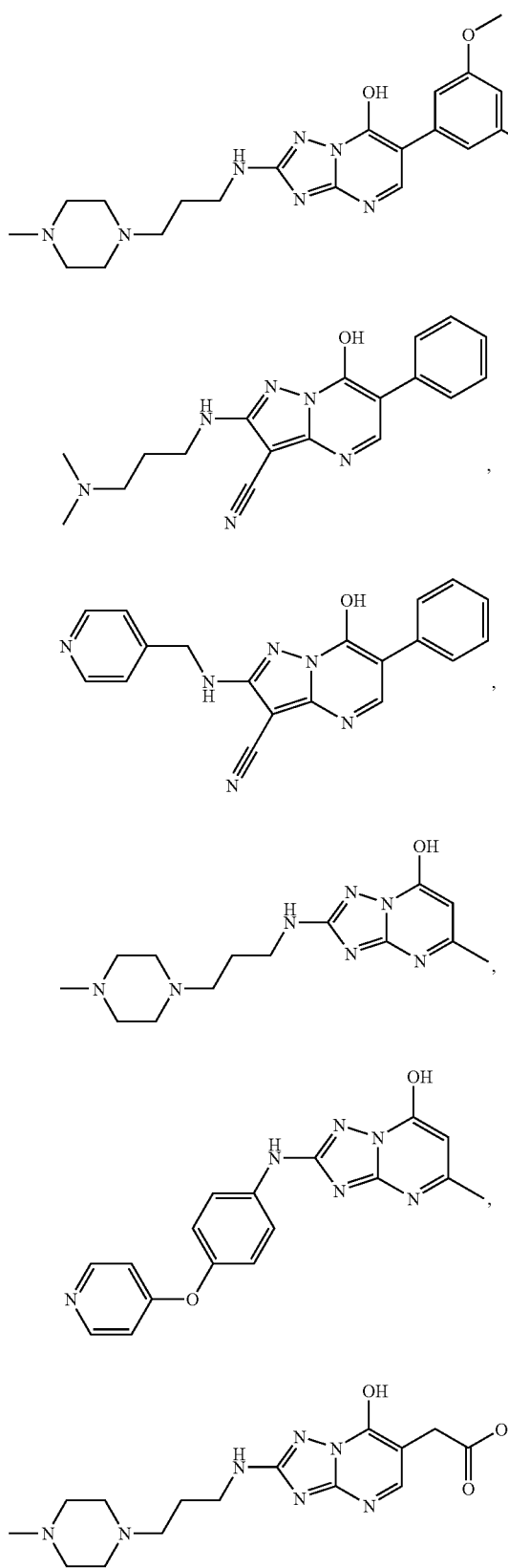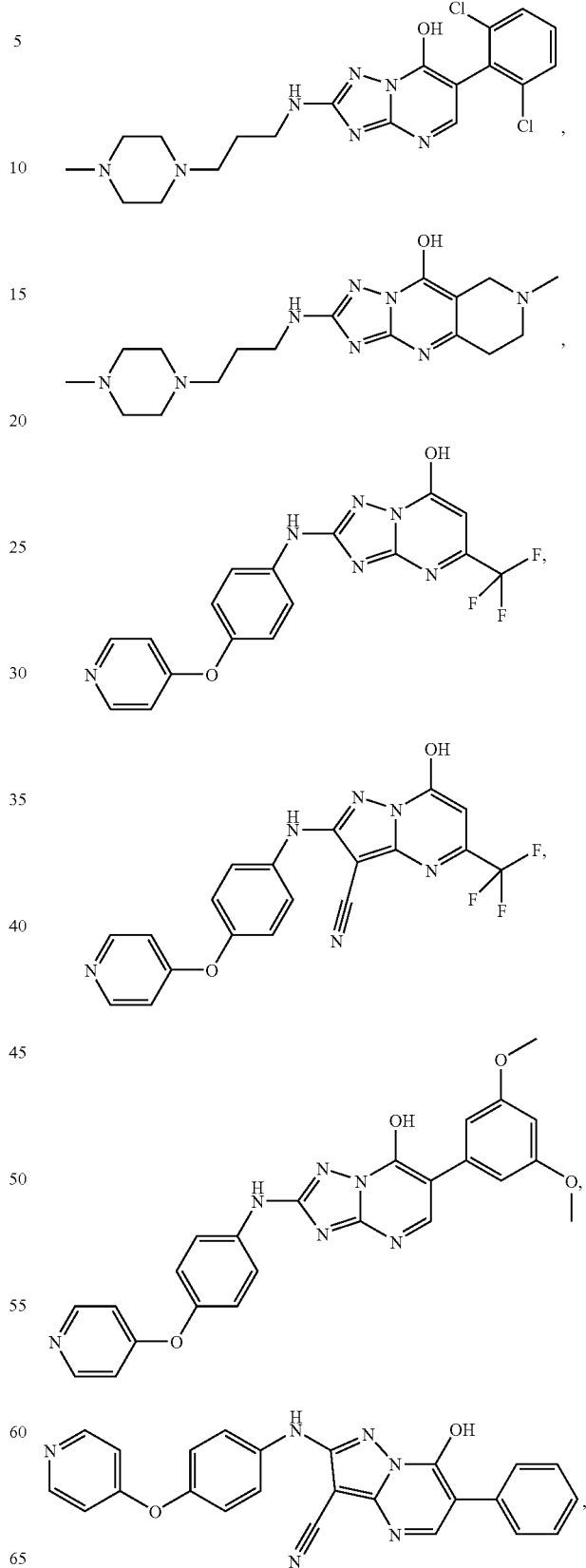

-continued
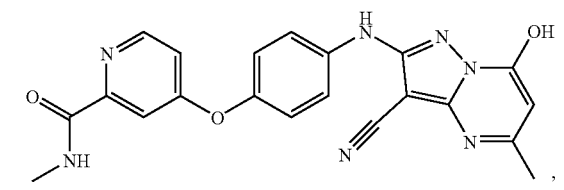
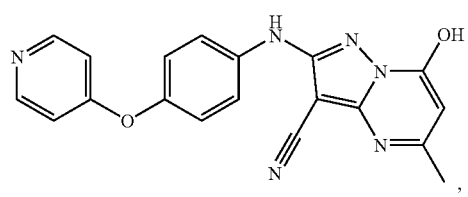
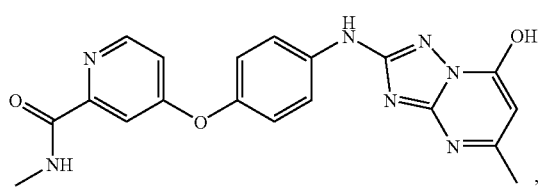
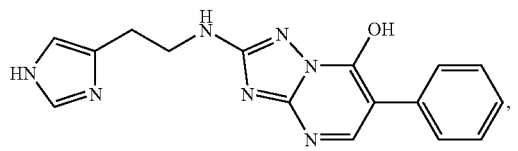
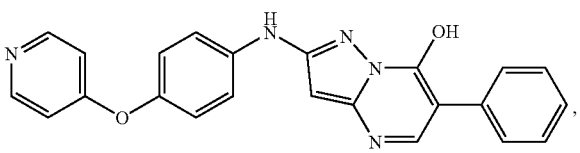
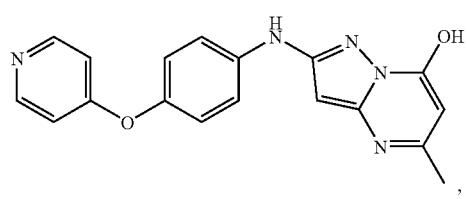
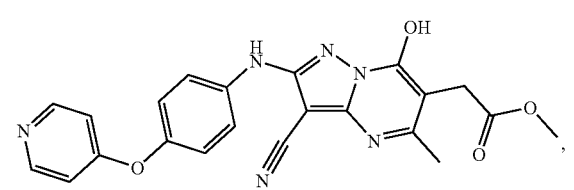
-continued
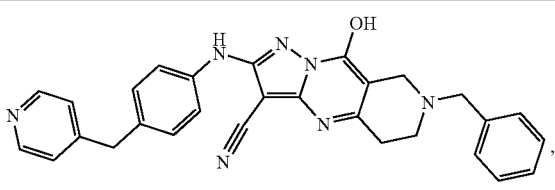
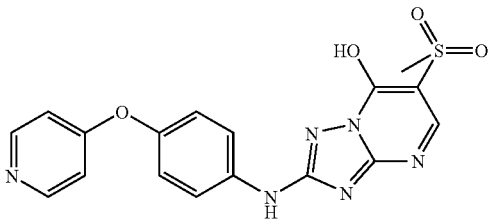
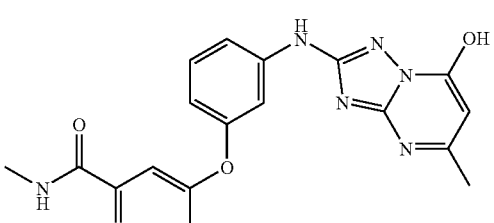
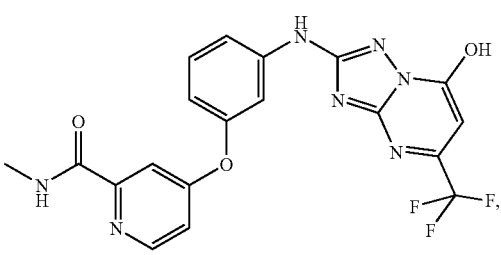
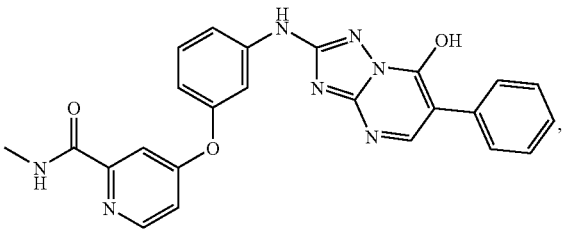
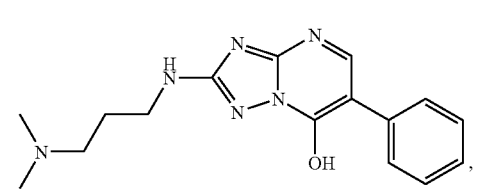
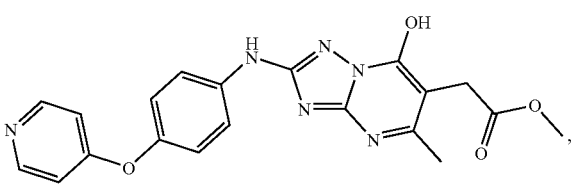

-continued
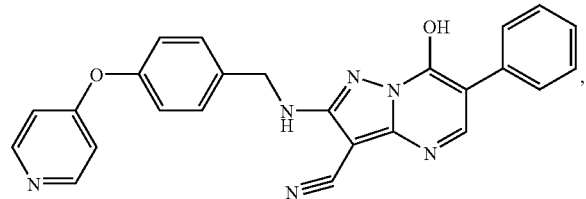
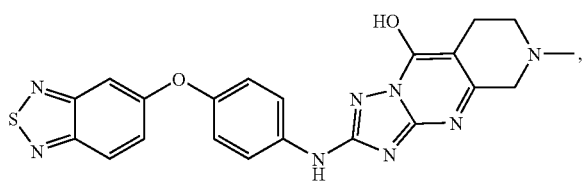
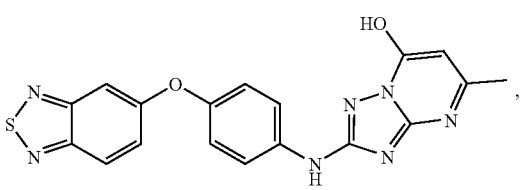
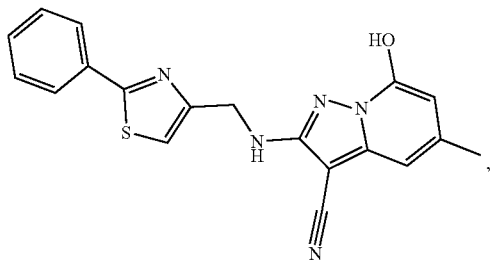
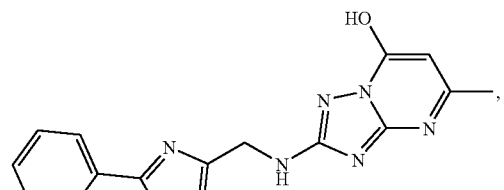
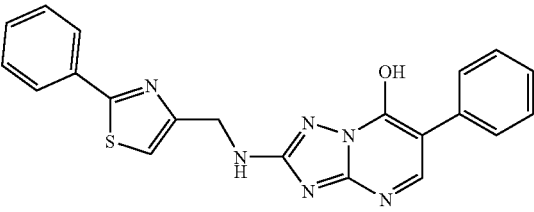
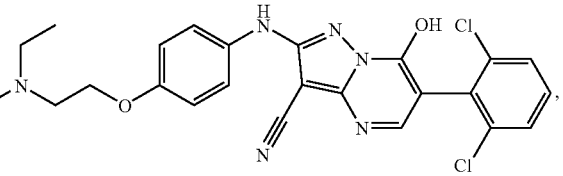
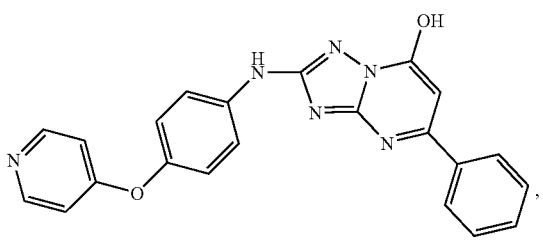

-continued
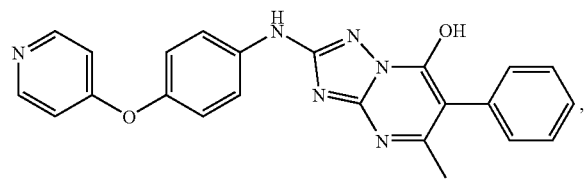
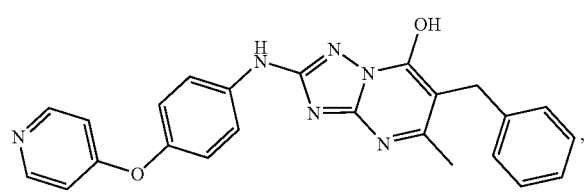
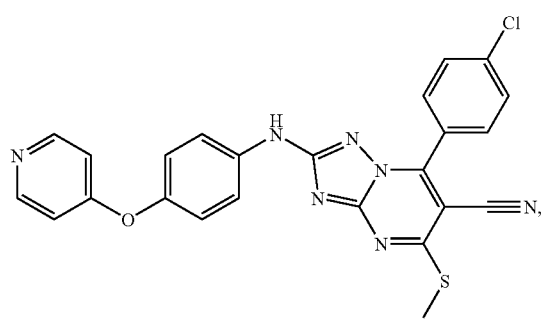
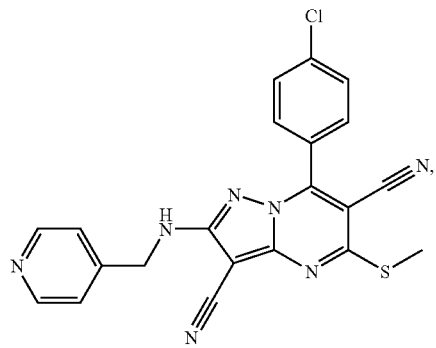
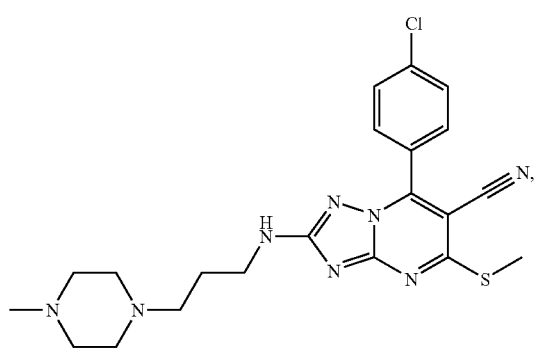
-continued
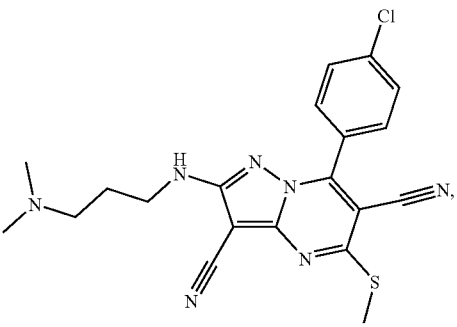
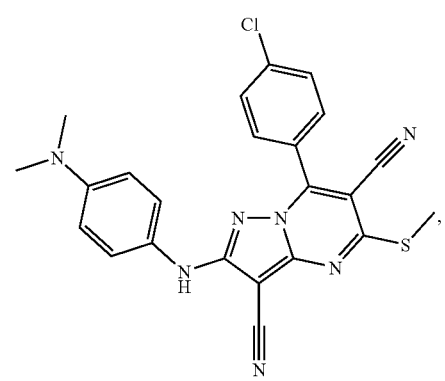
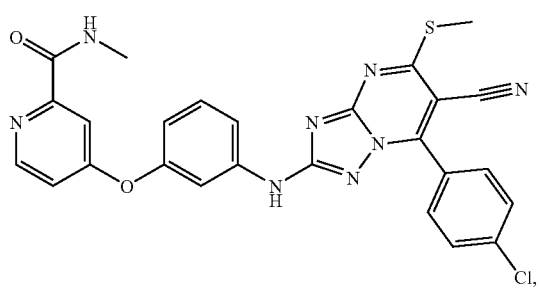
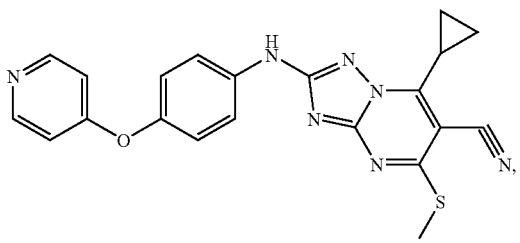
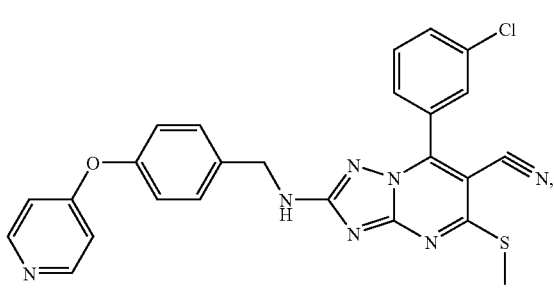

-continued
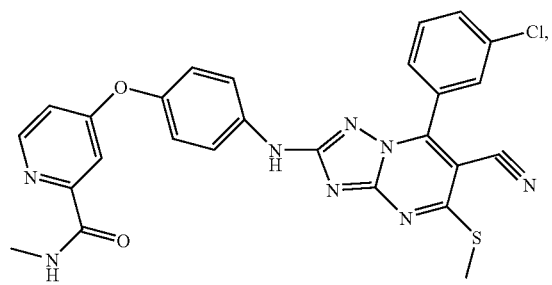
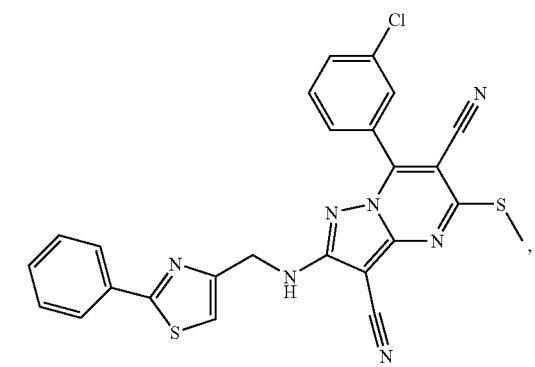
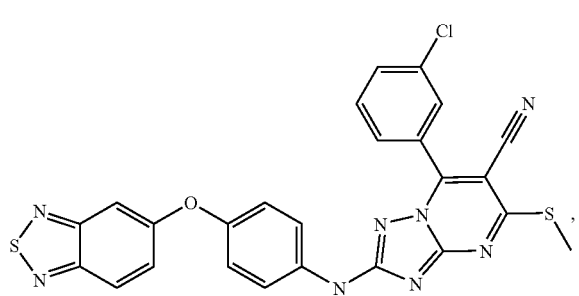
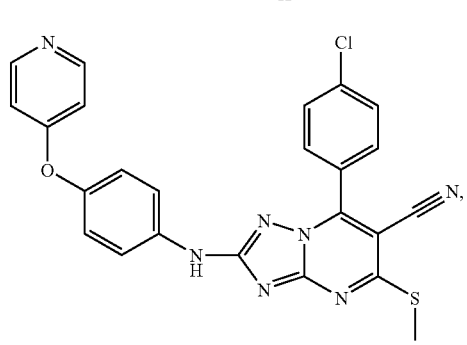
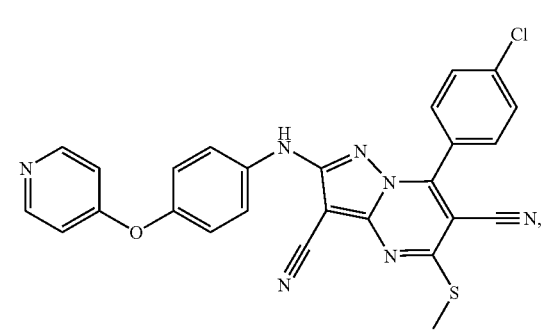
-continued
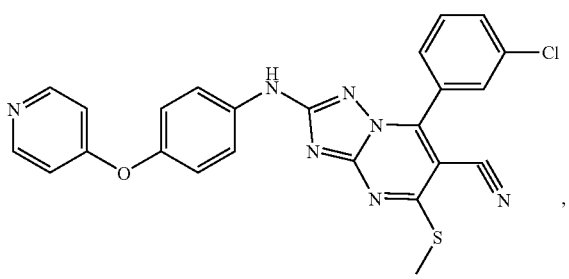
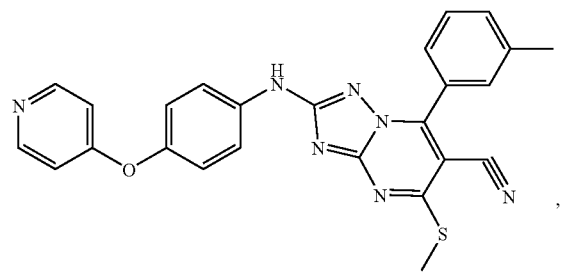
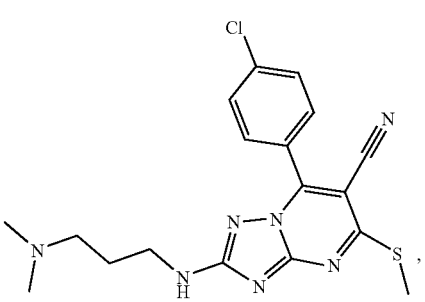
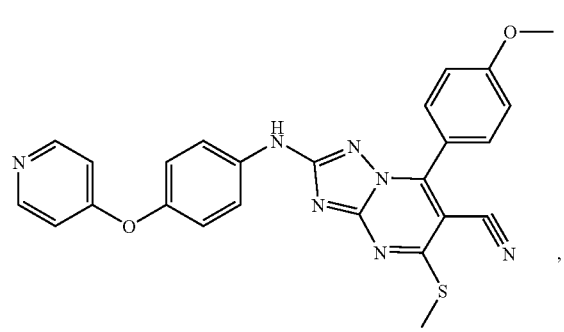
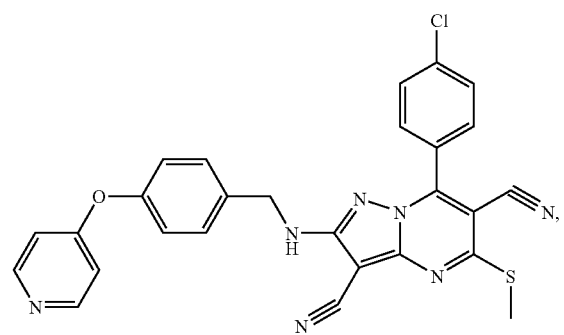

-continued
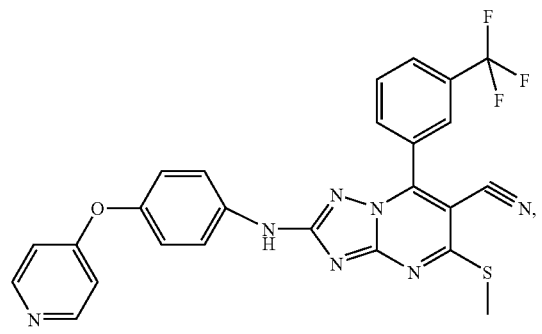
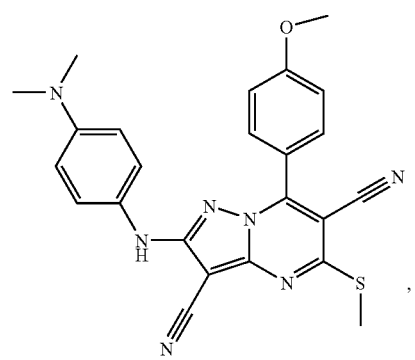
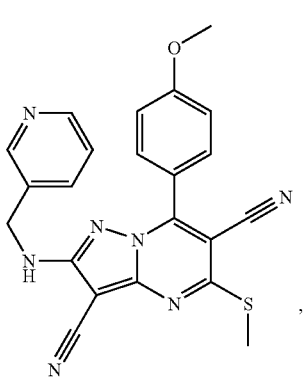
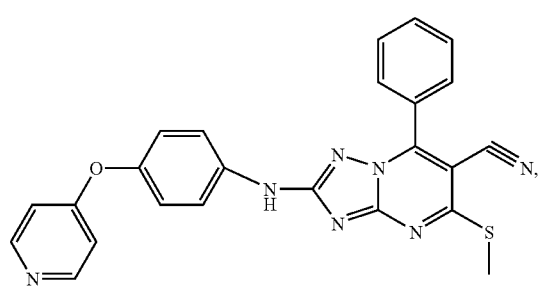
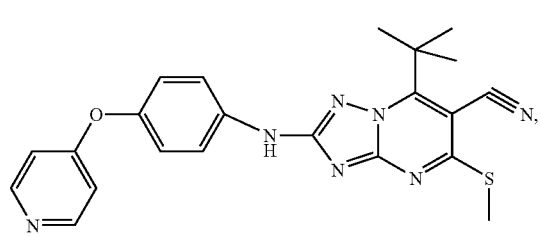
-continued
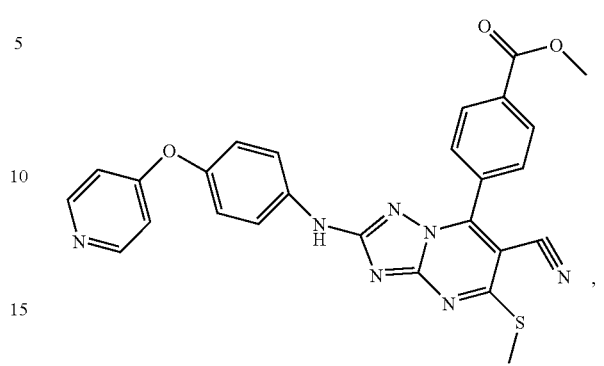
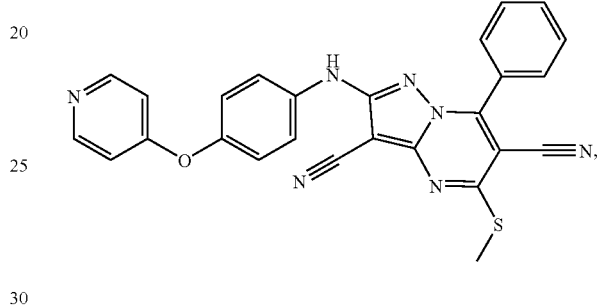
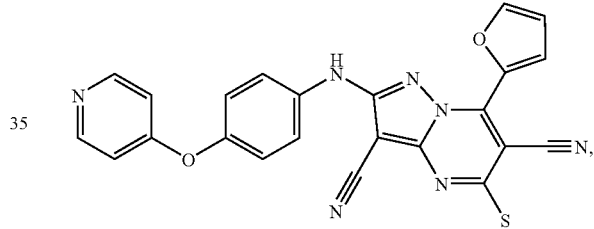
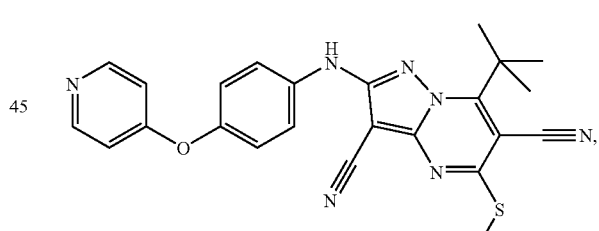
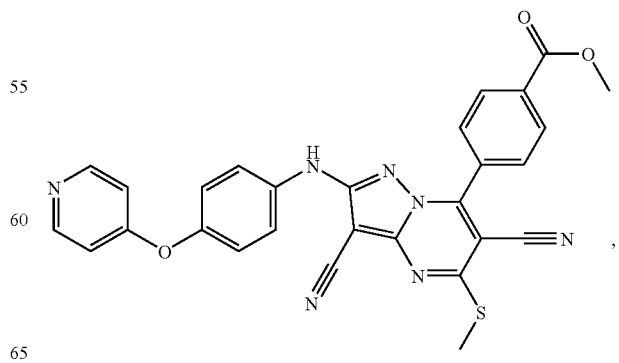

-continued
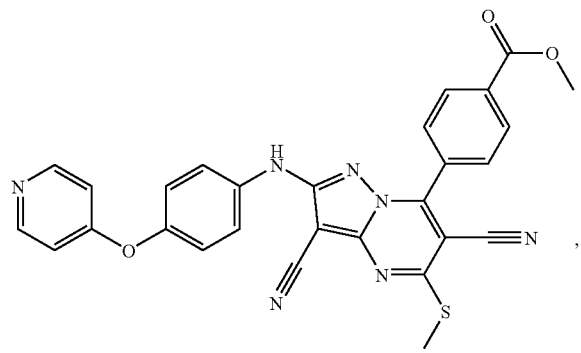
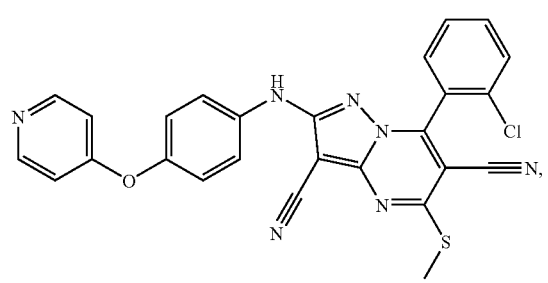
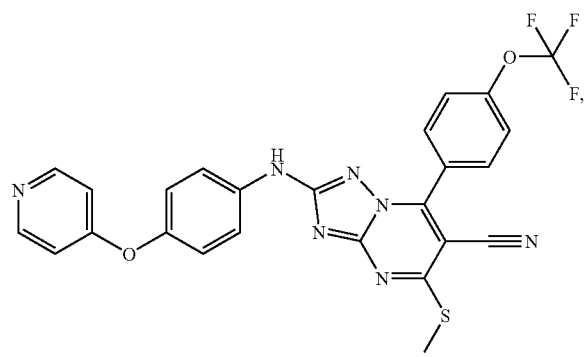
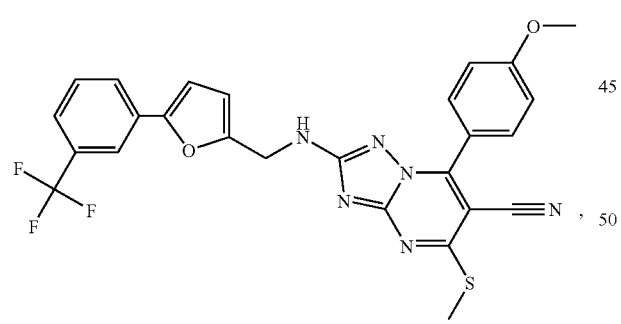
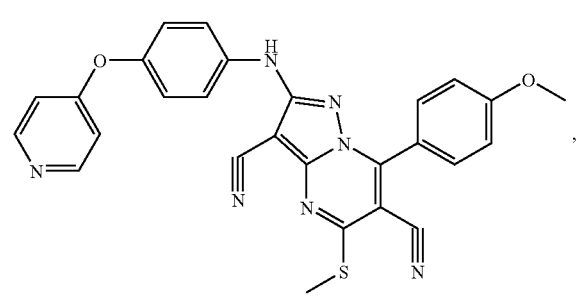
-continued
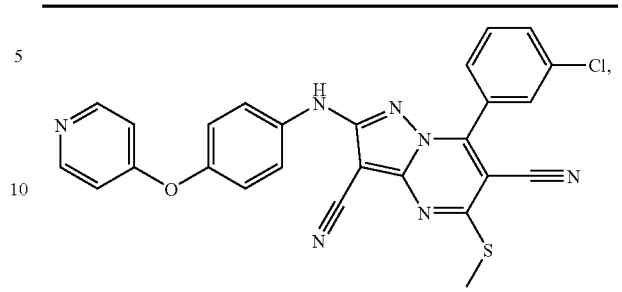
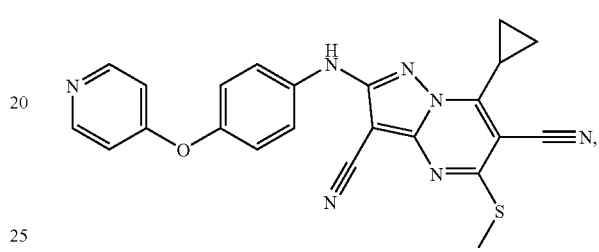
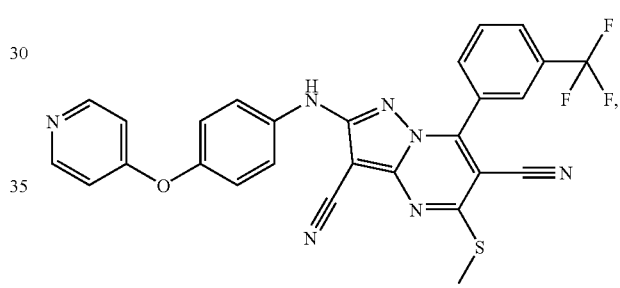
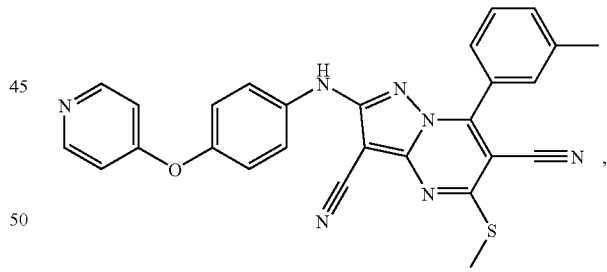
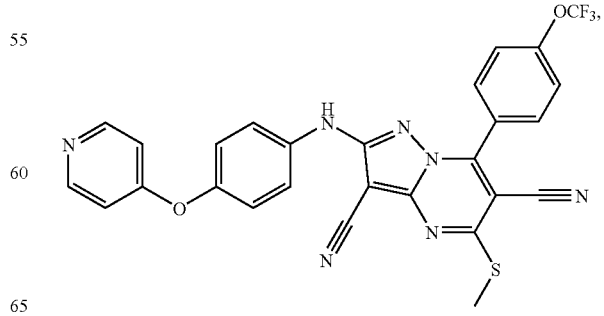

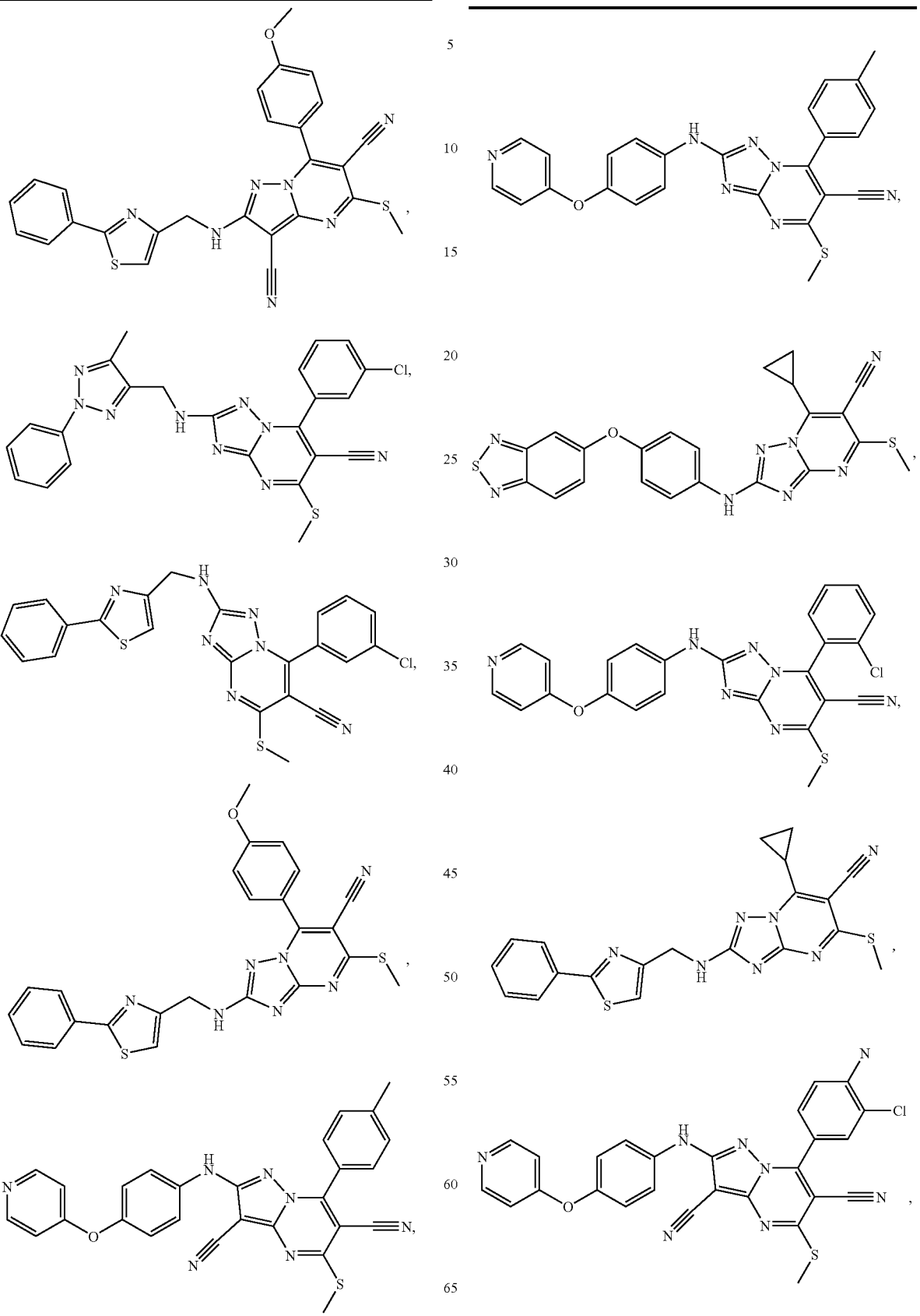

-continued
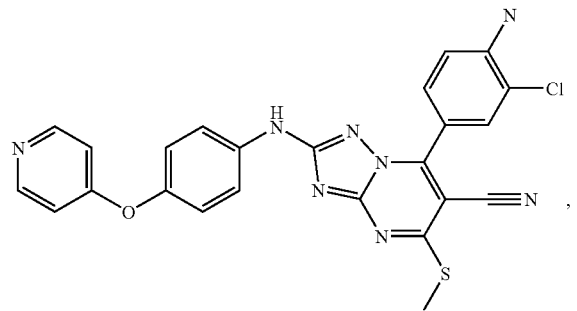
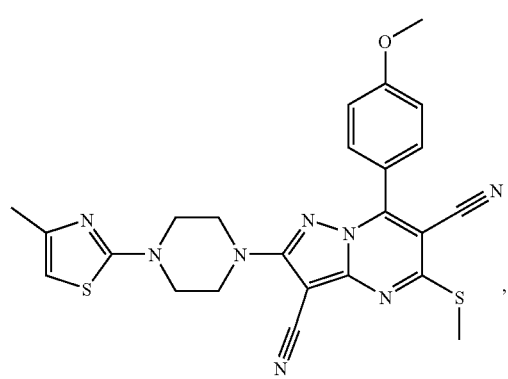
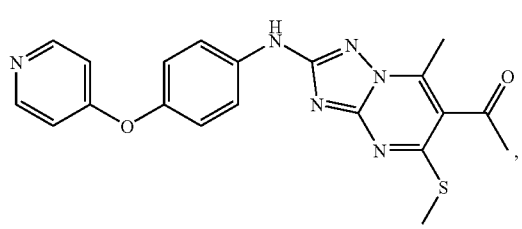
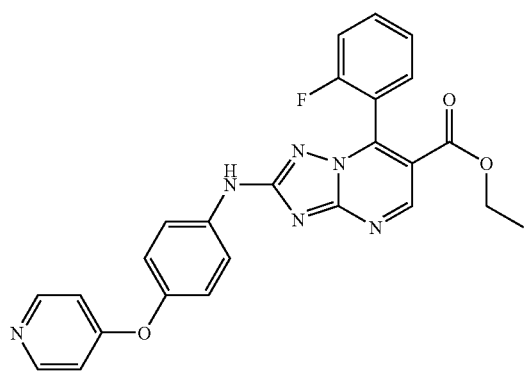
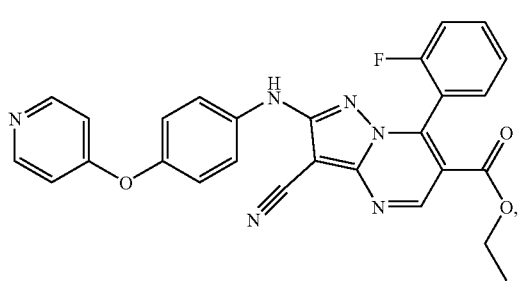
-continued
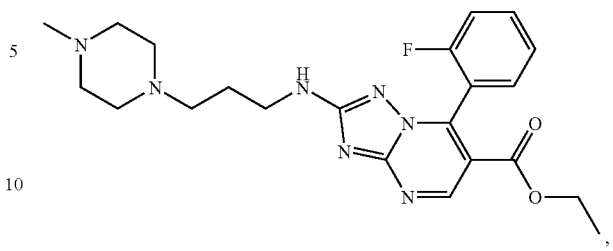
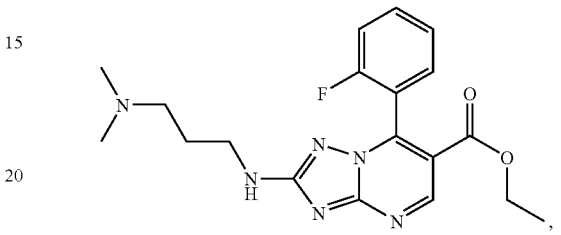
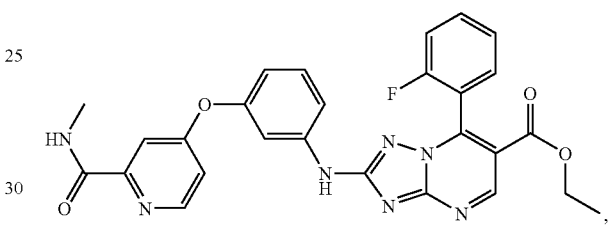
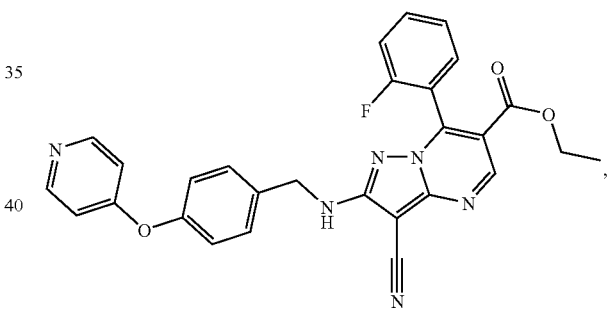
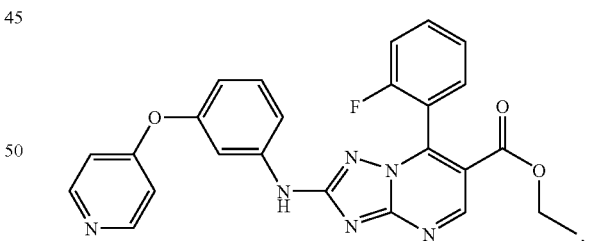
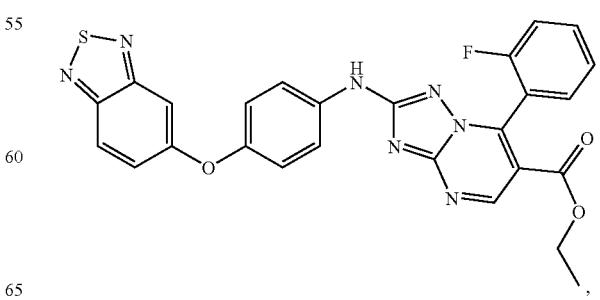

-continued
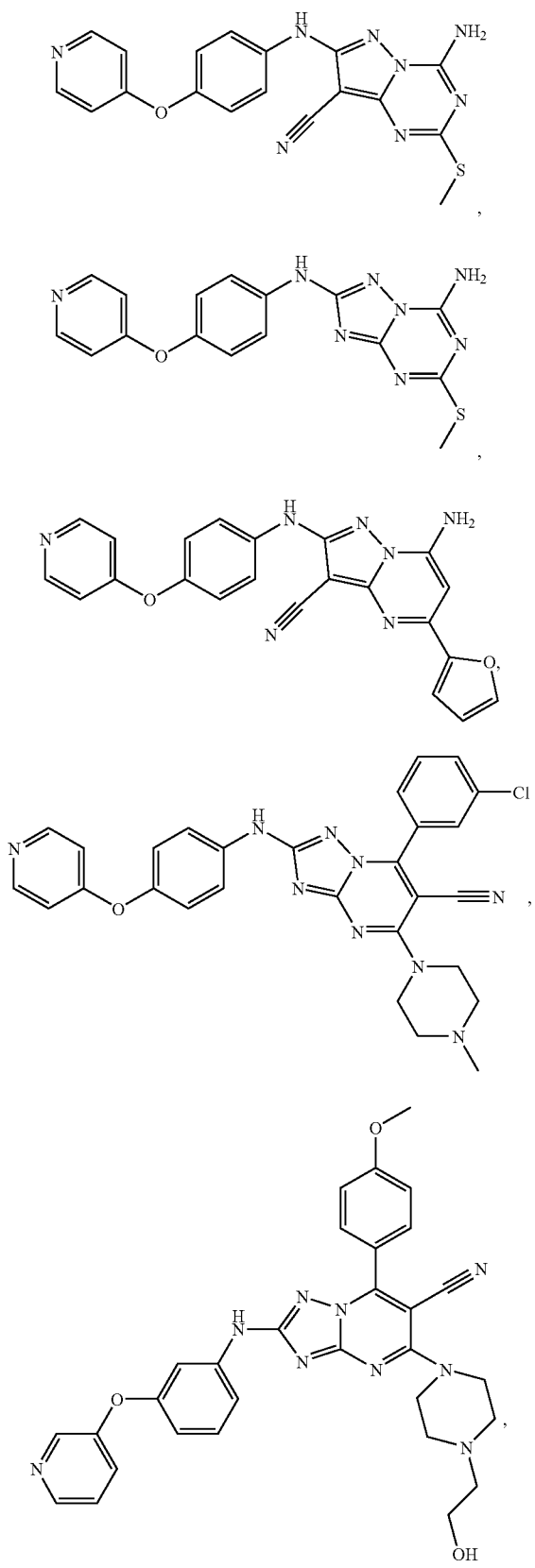
-continued
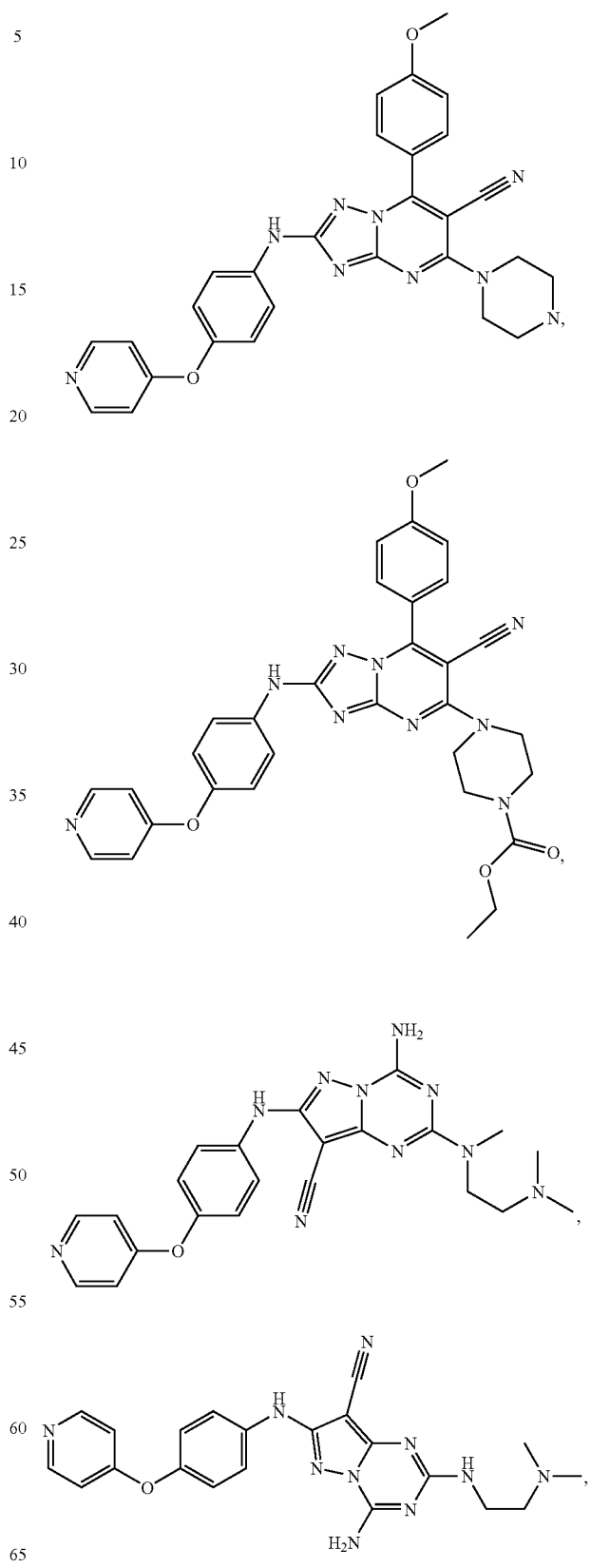

-continued
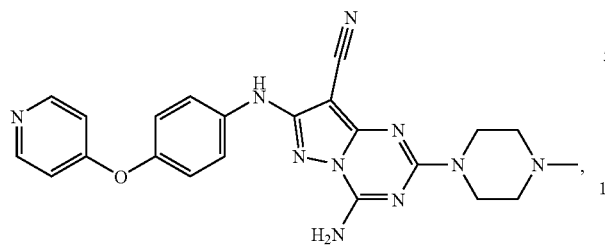
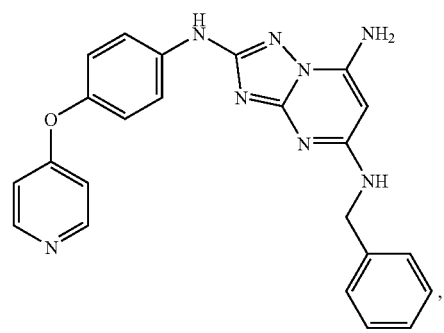
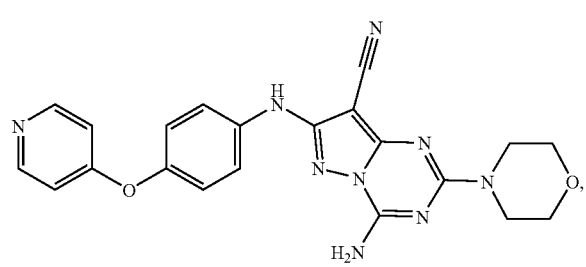
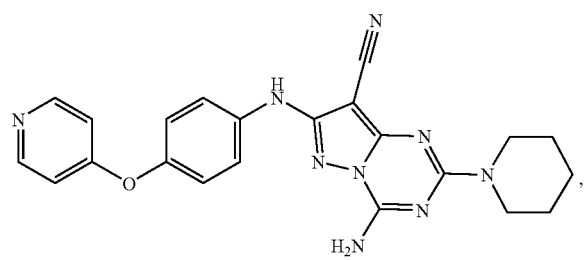
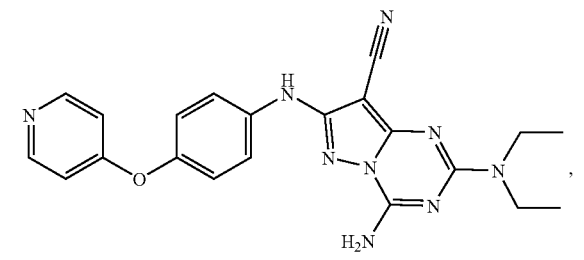
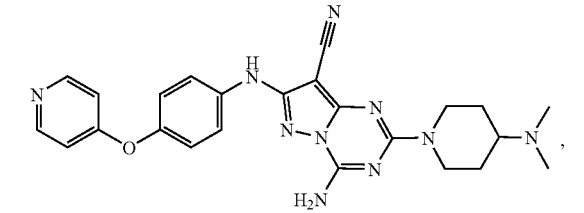
-continued
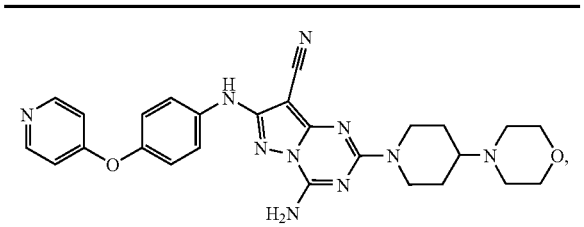
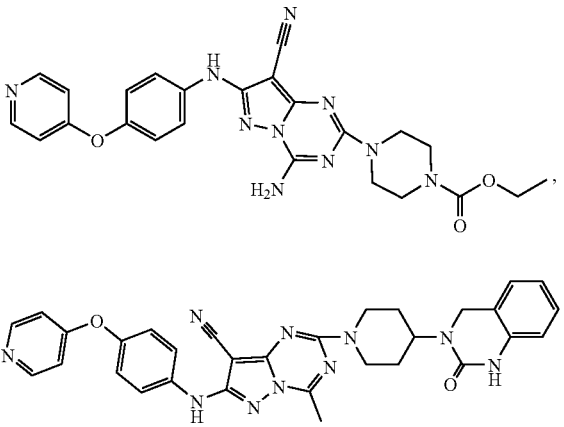
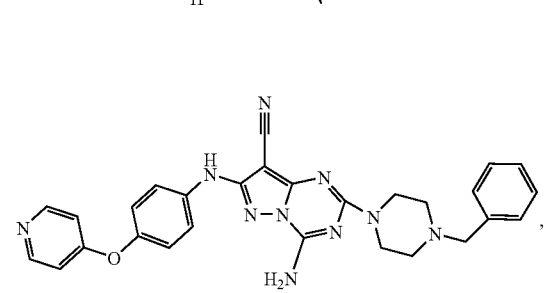
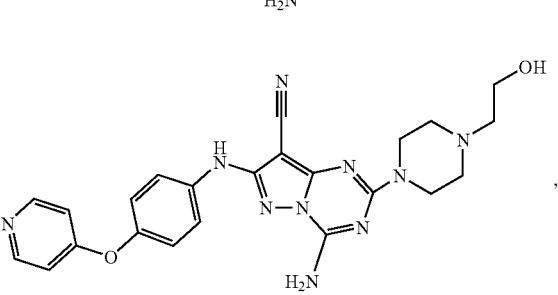
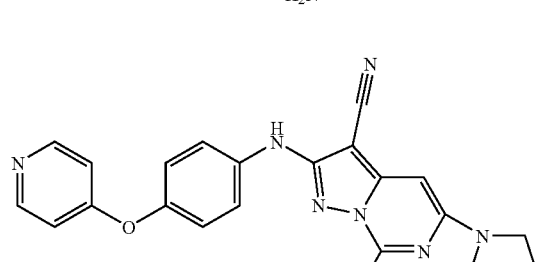
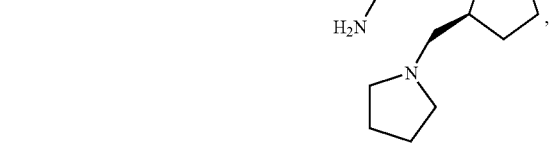

-continued

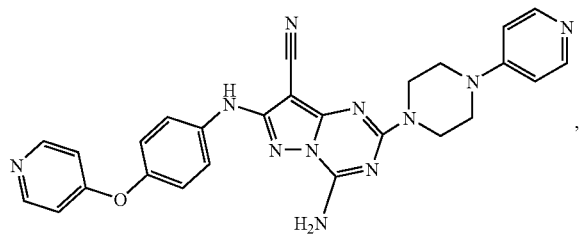,

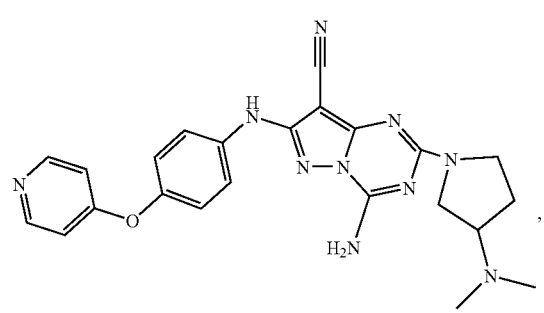,

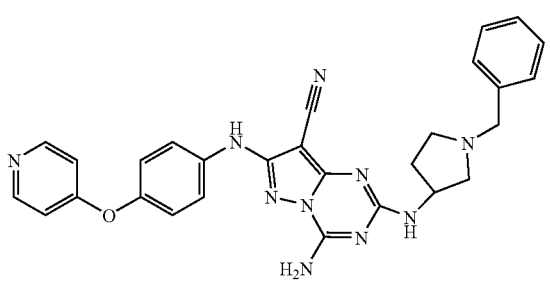,

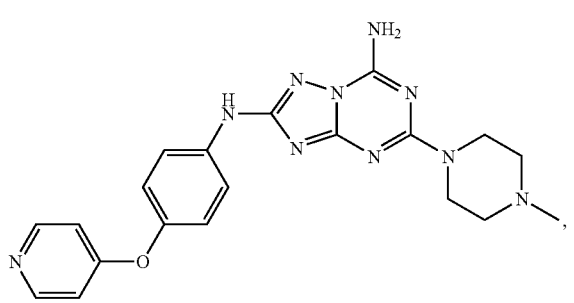,

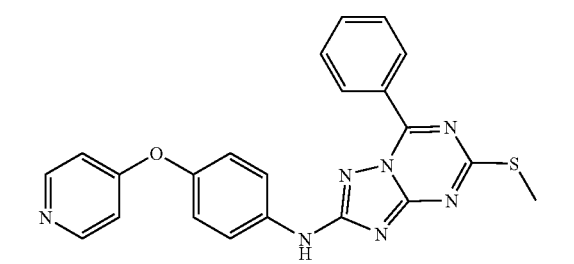

and pharmaceutically usable derivatives, solvates, tautomers, salts and stereoisomers thereof, including mixtures thereof in all ratios;

characterised in that
a) for the preparation of compounds of the formula I
in which X denotes C, a compound of the formula II

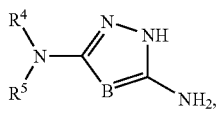

II in which $R^4$, $R^5$ and B have the meanings indicated in aspect 1,
i) is reacted with a compound of the formula IIIa

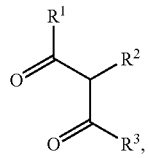

IIIa in which $R^1$ OA and
$R^2$ and $R^3$ have the meanings indicated in aspect 1,
or
ii) with a compound of the formula IIIb

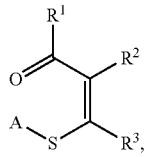

IIIb in which $R^1$, $R^2$ and $R^3$ have the meanings indicated in aspect 1, and A denotes alkyl having 1, 2, 3 or 4 C atoms,
or
iii) with a compound of the formula IIIc

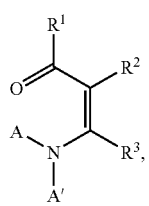

IIIc in which
$R^1$, besides the meanings indicated in aspect 1, also denotes OA,
$R^2$ and $R^3$ have the meanings indicated in aspect 1,
and A, A' each, independently of one another, denote alkyl having 1, 2, 3 or 4 C atoms,
or A and A' together may also form a butylene or pentylene chain, or b) for the preparation of compounds of the formula I
in which X denotes N and $R^1$ denotes $NH_2$,
a compound of the formula II is reacted with a compound of the formula IIId

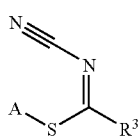

IIId in which $R^3$ has the meaning indicated in aspect 1,
and A denotes alkyl having 1, 2, 3 or 4 C atoms, or c) for the preparation of compounds of the formula I in which X denotes N,
$R^1$ denotes H, A, —$(CH_2)_m$—Ar or —$(CH_2)_m$—$Het^2$,
$R^3$ denotes —S—A,
a compound of the formula II is reacted with a compound of the formula IIIe

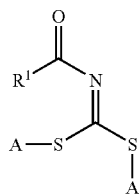

IIIe in which
$R^1$ denotes H, A, —$(CH_2)_m$—Ar or —$(CH_2)_m$—$Het^2$
and A denotes alkyl having 1, 2, 3 or 4 C atoms, and/or that one or more radical(s) $R^1$, $R^2$ and/or $R^3$ in a compound of the formula I is (are) converted into one or more radical(s) $R^1$, $R^2$ and/or $R^3$, by, for example, i) converting an alkylsulfanyl group into an amine,
ii) hydrolysing an ester to the acid, reducing it to the aldehyde or alcohol,
iii) reducing a nitrile to the aldehyde or amine, and/or a base or acid of the formula I is converted into one of its salts.

Above and below, the radicals $R^1$, $R^2$, $R^3$, $R^4$, B and X have the meanings indicated for the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl.

Cycloalkyl preferably denotes cyclopropyl, cyclobutyl, cyclopentyl, cyclohexyl or cycloheptyl.

Alkylene is preferably unbranched and preferably denotes methylene, ethylene, propylene, butylene or pentylene.

$R^1$ preferably denotes A, OH, $NH_2$, —$(CH_2)_m$—Ar', such as, for example, phenyl which is unsubstituted or mono-, di- or trisubstituted by Hal, OA, A or COOA, or —$(CH_2)_m$-$Het^2$, such as, for example, thienyl, furyl, imidazolyl, pyrrolyl, thiazolyl or pyridyl.

If X denotes C, then $R^1$ preferably denotes A, OH, —$(CH_2)_m$—Ar', such as, for example, phenyl which is unsubstituted or mono-, di- or trisubstituted by Hal, OA, A or COOA, or —$(CH_2)_m$-$Het^2$, such as, for example, thienyl, furyl, imidazolyl, pyrrolyl, thiazolyl or pyridyl.

If X denotes N, then $R^1$ preferably denotes $NH_2$.

If X denotes C, then $R^2$ preferably denotes H, CN, $(CH_2)_o$Ar'', $(CH_2)_o$COOA or $SO_2$A, where Ar'' preferably denotes phenyl which is unsubstituted or mono-, di- or trisubstituted by Hal or OA; o preferably denotes 0 or 1.

$R^3$ preferably denotes H, A, —S-A, phenyl, NH-benzyl, —$(CH_2)_p$-Het, NH—$(CH_2)_p$-Het, $NA_2$, NH-alkylene-$NA_2$ or NA-alkylene-$NA_2$, where Het preferably denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_t$—OH or —$(CH_2)_p$-$Het^1$;

in this connection, $Het^1$ preferably denotes an unsubstituted monocyclic saturated or aromatic heterocycle having 1 to 2 N and/or O atoms, or

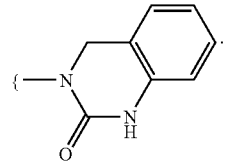

In particular, $Het^1$ denotes morpholinyl, pyrrolidinyl, piperidinyl, piperazinyl, pyrazinyl, pyridyl, furyl, thienyl or

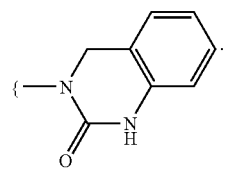

In particular, $Het^1$ denotes morpholinyl, pyrrolidinyl, pyridyl, or

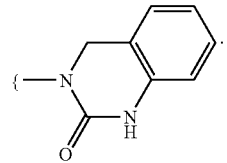

Ar preferably denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH.

Aryl denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)-phenyl, o-, m- or p-acetamidophenyl, o-, m- or p-methoxyphenyl, o-, m- or p-ethoxyphenyl, o-, m- or p-ethoxy-carbonylphenyl, o-, m- or p-(N,N-dimethylamino) phenyl, o-, m- or p-(N,N-di-methylaminocarbonyl)-phenyl, o-, m- or p-(N-ethylamino)-phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)-phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N, N-dimethylamino- or 3-nitro-4-N, N-dimethylaminophenyl, 2,3-diaminophenyl, 2,3,4-, 2,3,5-, 2,3,6-, 2,4,6- or 3,4,5-trichlorophenyl 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Het preferably denotes a mono- or bicyclic saturated, unsaturated or aromatic heterocycle having 1 to 4 N, O and/or S atoms, which may be unsubstituted or mono-, di- or trisubstituted by Hal, A, NHA, $NA_2$, OA, COOA, CN, —$(CH_2)_p$—Ar, —$(CH_2)_t$—OH, —$(CH_2)_p$-$Het^1$ or carbonyl oxygen (=O).

Het particularly preferably denotes a monocyclic saturated or aromatic heterocycle having 1 to 3 N and/or O atoms, which may be unsubstituted or mono-, di- or trisubstituted by Hal, A, NHA, $NA_2$, COOA, benzyl, —$(CH_2)_t$—OH or —$(CH_2)_p$-$Het^1$; where $Het^1$ preferably denotes an unsubstituted monocyclic saturated or aromatic heterocycle having 1 to 3 N and/or O atoms, or

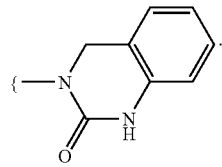

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4oxazinyl, furthermore preferably 1,3-benzodioxol-5-yl, 1,4-benzodioxan-6-yl, 2,1,3-benzothiadiazol4- or -5-yl or 2,1,3-benzoxadiazol-5-yl.

The heterocyclic radicals may also be partially or fully hydrogenated.

Het may thus also denote, for example, 2,3-dihydro-2-, -3-, 4- or -5-furyl, 2,5-dihydro-2-, -3-, 4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-di-hydro-1-, -2-,-3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

In a further embodiment, Het particularly preferably denotes piperazinyl, piperidinyl, morpholinyl, pyrrolidinyl, pyridyl or furyl, which are unsubstituted or may be mono-, di- or trisubstituted by Hal, A, NHA, $NA_2$, COOA, benzyl, —$(CH_2)_t$—OH or —$(CH_2)_p$-$Het^1$, where $Het^1$ preferably denotes morpholinyl, pyrrolidinyl, pyridyl or

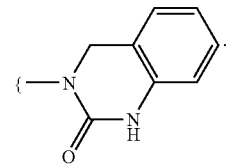

Irrespective of further substitutions, unsubstituted $Het^1$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het$^1$ may thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl, 2,3-dihydro-2-oxofuranyl or

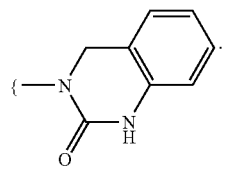

Irrespective of further substitutions by A, unsubstituted Het$^2$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

Het$^2$ preferably denotes an unsubstituted monocyclic aromatic heterocycle having 1-2 N, O and/or S atoms.

Irrespective of further substitutions by A, unsubstituted Het$^3$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het$^3$ may thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl or also 3,4-dihydro-2H-1,5-benzodioxepin-6- or -7-yl, furthermore preferably 2,3-dihydrobenzofuranyl.

Het$^4$ preferably denotes a monocyclic saturated or aromatic heterocycle having 1 to 3 N, O and/or S atoms, which may be unsubstituted or mono-, di- or trisubstituted by A, $CONH_2$, CONHA, $CONA_2$ or Ar$^2$, where Ar$^2$ preferably denotes phenyl which is unsubstituted or mono-, di- or trisubstituted by A.

Het$^4$ particularly preferably denotes pyridyl, benzo-1,2,5-thiadiazol-5-yl, piperazine, thiazole or imidazole, each of which is unsubstituted or mono-substituted by CONHA, A and/or Ar$^2$, where Ar$^2$ preferably denotes phenyl which is unsubstituted or mono-, di- or trisubstituted by A.

In the meaning of Ar$^1$, piperazinediyl preferably denotes piperazine-1,4-diyl. Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above.

Some preferred groups of compounds may be expressed by the following sub-formulae Ia to Ig, which conform to the formula I and in which the radicals not designated in greater detail have the meaning indicated for the formula I, but in which in Ia $R^1$ denotes A, OH, $NH_2$, $-(CH_2)_m-Ar$ or $-(CH_2)_m-Het^2$,
 Ar denotes phenyl which is unsubstituted or mono-, di- or trisubstituted by Hal, A, OA, COOH or COOA,
 m denotes 0;
in Ib $R^4$ denotes $-(CH_2)_s-(Ar^1)_n-Y-R^6$,
 s denotes 0 or 1,
 n denotes 1,
 $Ar^1$ denotes phenylene,
 $R^6$ denotes $Het^4$,
 Y denotes O,
 $Het^4$ denotes pyridyl which is unsubstituted or monosubstituted by CONHA,
 or benzo-1,2,5-thiadiazol-5-yl;
in Ic $R^4$ denotes $-(CH_2)_s-(Ar^1)_n-Y-R^6$,
 s denotes 1,
 n denotes 0,
 Y denotes $(CH_2)_q$,
 q denotes 0,
 $R^6$ denotes $Het^4$,
 $Het^4$ denotes pyridyl, benzo-1,2,5-thiadiazol-5-yl, thiazole, 1,2,3-triazole, thienyl or furyl, each of which is unsubstituted or monosubstituted by CONHA, A and/or $Ar^2$,
 $Ar^2$ denotes phenyl which is unsubstituted or mono-, di- or trisubstituted by A;
in Id $R^4$ denotes $-(CH_2)_s-(Ar^1)_n-Y-R^6$,
 s denotes 0,
 n denotes 0,
 Y denotes $(CH_2)_q$,
 q denotes 0,
 $R^6$ denotes $-(CH_2)_r-NH_2$, $-(CH_2)_r-NHA$ or $-(CH_2)_r-NA_2$,
 r denotes 1, 2, 3 or 4;
in Ie $R^4$ denotes $-(CH_2)_s-(Ar^1)_n-Y-R^6$,
 s denotes 0,
 n denotes 1,
 $Ar^1$ denotes phenylene,
 Y denotes O, $(CH_2)_q$ or NH,
 $R^6$ denotes $-(CH_2)_rNH_2$, $-(CH_2)_r-NHA$ or $-(CH_2)_r-NA_2$,
 q denotes 0, 1, 2, 3 or 4,
 r denotes 0, 1, 2, 3 or 4;
in If $R^4$ denotes $-(CH_2)_s-(Ar^1)_n-Y-R^6$,
 s denotes 1, 2, 3 or 4,
 n denotes 0,
 Y denotes $(CH_2)_q$,
 q denotes 0,
 $R^6$ denotes $Het^4$,
 $Het^4$ denotes a monocyclic saturated heterocycle having 1 to 2 N and/or O atoms, which may be unsubstituted or mono- or disubstituted by A;
in Ig $R^1$ denotes A, OH, $NH_2$, $-(CH_2)_m-Ar$,
 m denotes 0,
 Ar denotes phenyl which is unsubstituted or mono-, di- or trisubstituted by Hal, A, OA, COOH or COOA,
 $R^2$ if X=N is absent or if X=C denotes CN,
 $R^3$ denotes H, A, $-S-A$, phenyl or $-(CH_2)_p$-Het;
in Ih $R^1$ denotes A, OH, $NH_2$, $-(CH_2)_m-Ar$,
 m denotes 0,
 Ar denotes phenyl which is unsubstituted or mono-, di- or trisubstituted by Hal, A, OA, COOH or COOA,
 $R^2$ if X=N is absent or if X=C denotes CN,
 $R^3$ denotes H, A, $-S-A$, phenyl or $-(CH_2)_p$-Het,
 $R^4$ denotes $-(CH_2)_s-(Ar^1)_n-Y-R^6$,
 s denotes 0,
 n denotes 0,
 Y denotes $(CH_2)_q$,
 q denotes 0,
 $R^6$ denotes $-(CH_2)_r-NH_2$, $-(CH_2)_r-NHA$ or $-(CH_2)_r-NA_2$,
 r denotes 1, 2, 3 or 4;
in Ii $R^4$ denotes $-(CH_2)_s-(Ar^1)_n-Y-R^6$,
 s denotes 0,
 n denotes 1,
 Y denotes $(CH_2)_q$,
 q denotes 0,
 $R^6$ denotes $-(CH_2)_r-NH_2$, $-(CH_2)_r-NHA$ or $-(CH_2)_r-NA_2$,
 r denotes 0;
in Ij $R^4$ denotes $-(CH_2)_s-(Ar^1)_n-Y-R^6$,
 s denotes 0,
 n denotes 0 or 1,
 Y denotes $(CH_2)_q$,
 q denotes 0,
 $R^6$ denotes $-(CH_2)_r-NH_2$, $-(CH_2)_r-NHA$ or $-(CH_2)_r-NA_2$,
 r denotes 0, 1, 2, 3 or 4;
in Ik $R^4$ denotes $-(CH_2)_s-(Ar^1)_n-Y-R^6$,
 s denotes 0,
 n denotes 0 or 1,
 Y denotes $(CH_2)_q$,
 $R^6$ denotes $-(CH_2)_r-NH_2$, $-(CH_2)_r-NHA$ or $-(CH_2)_r-NA_2$,
 $Ar^1$ denotes phenylene,
 Y denotes O, $(CH_2)_q$ or NH,
 q denotes 0, 1, 2, 3 or 4,
 r denotes 0, 1, 2, 3 or 4;
in Il $R^1$ denotes A, OH, $NH_2$, $-(CH_2)_m-Ar$,
 m denotes 0,
 Ar denotes phenyl which is unsubstituted or mono-, di- or trisubstituted by Hal, A, OA, COOH or COOA,
 $R^2$ if X=N is absent or if X=C denotes CN,
 $R^3$ denotes H, A, $-S-A$, phenyl or $-(CH_2)_p$-Het,
 $R^4$ denotes $-(CH_2)_s-(Ar^1)_n-Y-R^6$,
 s denotes 0,
 n denotes 0 or 1,
 Y denotes $(CH_2)_q$,
 $R^6$ denotes $-(CH_2)_r-NH_2$, $-(CH_2)_r-NHA$ or $-(CH_2)_r-NA_2$,
 $Ar^1$ denotes phenylene,
 Y denotes O, $(CH_2)_q$ or NH,
 q denotes 0, 1, 2, 3 or 4,
 r denotes 0, 1, 2, 3 or 4;
in Im $R^1$ denotes A, OH, $NH_2$, $-(CH_2)_m-Ar$,
 m denotes 0,
 Ar denotes phenyl which is unsubstituted or mono-, di- or trisubstituted by Hal, A, OA, COOH or COOA,
 $R^2$ if X=N is absent or if X=C denotes CN,
 $R^3$ denotes H, A, $-S-A$, phenyl or $-(CH_2)_p$-Het,
 $R^4$ denotes $-(CH_2)_s-(Ar^1)_n-Y-R^6$,
 s denotes 0,
 n denotes 1,
 $Ar^1$ denotes phenylene,
 $R^6$ denotes $Het^4$,
 Y denotes O,
 $Het^4$ denotes pyridyl which is unsubstituted or monosubstituted by CONHA,
 or benzo-1,2,5-thiadiazol-5-yl;

in In R$^4$ denotes —(CH$_2$)$_s$—(Ar$^1$)$_n$—Y—R$^6$,
s denotes 0 or 1,
n denotes 0 or 1,
Y denotes O or (CH$_2$)$_q$,
q denotes 0,
R$^6$ denotes Het$^4$,
Het$^4$ denotes pyridyl, benzo-1,2,5-thiadiazol-5-yl, thiazole, 1,2,3-triazole, thienyl or furyl, each of which is unsubstituted or monosubstituted by CONHA, A and/or Ar$^2$,
Ar$^2$ denotes phenyl which is unsubstituted or mono-, di- or trisubstituted by A,
Ar$^1$ denotes phenylene;
in Io Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —(CH$_2$)$_t$—OH or —(CH$_2$)$_p$-Het$^1$,
Het$^1$ denotes an unsubstituted monocyclic saturated or aromatic heterocycle having 1 to 3 N and/or O atoms, or

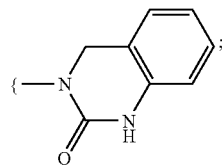

in Ip Het denotes piperazinyl, piperidinyl, morpholinyl, pyrrolidinyl, pyridyl or furyl, which are unsubstituted or may be mono-, di- or trisubstituted by Hal, A, NHA, NA$_2$, COOA, benzyl, —(CH$_2$)$_t$—OH or —(CH$_2$)$_p$-Het$^1$,
Het$^1$ denotes morpholinyl, pyrrolidinyl, pyridyl or

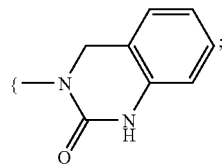

in Iq R$^4$ denotes —(CH$_2$)$_s$—(Ar$^1$)$_n$—Y—R$^6$,
s denotes 0 or 1,
n denotes 0 or 1,
Y denotes O, (CH$_2$)$_q$ or NH,
Ar$^1$ denotes phenylene,
q denotes 0, 1, 2, 3 or 4,
R$^6$ denotes Het$^4$, —(CH$_2$)$_r$—NH$_2$, —(CH$_2$)$_r$—NHA or —(CH$_2$)$_r$—NA$_2$,
r denotes 0, 1, 2, 3 or 4,
Het$^4$ denotes pyridyl, benzo-1,2,5-thiadiazol-5-yl, thiazole, 1,2,3-triazole, thienyl or furyl, each of which is unsubstituted or monosubstituted by CONHA, A and/or Ar$^2$,
Ar2 denotes phenyl which is unsubstituted or mono-, di- or trisubstituted by A;
in Ir R$^1$ denotes A, OH, NH$_2$, —(CH$_2$)$_m$—Ar,
m denotes 0,
Ar denotes phenyl which is unsubstituted or mono-, di- or trisubstituted by Hal, A, OA, COOH or COOA, R$^2$ if X=N is absent or if X=C denotes CN,
R$^3$ denotes H, A, —S-A, phenyl or —(CH$_2$)$_p$-Het,
Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —(CH$_2$)$_t$—OH or —(CH$_2$)$_p$-Het$^1$,
Het$^1$ denotes an unsubstituted monocyclic saturated or aromatic heterocycle having 1 to 2 N and/or O atoms, or

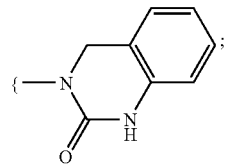

in Is R$^4$ denotes —(CH$_2$)$_s$—(Ar$^1$)$_n$—Y—R$^6$,
s denotes 0, 1, 2, 3 or 4,
n denotes 0 or 1,
Y denotes O or(CH$_2$)$_q$,
Ar$^1$ denotes phenylene,
q denotes 0,
R$^6$ denotes Het$^4$, —(CH$_2$)$_r$—NH$_2$, —(CH$_2$)$_r$—NHA or —(CH$_2$)$_r$—NA$_2$,
r denotes 0, 1, 2, 3 or 4,
Het$^4$ denotes a monocyclic saturated or aromatic heterocycle having 1 to 3 N, O and/or S atoms, which may be unsubstituted or mono-, di- or trisubstituted by A, CONH$_2$, CONHA, CONA$_2$ or Ar$^2$,
Ar$^2$ denotes phenyl which is unsubstituted or mono-, di- or trisubstituted by A;
in It Het$^4$ denotes pyridyl, benzo-1,2,5-thiadiazol-5-yl, piperazine, thiazole or imidazole, each of which is unsubstituted or monosubstituted by CONHA, A and/or Ar$^2$;
in Iu R$^4$ denotes 4-(pyridin-4-yloxy)phenyl, 4-(pyridin-4-yloxy)-phenylmethyl or 4-(benzo-1,2,5-thiadiazol-5-yloxy)-phenyl, where the pyridine radical may be substituted by CONHCH$_3$;
in Iv Het$^1$ denotes an unsubstituted monocyclic saturated or aromatic heterocycle having 1 to 2 N and/or O atoms, or

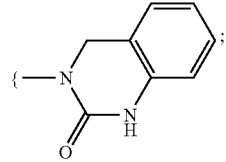

in Iw Het$^1$ denotes morpholinyl, pyrrolidinyl, piperidinyl, pyridyl or

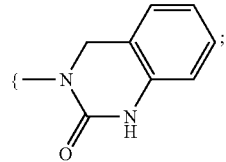

in Ix Het² denotes an unsubstituted monocyclic aromatic heterocycle having 1-2 N, O and/or S atoms;
in Iy R¹ denotes A, OH, NH₂, —(CH₂)ₘ—Ar or —(CH₂)ₘ-Het²,
m denotes 0,
Ar denotes phenyl which is unsubstituted or mono-, di- or trisubstituted by Hal, A, OA, COOH or COOA,
R² if X=N is absent or if X=C denotes H, CN, COOA or phenyl,
R³ denotes H, A, —S-A, phenyl, NH-benzyl, —(CH₂)ₚ-Het, NH—(CH₂)ₚ-Het, NA₂, NH-alkylene-NA₂ or NA-alkylene-NA₂;
in Iz R² if X=N is absent or if X=C denotes H, CN, (CH₂)ₒAr'', (CH₂)ₒCOOA or SO₂A,
Ar'' denotes phenyl which is unsubstituted or mono-, di- or trisubstituted by Hal or OA,
o denotes 0 or 1;
in Iab R¹ denotes A, OH, NH₂, —(CH₂)ₘ—Ar' or —(CH₂)ₘ-Het²,
Ar' denotes phenyl which is unsubstituted or mono-, di- or trisubstituted by Hal, OA, A or COOA,
m denotes 0,
Het² denotes thienyl, furyl, imidazolyl, pyrrolyl, thiazolyl or pyridyl;
in Iac X denotes C or N,
B denotes N, CH or C—CN,
R denotes A, OH, NH₂, —(CH₂)ₘ—Ar' or —(CH₂)ₘ-Het²,
Ar' denotes phenyl which is unsubstituted or mono-, di- or trisubstituted by Hal, OA, A or COOA,
m denotes 0,
Het² denotes thienyl, furyl, imidazolyl, pyrrolyl, thiazolyl or pyridyl,
R² if X=N is absent or if X=C denotes H, CN, (CH₂)ₒAr'', (CH₂)ₒCOOA or SO₂A,
Ar'' denotes phenyl which is unsubstituted or mono-, di- or trisubstituted by Hal or OA,
o denotes 0 or 1,
R³ denotes H, A, —S-A, phenyl, NH-benzyl, —(CH₂)ₚ-Het, NH—(CH₂)ₚ-Het, NA₂, NH-alkylene-NA₂ or NA-alkylene-NA₂,
Het denotes piperazinyl, piperidinyl, morpholinyl, pyrrolidinyl, pyridyl or furyl, which are unsubstituted or may be mono-, di- or trisubstituted by Hal, A, NHA, NA₂, COOA, benzyl, —(CH₂)ₜ—OH or —(CH₂)ₚ-Het¹,
Het¹ denotes morpholinyl, pyrrolidinyl, pyridyl or

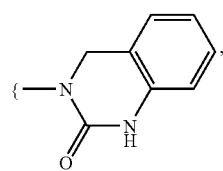

R⁴ denotes —(CH₂)ₛ—(Ar¹)ₙ—Y—R⁶,
Y denotes O or (CH₂)q,
R⁵ denotes H or CH₃,

R⁴ and R⁵ together also denote

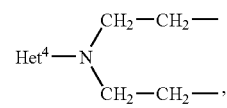

R⁶ denotes Het⁴, —(CH₂)ᵣ—NH₂, —(CH₂)ᵣ—NHA or —(CH₂)ᵣ—NA₂,
Het⁴ denotes pyridyl, benzo-1,2,5-thiadiazol-5-yl, piperazine, thiazole or imidazole, each of which is unsubstituted or monosubstituted by CON HA, A and/or Ar²,
Ar¹ denotes phenylene or piperazinediyl,
Ar² denotes phenyl which is unsubstituted or mono-, di- or trisubstituted by A,
R⁷, R⁸, R⁹, R¹⁰ each, independently of one another, denote H, A or —(CH₂)ₚ—Ar,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if X=C,
R¹ and R² together may also denote —(CH₂)₄— or
R² and R³ together may also denote —(CHR⁷—NR⁸—CHR⁹—CHR¹⁰)—,
and, if Ar¹ denotes piperazinediyl, R⁶ may also denote H or alkyl having 1-6 C atoms;
in Iad X denotes C or N,
B denotes N, CH or C—CN,
R¹ denotes A, OH, NH₂, —(CH₂)ₘ—Ar' or —(CH₂)ₘ-Het²,
Ar' denotes phenyl which is unsubstituted or mono-, di- or trisubstituted by Hal, OA, A or COOA,
m denotes 0,
Het² denotes an unsubstituted monocyclic aromatic heterocycle having 1-2 N, O and/or S atoms,
R² if X=N is absent or if X=C denotes H, CN, (CH₂)ₒAr'', (CH₂)ₒCOOA or SO₂A,
Ar'' denotes phenyl which is unsubstituted or mono-, di- or trisubstituted by Hal or OA,
o denotes 0 or 1,
R³ denotes H, A, —S-A, phenyl, NH-benzyl, —(CH₂)ₚ-Het, NH—(CH₂)ₚ-Het, NA₂, NH-alkylene-NA₂ or NA-alkylene-NA₂,
Het denotes a monocyclic saturated or aromatic heterocycle having 1 to 3 N and/or O atoms, which may be unsubstituted or mono-, di- or trisubstituted by Hal, A, NHA, NA₂, COOA, benzyl, —(CH₂)ₜ—OH or —(CH₂)ₚ-Het¹,
Het¹ denotes morpholinyl, pyrrolidinyl, pyridyl or

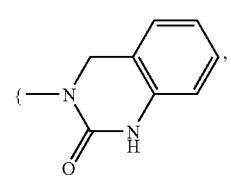

$R^4$ denotes —(CH$_2$)$_s$—(Ar$^1$)$_n$—Y—R$^6$,
Y denotes O or (CH$_2$)$_q$,
$R^5$ denotes H or CH$_3$,
$R^4$ and $R^5$ together also denote

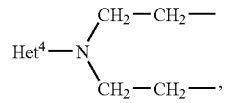

$R^6$ denotes Het$^4$, —(CH$_2$)$_r$—NH$_2$, —(CH$_2$)$_r$—NHA or —(CH$_2$)$_r$—NA$_2$,
Het$^4$ denotes a monocyclic saturated or aromatic heterocycle having 1 to 3 N, O and/or S atoms, which may be unsubstituted or mono-, di- or trisubstituted by A, CONH$_2$, CONHA, CONA$_2$ or Ar$^2$,
Ar$^1$ denotes phenylene or piperazinediyl,
Ar$^2$ denotes phenyl which is unsubstituted or mono-, di- or trisubstituted by A,
$R^7$, $R^8$, $R^9$, $R^{10}$ each, independently of one another, denote H, A or —(CH$_2$)$_p$—Ar,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if X=C,
$R^1$ and $R^2$ together may also denote —(CH$_2$)$_4$— or
$R^2$ and $R^3$ together may also denote —(CHR$^7$—NR$^8$—CHR$^9$—CHR$^{10}$)—,
and, if Ar$^1$ denotes piperazinediyl, R$^6$ may also denote H or alkyl having 1-6 C atoms;
in Iae X denotes N,
B denotes N, CH or C—CN,
$R^1$ denotes NH$_2$,
$R^2$ is absent,
$R^3$ denotes H, A, —S-A, phenyl, NH-benzyl, —(CH$_2$)$_p$-Het, NH—(CH$_2$)$_p$-Het, NA$_2$, NH-alkylene-NA$_2$ or NA-alkylene-NA$_2$,
Het denotes piperazinyl, piperidinyl, morpholinyl, pyrrolidinyl, pyridyl or furyl, which are unsubstituted or may be mono-, di- or trisubstituted by Hal, A, NHA, NA$_2$, COOA, benzyl, —(CH$_2$)$_t$—OH or —(CH$_2$)$_p$-Het$^1$,
Het$^1$ denotes morpholinyl, pyrrolidinyl, pyridyl
or

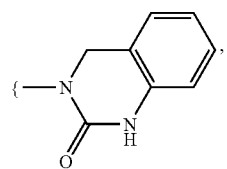

$R^4$ denotes —(CH$_2$)$_s$—(Ar$^1$)$_n$—Y—R$^6$,
Y denotes O or (CH$_2$)$_q$,
$R^5$ denotes H or CH$_3$,
$R^4$ and $R^5$ together also denote

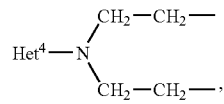

$R^6$ denotes Het$^4$, —(CH$_2$)$_r$—NH$_2$, —(CH$_2$)$_r$—NHA or —(CH$_2$)$_r$—NA$_2$,
Het$^4$ denotes pyridyl, benzo-1,2,5-thiadiazol-5-yl, piperazine, thiazole or imidazole, each of which is unsubstituted or monosubstituted by CONHA, A and/or Ar$^2$,
Ar$^1$ denotes phenylene or piperazinediyl,
Ar$^2$ denotes phenyl which is unsubstituted or mono-, di- or trisubstituted by A,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if Ar$^1$ denotes piperazinediyl, R$^6$ may also denote H or alkyl having 1-6 C atoms;
in Iaf X denotes N,
B denotes N, CH or C—CN,
$R^1$ denotes NH$_2$,
$R^2$ is absent,
$R^3$ denotes H, A, —S-A, phenyl, NH-benzyl, —(CH$_2$)$_p$-Het, NH—(CH$_2$)$_p$-Het, NA$_2$, NH-alkylene-NA$_2$ or NA-alkylene-NA$_2$,
Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —(CH$_2$)$_t$—OH or —(CH$_2$)$_p$-Het$^1$,
Het$^1$ denotes morpholinyl, pyrrolidinyl, pyridyl
or

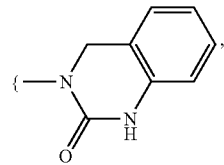

$R^4$ denotes —(CH$_2$)$_s$—(Ar$^1$)$_n$—Y—R$^6$,
Y denotes O or (CH$_2$)$_q$,
$R^5$ denotes H or CH$_3$,
$R^4$ and $R^5$ together also denote

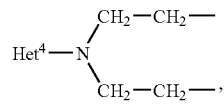

$R^6$ denotes Het$^4$, —(CH$_2$)$_r$—NH$_2$, —(CH$_2$)$_r$—NHA or —(CH$_2$)$_r$—NA$_2$,
Het$^4$ denotes a monocyclic saturated or aromatic heterocycle having 1 to 3 N, O and/or S atoms, which may be unsubstituted or mono-, di- or trisubstituted by A, $CONH_2$, CONHA, $CONA_2$ or $Ar^2$, $Ar^1$ denotes phenylene or piperazinediyl, $Ar^2$ denotes phenyl which is unsubstituted or mono-, di- or trisubstituted by A, A denotes alkyl having 1 to 10 C atoms, where, in addition, 1-7 H atoms may be replaced by F and/or chlorine, n denotes 0 or 1, p denotes 0, 1, 2, 3 or 4, q denotes 0, 1, 2, 3 or 4, r denotes 0, 1, 2, 3 or 4, s denotes 0, 1, 2, 3 or 4, t denotes 1, 2, 3 or 4, Hal denotes F, Cl, Br or I, and, if $Ar^1$ denotes piperazinediyl, $R^6$ may also denote H or alkyl having 1-6 C atoms;

and pharmaceutically usable derivatives, salts, solvates, tautomers, and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

If desired, the starting materials can also be formed in situ by not isolating them from the reaction mixture, but instead immediately converting them further into the compounds of the formula I.

Compounds of the formula I in which X denotes C can preferably be obtained by reacting compounds of the formula II with compounds of the formula IIIa, IIIb or IIIc.

The compounds of the formula II are novel, those of the formula IIIa, IIIb and IIIc are generally known.

The reaction is generally carried out in an inert solvent, optionally in the presence of an organic base, such as triethylamine, dimethylaniline, pyridine or quinoline. Depending on the conditions used, the reaction time is between a few minutes and 14 days, the reaction temperature is between about 0° and 180°, normally between 25° and 160°, particularly preferably between 60 and 160° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I in which X denotes N and $R^1$ denotes $NH_2$ can furthermore preferably be obtained by reacting compounds of the formula II with compounds of the formula IIId. The compounds of the formula IIId are generally known.

The reaction is generally carried out in an inert solvent and under conditions as indicated above.

Compounds of the formula I in which

X denotes N, $R^1$ denotes H, A, $-(CH_2)_m-Ar$ or $-(CH_2)_m-Het^2$, $R^3$ denotes —S-A, can furthermore preferably be obtained by reacting compounds of the formula II with compounds of the formula IIIe. The compounds of the formula IIId are generally known.

The reaction is generally carried out in an inert solvent and under conditions as indicated above.

It is furthermore possible to convert a compound of the formula I into another compound of the formula I by converting one or more radical(s) $R^1$, $R^2$ or $R^3$ into one or more different radicals $R^1$, $R^2$ or $R^3$, for example by a) converting an alkylsulfanyl group into an amine, b) reducing nitro groups to amino groups, for example by hydrogenation on Raney nickel or Pd/carbon in an inert solvent, such as methanol or ethanol, b) converting an ester group into a carboxyl group, c) converting an amino group into an alkylated amine by reductive amination and/or d) esterifying carboxyl groups by reaction with alcohols.

The conversion of an alkylsulfanyl group into an amine is carried out by reaction of the alkylsulfanyl compound with the corresponding amine in an inert solvent. Depending on the conditions used, the reaction time is between a few minutes and 14 days, the reaction temperature is between about 0° and 180°, normally between 25° and 160°, particularly preferably between 60 and 160° C.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or to the alcohol, or the reduction of a nitrile to the aldehyde or amine is carried out by methods as are known to the person skilled in the art and are described in standard works of organic chemistry.

Pharmaceutical Salts and other Forms

The said compounds according to the invention can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention also relates to the intermediate compounds of the formula I-1

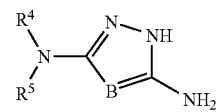

I-1 in which
B denotes N, CH or C—CN,
$R^4$ denotes —$(CH_2)_s$—$(Ar^1)_n$—Y—$R^6$,
$R^5$ denotes H or $CH_3$,
$R^4$ and $R^5$ together also denote $$Het^4-N\begin{matrix}CH_2-CH_2-\\ \\ CH_2-CH_2-\end{matrix},$$

$R^6$ denotes $Het^4$, —$(CH_2)_r$—$NH_2$, —$(CH_2)_r$—NHA or —$(CH_2)_r$—$NA_2$,
Y denotes O, S, $(CH_2)_q$ or NH,
$Ar^1$ denotes phenylene or piperazinediyl,
$Het^4$ denotes a mono- or bicyclic saturated, unsaturated or aromatic heterocycle having 1 to 4 N, O and/or S atoms, which may be unsubstituted or mono-, di- or trisubstituted by Hal, A, $CONH_2$, CONHA, $CONA_2$ or $Ar^2$,
$Ar^2$ denotes phenyl which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$ or $SO_2A$,
A denotes alkyl having 1 to 10 C atoms, where, in addition, 1-7 H atoms may be replaced by F and/or chlorine,
n denotes 0 or 1,
q denotes 0, 1, 2, 3 or 4,
r denotes 0, 1, 2, 3 or 4,
s denotes 0, 1, 2, 3 or 4,
Hal denotes F, Cl, Br or I,
and, if $Ar^1$ denotes piperazinediyl, $R^6$ may also denote H or alkyl having 1-6 C atoms, and solvates, salts and stereoisomers thereof, including mixtures thereof in all ratios.
Preference is given to the following compounds of the formula I-1 in which
B denotes N, CH or C—CN,
$R^4$ denotes —$(CH_2)_s$—$(Ar^1)_n$—Y—$R^6$,
Y denotes O or $(CH_2)_q$,
$R^5$ denotes H or $CH_3$,
$R^4$ and $R^5$ together also denote $$Het^4-N\begin{matrix}CH_2-CH_2-\\ \\ CH_2-CH_2-\end{matrix},$$

$R^6$ denotes $Het^4$, —$(CH_2)_r$—$NH_2$, —$(CH_2)_r$—NHA or —$(CH_2)_r$—$NA_2$,
$Het^4$ denotes pyridyl, benzo-1,2,5-thiadiazol-5-yl, piperazine, thiazole or imidazole, each of which is unsubstituted or monosubstituted by CONHA, A and/or $Ar^2$,
$Ar^1$ denotes phenylene or piperazinediyl,
$Ar^2$ denotes phenyl which is unsubstituted or mono-, di- or trisubstituted by A,
A denotes alkyl having 1 to 10 C atoms, where, in addition, 1-7 H atoms may be replaced by F and/or chlorine,
n denotes 0 or 1,
q denotes 0, 1, 2, 3 or 4,
r denotes 0, 1, 2, 3 or 4,
s denotes 0, 1, 2, 3 or 4,
Hal denotes F, Cl, Br or I,
and, if $Ar^1$ denotes piperazinediyl, $R^6$ may also denote H or alkyl having 1-6 C atoms, and salts, solvates and stereoisomers thereof, including mixtures thereof in all ratios.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
 (a) an effective amount of a compound of the formula I and/or pharmaceutically usable derivatives, solvates and stereoisomers thereof, including mixtures thereof in all ratios, and
 (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma. Also encompassed is the use of the compounds of the formula I and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of the compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use of the compounds according to the invention according to aspect 1 and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer. The present compounds inhibit tumour angiogenesis, thereby affecting the growth of tumours (J. Rak et al. *Cancer Research;* 55:4575-4580, 1995). The angiogenesis-inhibiting properties of the present compounds of the formula I are also suitable for the treatment of certain forms of blindness related to retinal neovascularisation.

The compounds of the formula I are also suitable for the treatment of certain bone pathologies, such as osteosarcoma, osteoarthritis and rickets, also known as oncogenic osteomalacia (Hasegawa et al., Skeletal Radiol. 28, pp. 41-45, 1999; Gerber et al., Nature Medicine, Vol. 5, No. 6, pp. 623-628, June 1999). Since VEGF directly promotes osteoclastic bone resorption through KDR/Flk-1 expressed in mature osteoclasts (FEBS Let. 473:161-164 (2000); Endocrinology, 141:

1667 (2000)), the present compounds are also suitable for the treatment and prevention of conditions related to bone resorption, such as osteoporosis and Paget's disease.

The compounds can also be used for the reduction or prevention of tissue damage which occurs after cerebral ischaemic events, such as strokes, by reducing cerebral oedema, tissue damage and reperfusion injury following ischaemia (*Drug News Perspect* 11:265-270 (1998); *J. Clin. Invest.* 104:1613-1620 (1999)).

As explained, the signalling pathways are relevant for various disorders. Accordingly, by interacting with one or more of said signalling pathways, the compounds according to the invention are useful in the prevention and/or the treatment of disorders that are dependent on said signalling pathways.

The compounds according to the invention are preferably kinase modulators and more preferably kinase inhibitors. According to the invention, kinases include, but are not limited to, one or more Tie kinases, one or more VEGFR kinases, one or more PDGFR kinases, p38 kinase and/or SAPK2alpha.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to kinases selected from the group of the tyrosine kinases.

The tyrosine kinases are preferably TIE-2, VEGFR, PDGFR, FGFR and/or FLT/KDR.

Preference is given to the use of compounds of the formula I, and pharmaceutically usable derivatives, solvates and stereoisomers thereof, including mixtures thereof in all ratios, for the preparation of a medicament for the treatment of diseases which are influenced by inhibition of tyrosine kinases by the compounds according to aspect 1.

Particular preference is given to the use for the preparation of a medicament for the treatment of diseases which are influenced by inhibition of TIE-2, VEGFR, PDGFR, FGFR and/or FLT/KDR by the compounds according to aspect 1.

Especial preference is given to the use for the treatment of a disease where the disease is a solid tumour.

The solid tumour is preferably selected from the group of the tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myelotic leukaemia, chronic myelotic leukaemia, acute lymphatic leukaemia and/or chronic lymphatic leukaemia.

The invention furthermore relates to the use of the compounds of the formula I for the treatment of a disease in which angiogenesis is implicated.

The disease is preferably an ocular disease.

The invention furthermore relates to the use for the treatment of retinal vascularisation, diabetic retinopathy, age-induced macular degeneration and/or inflammatory diseases.

The inflammatory disease is preferably selected from the group consisting of rheumatoid arthritis, psoriasis, contact dermatitis and delayed hypersensitivity reaction.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated. For example, in the case of bone conditions, combinations that would be favourable include those with antiresorptive bisphosphonates, such as alendronate and risedronate, integrin blockers (as defined further below), such as αvβ3 antagonists, conjugated oestrogens used in hormone replacement therapy, such as Prempro®, Premarin® and Endometrion®; selective oestrogen receptor modulators (SERMs), such as raloxifene, droloxifene, CP-336, 156 (Pfizer) and lasofoxifene, cathepsin K inhibitors, and ATP proton pump inhibitors.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibiting VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646. "Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)Platinum, benzylguanine, glufosfamide, GPX100, (trans,trans,trans)bis-mu-(hexane-1,6-diamine)mu-[diamine-Platinum(II)]bis[diamine(chloro)Platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyidaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2- (6H)propanamine, 1-amino-9-ethyl-5-fluoro-2,3-dihydro-9-hydroxy4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)-ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-to[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimeterxate, fludarabine, capecitabine, galocitabine, cytarabine ocfosfate, fosteabine sodium hydrate, raltitrexed, paltitrexid, emitefur, tiazofurin, decitabine, nolatrexed, pemeterxed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometerxol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The invention furthermore relates to the use of the compounds of the formula I for the preparation of a medicament for the treatment of diseases, where the disease is characterised by disturbed angiogenesis. The disease is preferably cancer diseases.

The disturbed angiogenesis preferably results from disturbed VEGFR-1, VEGFR-2 and/or VEGFR-3 activity.

Particular preference is therefore also given to the use of the compounds according to the invention for the preparation of a medicament for the inhibition of VEGFR-2 activity.

Assays

The compounds according to the invention described in the examples were tested by the assays described below and were found to have kinase inhibitory activity. Other assays are known from the literature and could readily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

In general, compounds according to the invention are to be regarded as suitable kinase-modulators and especially suitable kinase inhibitors according to the invention if they show an effect or an activity to one or more kinases, preferably to one or more Raf kinases, which is preferably, determined as $IC_{50}$ value, in the region of 100 µmol or below, preferably 10 µmol or below, more preferably in the region of 3 µmol or below, even more preferably in the region of 1 µmol or below and most preferably in the nanomolar range. Especially preferred for use according to the invention are kinase inhibitors as defined above/below which show an activity, determined as $IC_{50}$ value, to one or more Raf kinases in the region of 0.5 µmol or below and especially in the region of 0.1 µmol or below. In many cases, an $IC_{50}$ value at the lower end of the given ranges is advantageous and in some cases it is highly desirable that the $IC_{50}$ value is as small as possible or the $IC_{50}$ values are as small as possible, but in general $IC_{50}$ values which are between the above given upper limits and a lower limit in the region of 0.0001 µmol, 0.001 µmol, 0.01 µmol or even above 0.1 µmol are sufficient to indicate the desired pharmaceutical activity. However, the activities measured can vary depending on the respective testing system or assay chosen.

Alternatively, the advantageous biological activity of the compounds according to the invention can easily be demonstrated in in vitro assays, such as in vitro proliferation assays or in vitro growth assays. Suitable in vitro assays are known in the art, for example from the literature cited herein and the references cited in the literature, or can be performed as described below, or can be developed and/or performed in an analogous manner thereto.

As an example for an in vitro growth assay, human tumour cell lines, for example HCT116, DLD-1 or MiaPaCa, containing mutated K-Ras genes can be used in standard proliferation assays, for example for anchorage-dependent growth on plastic or anchorage-independent growth in soft agar. Human tumour cell lines are commercially available, for example from ATCC (Rockville Md.), and can be cultured by methods known in the art, for example in RPMI with 10% of heat-deactivated foetal bovine serum and 200 mM glutamine. Cell culture media, foetal bovine serum and additives are commercially available, for example from Invitrogen/Gibco/BRL (Karlsruhe, Germany) and/or QRH Biosciences (Lenexa, KS). In a standard proliferation assay for anchorage-dependent growth, $3 \times 10^3$ cells can be seeded into 96-well tissue culture plates and allowed to attach, for example overnight at 37° C. in a 5% $CO_2$ incubator. Compounds can be titrated in media in dilution series and added to 96-well cell cultures. Cells are allowed to grow, for example for 1 to 5 days, typically with feeding of fresh compound containing media at about half of the time of the growing period, for example on day 3 if the cells are allowed to grow for 5 days. Proliferation can be monitored by methods known in the art, such as measurement of metabolic activity, for example with standard XTT colorimetric assay (Boehringer Mannheim) measured by standard ELISA plate reader at OD 490/560, by measuring $^3$H-thymidine incorporation into DNA following an 8 h culture with 1 μCu $^3$H-thymidine, harvesting the cells onto glass fibre mats using a cell harvester and measuring $^3$H-thymidine incorporation by liquid scintillation counting, or by staining techniques, such as Crystal Violet staining. Other suitable cellular assay systems are known in the art.

Alternatively, for anchorage-independent cell growth, cells can be plated at $1 \times 10^3$ to $3 \times 10^3$ in 0.4% of Seaplaque agarose in RPMI complete media, overlaying a bottom layer containing only 0.64% agar in RPMI complete media, for example in 24-well tissue culture plates. Complete media plus dilution series of compounds can be added to wells and incubated, for example at 37° C. in a 5% $CO_2$ incubator for a sufficient time, for example 10-14 days, preferably with repeated feedings of fresh media containing compound, typically at 3-4 day intervals. Colony formation and total cell mass can be monitored, average colony size and number of colonies can be quantified by methods known in the art, for example using image capture technology and image analysis software. Image capture technology and image analysis software, such as Image Pro Plus or media Cybernetics.

VEGF Receptor Kinase Assay

VEGF receptor kinase activity is measured by incorporation of radiolabelled phosphate into 4:1 polyglutamic acid/tyrosine substrate (pEY). The phosphorylated pEY product is trapped on a filter membrane and the incorporation of radiolabelled phosphate is quantified by scintillation counting.

Materials

VEGF Receptor Kinase

The intracellular tyrosine kinase domains of human KDR (Terman, B. I. et al. Oncogene (1991) Vol. 6, pp. 1677-1683.) and Flt-1 (Shibuya, M. et al. Oncogene (1990) Vol. 5, pp. 519-524) were cloned as glutathione S-transferase (GST) gene fusion proteins. This was accomplished by cloning the cytoplasmic domain of the KDR kinase as an in frame fusion at the carboxyl terminus of the GST gene. Soluble recombinant GST-kinase domain fusion proteins were expressed in *Spodoptera frugiperda* (Sf21)insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% of Triton X-100, 10% of glycerol, 10 mg/ml each of leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% of Triton X-100, 10% glycerol, 10 mg/ml each of leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% of Triton X-100, 50% of glycerol, 10 mg/ml each of leupeptin, pepstatin and aprotinin and 1 mM phenylmethylsulfonyl fluoride.

10× Reaction Buffer 200 mM Tris, pH 7.4, 1.0 M NaCl, 50 mM $MnCl_2$, 10 mM DTT and 5 mg/ml of bovine serum albumin [BSA] (Sigma).

Enzyme Dilution Buffer 50 mM Tris, pH 7.4, 0.1 M NaCl, 1 mM DTT, 10% of glycerol, 100 mg/ml of BSA.

10× Substrate

750 μg/ml poly(glutamic acid/tyrosine; 4:1) (Sigma).

Stop Solution

30% of trichloroacetic acid, 0.2 M sodium pyrophosphate (both Fisher).

Wash Solution

15% of trichloroacetic acid, 0.2 M sodium pyrophosphate.

Filter Plates

Millipore #MAFC NOB, GF/C glass-fibre 96-well plate.

Method A—Protein Purification

1. Sf21 cells were infected with recombinant virus at a multiplicity of infection of 5 virus particles/cell and grown at 27° C. for 48 hours.
2. All steps were performed at 4° C. Infected cells were harvested by centrifugation at 1000×g and lysed at 4° C. for 30 minutes with ⅒ volume of lysis buffer followed by centrifugation at 100000×g for 1 hour. The supernatant was then passed over a glutathione Sepharose column (Pharmacia) equilibrated with lysis buffer and washed with 5 volumes of the same buffer followed by 5 volumes of wash buffer. Recombinant GST-KDR protein was eluted with wash buffer/10 mM reduced glutathione (Sigma) and dialysed against dialysis buffer.

Method B—VEGF Receptor Kinase Assay

1. Add 5 μl of inhibitor or control to the assay in 50% DMSO.
2. Add 35 μl of reaction mixture containing 5 μl of 10× reaction buffer, 5 μl of 25 mM ATP/10 μCi[$^{33}$P]ATP (Amersham) and 5 μl of 10× substrate.
3. Start the reaction by the addition of 10 μl of KDR (25 nM) in enzyme dilution buffer.
4. Mix and incubate at room temperature for 15 minutes.
5. Stop the reaction by the addition of 50 μl of stop solution.
6. Incubate at 4° C. for 15 minutes.
7. Transfer a 90 μl aliquot to filter plate.
8. Aspirate and wash 3 times with wash solution.
9. Add 30 μl of scintillation cocktail, seal plate and count in a Wallace Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are obtained from Clonetics Corp. Cells are obtained in endothelial growth medium (EGM; Clonetics) and are used for mitogenic assays at passages 3-7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) foetal bovine serum (Clonetics).

Test Compounds

Working stock solutions of test compounds are diluted serially in 100% dimethyl sulfoxide (DMSO) to 400 times greater than their desired final concentrations. Final dilutions to 1× concentration are made in assay medium immediately prior to addition to cells.

10× Growth Factors

Solutions of human VEGF 165 (500 ng/ml; R&D Systems) and bFGF (10 ng/ml; R&D Systems) are prepared in assay medium.

10× [$^3$H]Thymidine

[Methyl-$^3$H]thymidine (20 Ci/mmol; Dupont-NEN) is diluted to 80 µCi/ml in low-glucose DMEM medium.

Cell Wash Medium

Hank's balanced salt solution (Mediatech) containing 1 mg/ml of bovine serum albumin (Boehringer-Mannheim).

Cell Lysis Solution

1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cell growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10× VEGF solution or 10×bFGF solution. Cells are then incubated at 37° C./5% $CO_2$.

Method 4

After 24 hours in the presence of growth factors, 10× [$^3$H]thymidine (10 µl/well) is added.

Method 5

Three days after addition of [$^3$H]thymidine, medium is removed by aspiration, and cells are washed twice with cell wash medium (400 µl/well followed by 200 µl/well). The washed, adherent cells are then solubilised by addition of cell lysis solution (100 µl/well) and warming at 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I are inhibitors of VEGF and are thus suitable for the inhibition of angiogenesis, such as in the treatment of ocular diseases, for example diabetic retinopathy, and for the treatment of carcinomas, for example solid tumours. The present compounds inhibit VEGF-stimulated mitogenesis of human vascular endothelial cells in culture with IC50 values of 0.01-5.0 µM. These compounds also show selectivity over related tyrosine kinases (for example FGFR1 and the Src family; for relationship between Src kinases and VEGFR kinases, see Eliceiri et al., Molecular Cell, Vol. 4, pp. 915-924, December 1999).

The TIE-2 tests can be carried out, for example, analogously to the methods indicated in WO 02/44156.

The assay determines the inhibiting activity of the substances to be tested in the phosphorylation of the substrate poly(Glu, Tyr) by Tie-2 kinase in the presence of radioactive $^{33}$P-ATP. The phosphorylated substrate binds to the surface of a "flashplate" microtitre plate during the incubation time. After removal of the reaction mixture, the microtitre plate is washed a number of times and the radioactivity on its surface is subsequently measured. An inhibiting effect of the substances to be measured results in lower radioactivity compared with an undisturbed enzymatic reaction.

Above and below, all temperatures are indicated in ° C. In the following examples, "conventional work-up" means: water is added if necessary, the pH is adjusted, if necessary, to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$

APCI-MS (atmospheric pressure chemical ionisation—mass spectrometry) $(M+H)^+$.

Conditions for the determination of Rf values by HPLC:

Instrument: HP series 1100 with Agilent 1100 diode array detector (220 nm);

Column: Chromolith Speed Rod RP18e, 50-4.6 mm;

Flow rate: 2.4 ml/min;

Solvent ratio at the beginning:

solvent (S) A (water+0.01% of TFA): 80% solvent B (acetonitrile+0.01% of TFA): 20%

| Time table | | |
| --- | --- | --- |
| Time [min] | LM A | LM B |
| 0 | 80 | 20 |
| 2.8 | 0 | 100 |
| 3.3 | 0 | 100 |
| 3.4 | 80 | 20 |
| 3.6 | 80 | 20 |

EXAMPLES OF THE PREPARATION OF STARTING COMPOUNDS OF THE FORMULA I-1

Example 1

Preparation of N-[4-(pyridin-4-yloxy)phenyl]-4H-1,2,4-triazole-3,5-diamine ("1")

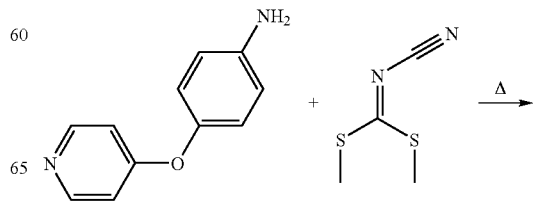

-continued

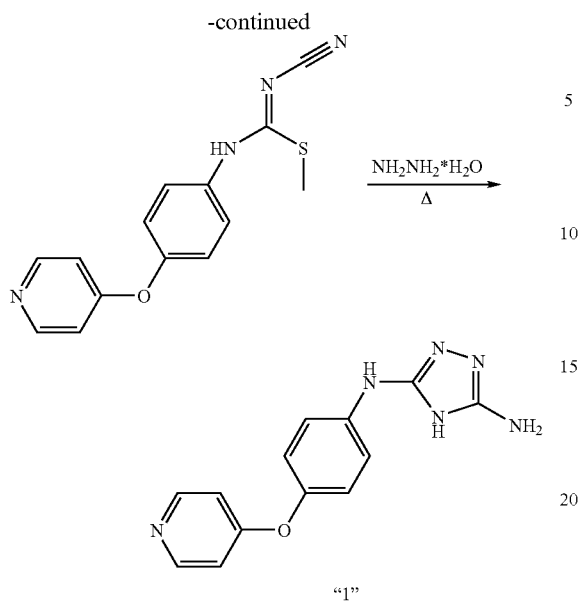

"1"

4-(Pyridin-4-yloxy)phenylamine (9.80 g, 52.6 mmol) is dissolved in ethanol (250 ml), dimethyl N-cyanodithioiminocarbonate (7.75 g, 52.6 mmol) is added, and the mixture is stirred under reflux for 2 days. The volatile constituents are completely removed under reduced pressure, the residue is again taken up in ethanol (250 ml), hydrazine hydrate (50 ml) is added, and the mixture is heated under reflux for 2 h. The product precipitated after cooling is filtered off, washed with diethyl ether and dried, giving 10.6 g (3.95 mmol, 75%) of "1", [M+H]$^+$ 269, $R_f$ 0.573 min.

The following compounds are obtained analogously
N-{4-[2-(N-methylaminocarbonyl)pyridin-4-yloxy]phenyl}-4H-1,2,4-triazole-3,5-diamine, [M+H]$^+$ 326, $R_f$ 0.884 min;
N-{3-[2-(N-methylaminocarbonyl)pyridin-4-yloxy]phenyl}-4H-1,2,4-triazole-3,5-diamine, $R_f$ 1.058 min;
N-[4-(pyridin-4-yloxy)phenylmethyl]-4H-1,2,4-triazole-3,5-diamine, [M+H]$^+$ 283, $R_f$ 0.510 min;
N-(5-methyl-2-phenyl-2H-1,2,3-triazol-4-ylmethyl)-4H-1,2,4-triazole-3,5-diamine, [M+H]$^+$ 271, $R_f$ 1.169 min;
N-(2-phenylthiazol-4-ylmethyl)-4H-1,2,4-triazole-3,5-diamine, [M+H]$_+$ 273, $R_f$ 1.168 min;
N-[4-(2-diethylaminoethoxy)phenyl]-4H-1,2,4-triazole-3,5-diamine, $R_f$ 0.462 min;
N-[4-(benzo-1,2,5-thiadiazol-5-yloxy)phenyl]-4H-1,2,4-triazole-3,5-diamine, [M+H]$^+$ 326, $R_f$ 1.310 min;
N-[4-(pyridin-4-ylsulfanyl)phenyl]-4H-1,2,4-triazole-3,5-diamine.

Example 2

Preparation of 5-amino-3-[4-(pyridin-4-yloxy)phenylamino]-1H-pyrazole-4-carbonitrile ("2")

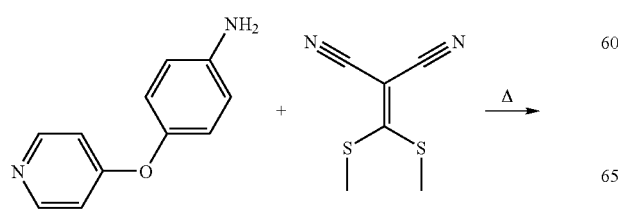

-continued

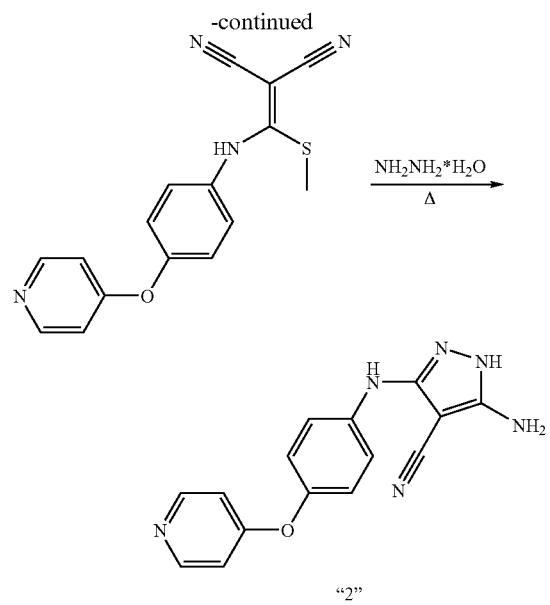

"2"

Analogously to Example 1, 4-(pyridin-4-yloxy)phenylamine (10.2 g, 54.7 mmol) is reacted firstly with 3,3-bis(methylthio)-2-cyanoaryl nitrile (9.33 g, 54.7 mmol) and then with hydrazine hydrate (50 ml). The product precipitated after cooling is filtered off, washed with diethyl ether and dried, giving 13.6 g (46.5 mmol, 85%) of a pale-brown substance ("2"), Rf 0.607 min;

Example 3

Preparation of N*3*-[4-(pyridin-4-yloxy)phenyl]-1H-pyrazole-3,5-diamine ("3")

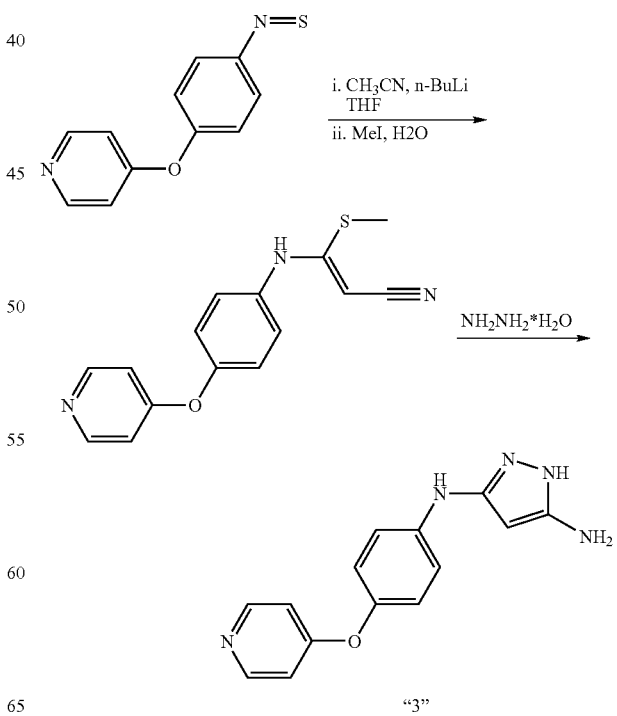

"3"

Acetonitrile (0.79 ml, 15.0 mmol) in THF (dry, 20 ml) is cooled to −78° C., n-BuLi solution in hexane (2.36 M, 5.10 ml, 12.0 mmol) is slowly added drop-wise, and the mixture is stirred at the same temperature for 30 min. The isothiocyanate (0.50 g, 2.19 mmol, dissolved in THF, 8 ml) is added at −78° C., during which a solid forms, which does not dissolve even on warming to 0° C. Ethyl acetate is added, and the organic phase is washed 3× with water. $CH_3I$ (0.29 ml, 2.5 mmol) is added to the aqueous phase, and the mixture is stirred at RT for 5 h. The solution is extracted 2× with ethyl acetate, dried, and the solvent is removed. "3" is obtained as colourless solid (0.34 g, 1.2 mmol, 55%), [M+H]⁺ 268, $R_f$ 0.544 min.

EXAMPLES OF THE PREPARATION OF COMPOUNDS OF THE FORMULA I

Example 4

Preparation of (7-phenyl-5-trifluoromethyl-1,2,4-triazolo[1,5-a]pyrimidin-2-yl)-[4-(pyridin-4-yloxy)phenyl]amine ("4")

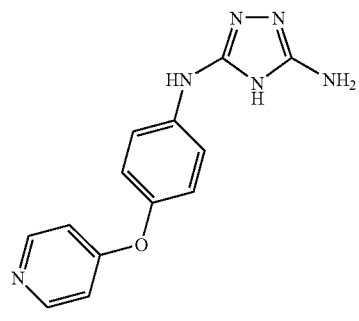

"1"

+

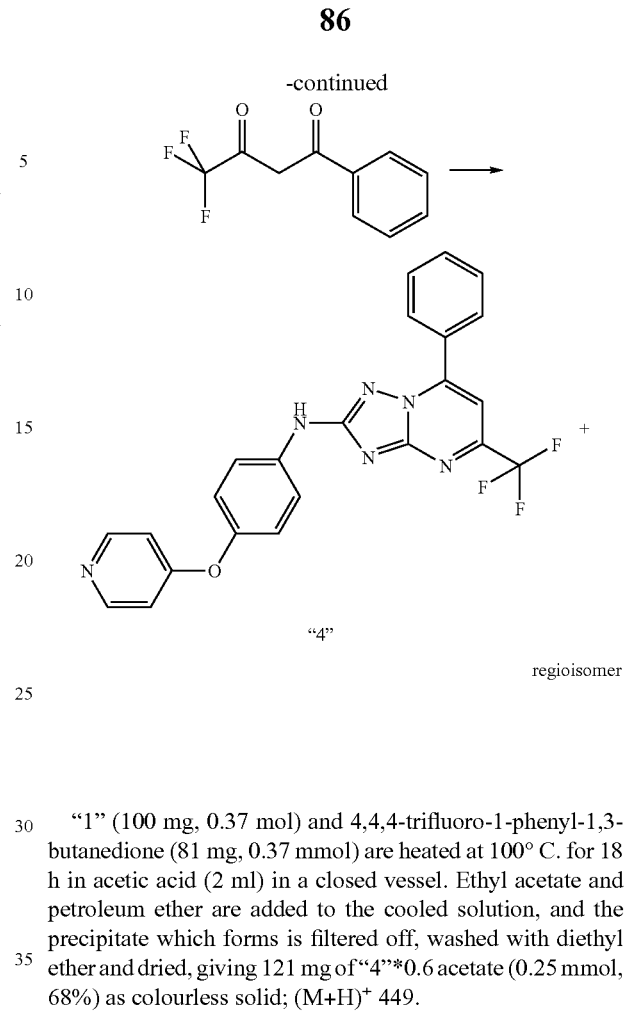

"1" (100 mg, 0.37 mol) and 4,4,4-trifluoro-1-phenyl-1,3-butanedione (81 mg, 0.37 mmol) are heated at 100° C. for 18 h in acetic acid (2 ml) in a closed vessel. Ethyl acetate and petroleum ether are added to the cooled solution, and the precipitate which forms is filtered off, washed with diethyl ether and dried, giving 121 mg of "4"*0.6 acetate (0.25 mmol, 68%) as colourless solid; (M+H)⁺ 449.

The following compounds are obtained analogously

| No. | Structure | (M + H)⁺ |
|---|---|---|
| 5 | 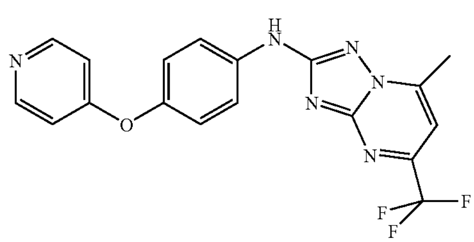 | 387 |
| 6 | 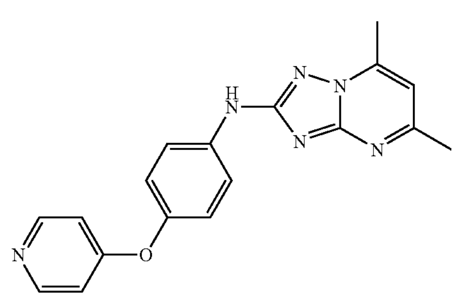 | 333 |

| No. | Structure | (M + H)+ |
|---|---|---|
| 7 | 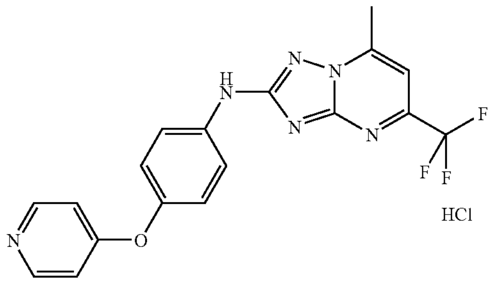 | 387 |
| 8 | 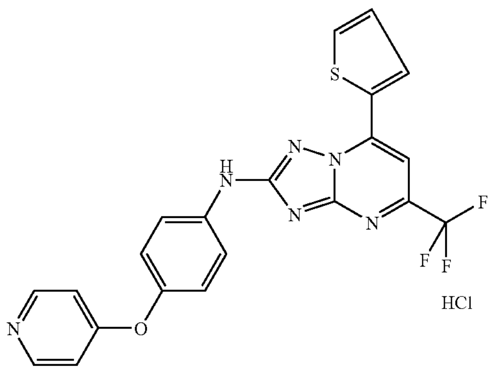 | 455 |
| 9 | 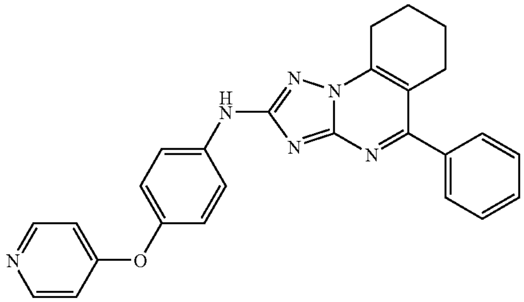 | 436 |
| 10 | 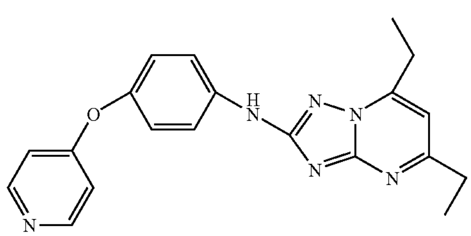 | 361 |

Example 4.1

A reaction analogous to Example 4 starting from N-{3-[2-(N-methylaminocarbonyl)pyridin-4-yloxy]phenyl}-4H-1,2,4-triazole-3,5-diamine gives the compounds "11-12b"

(7-methyl-5-trifluoromethyl-1,2,4-triazolo[1,5-a]pyrimidin-2-yl)-[3-(2-(N-methylaminocarbonyl)pyridin-4-yloxy)phenyl]amine ("11"), (M+H)+ 444;

(7-phenyl-5-trifluoromethyl-1,2,4-triazolo[1,5-a]pyrimidin-2-yl)-[3-(2-(N-methylaminocarbonyl)pyridin-4-yloxy)phenyl]amine ("12"), (M+H)+ 506; hydrochloride ("12a"), (M+H)+ 506;

(7-methyl-1,2,4-triazolo[1,5-a]pyrimidin-2-yl)-[3-(2-(N-methylaminocarbonyl)pyridin-4-yloxy)phenyl]amine ("12b"), (M+H)+ 376.

An analogous reaction starting from N-{4-[2-(N-methylaminocarbonyl)-pyridin-4-yloxy]phenyl}-4H-1,2,4-triazole-3,5-diamine gives the compounds "13" and "14"

(7-phenyl-5-trifluoromethyl-1,2,4-triazolo[1,5-a]pyrimidin-2-yl)-[4-(2-(N-methylaminocarbonyl)pyridin-4-yloxy)phenyl]amine ("13"), (M+H)+ 506;

(5,7-bistrifluoromethyl-1,2,4-triazolo[1,5-a]pyrimidin-2-yl)-[4-(2-(N-methylaminocarbonyl)pyridin-4-yloxy)phenyl]amine ("14"), (M+H)+ 498.

An analogous reaction starting from N-[4-(benzo-1,2,5-thiadiazol-5-yloxy)-phenyl]-4H-1,2,4-triazole-3,5-diamine gives the compounds "15-17"

(5,7-dimethyl-1,2,4-triazolo[1,5-a]pyrimidin-2-yl)-[4-(benzo-1,2,5-thiadiazol-5-yloxy)phenyl]amine ("15"), (M+H)⁺ 390;

(7-methyl-5-trifluoromethyl-1,2,4-triazolo[1,5-a]pyrimidin-2-yl)-[4-(benzo-1,2,5-thiadiazol-5-yloxy)phenyl]amine ("16"), (M+H)⁺ 444;

(7-phenyl-5-trifluoromethyl-1,2,4-triazolo[1,5-a]pyrimidin-2-yl)-[4-(benzo-1,2,5-thiadiazol-5-yloxy)phenyl]amine ("17"), (M+H)⁺ 506.

An analogous reaction starting from N-(2-phenylthiazol-4-ylmethyl)-4H-1,2,4-triazole-3,5-diamine gives the compounds "18-19"

(2-phenylthiazol-4-ylmethyl)-(7-phenyl-5-trifluoromethyl-1,2,4-triazolo[1,5-a]pyrimidin-2-yl)amine ("18"), (M+H)⁺ 453;

(2-phenylthiazol4-ylmethyl)-(7-methyl-5-trifluoromethyl-1,2,4-triazolo[1,5-a]pyrimidin-2-yl)amine ("19"), (M+H)⁺ 391.

An analogous reaction starting from N-[4-(pyridin-4-yloxy)phenylmethyl]-4H-1,2,4-triazole-3,5-diamine gives the compound "20"

(7-phenyl-5-trifluoromethyl-1,2,4-triazolo[1,5-a]pyrimidin-2-yl)-[4-(pyridin-4-yloxy)benzyl]amine ("20"), (M+H)⁺ 463.

An analogous reaction starting from N-(3-dimethylaminopropyl)-4H-1,2,4-triazole-3,5-diamine gives the compound "21"

(3-dimethylaminopropyl)-(7-methyl-5-trifluoromethyl-1,2,4-triazolo-[1,5-a]pyrimidin-2-yl)amine ("21"), (M+H)⁺ 303

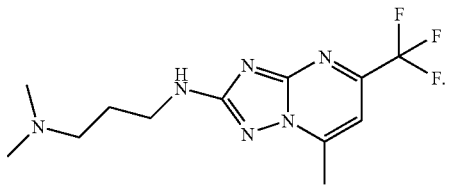

An analogous reaction starting from 5-amino-3-[4-(pyridin-4-yloxy)phenylamino]-1H-pyrazole-4-carbonitrile ("2") gives the following compounds "22-24"

7-phenyl-2-[4-(pyridin-4-yloxy)phenylamino]-5-trifluoromethylpyrazool-[1,5-a]pyrimidine-3-carbonitrile ("22"), (M+H)⁺ 473;

7-methyl-2-[4-(pyridin-4-yloxy)phenylamino]-5-trifluoromethylpyrazolo-[1,5-a]pyrimidine-3-carbonitrile ("23"), (M+H)⁺ 411;

5,7-dimethyl-2-[4-(pyridin-4-yloxy)phenylamino]pyrazolo[1,5-a]pyrimidine-3-carbonitrile ("24"), (M+H)⁺ 357.

The following compounds "25-28c" are obtained analogously 7-phenyl-2-[4-(pyridin-4-yloxy)phenylmethylamino]-5-trifluoromethylpyrazolo[1,5-a]pyrimidine-3-carbonitrile ("25"), (M+H)⁺ 487;

| No. | Structure | (M + H)⁺ |
|---|---|---|
| 26 | 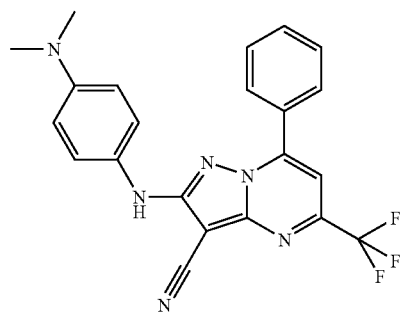 | 423 |
| 27 | 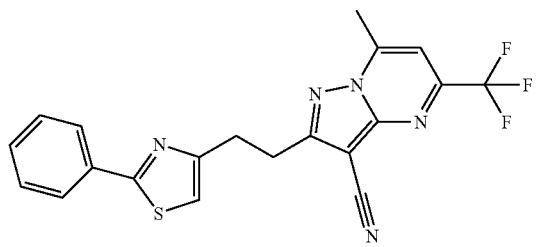 | 415 |

-continued
| No. | Structure | (M + H)⁺ |
|---|---|---|
| 28 | 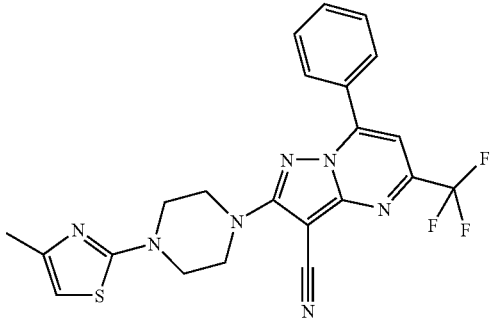 | 470 |
| 28a | 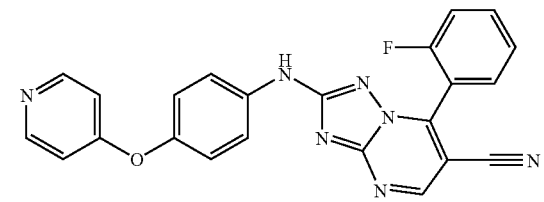 | 424 |
| 28b | 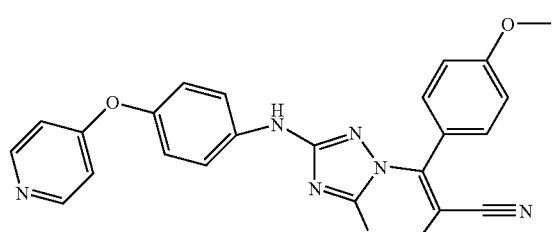 | 436 |
| 28c | 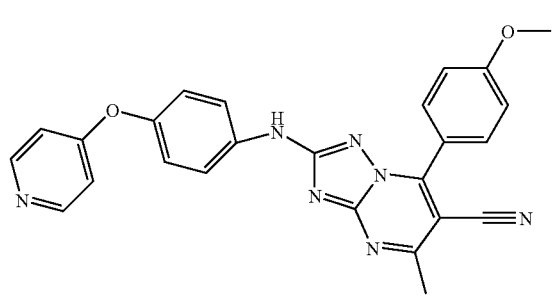 | 450 |
| 28d | 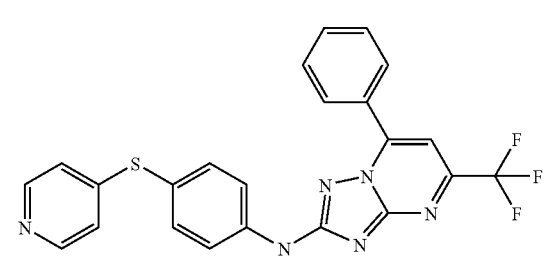 | |
| 28e | 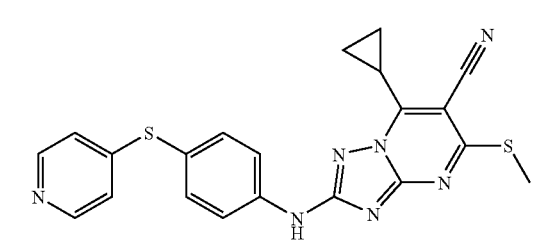 | |

A reaction analogous to the preceding examples gives the compound 6-benzyl-2-[3-(4-methylpiperazin-1-yl)propylamino]-5,6,7,8-tetrahydro-1,3,3a,6,9-pentaazacyclopenta[b]naphthalen-4-ol ("29"), dihydrochloride, (M+H)+ 438, the tautomeric form of which is shown in the reaction scheme below
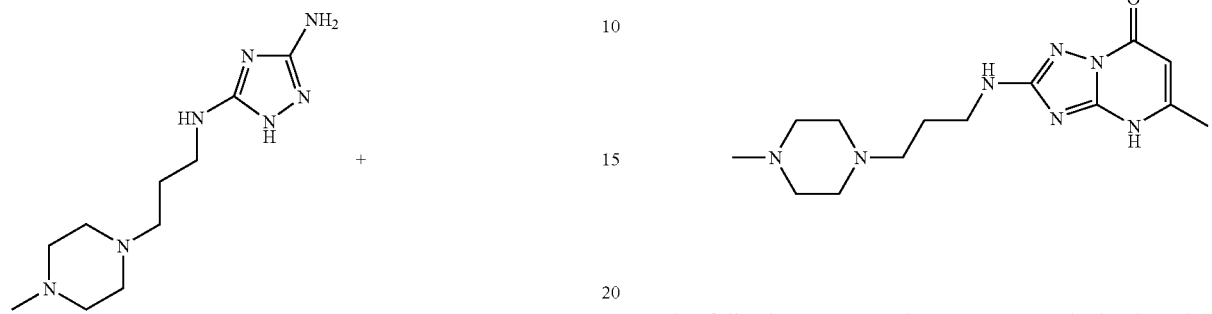
The following compounds "30-75" are obtained analogously
| No. | Structure | (M + H)+ |
|---|---|---|
| 30 | 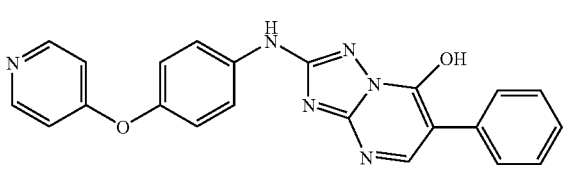 HCl | 397 |
| 31 | 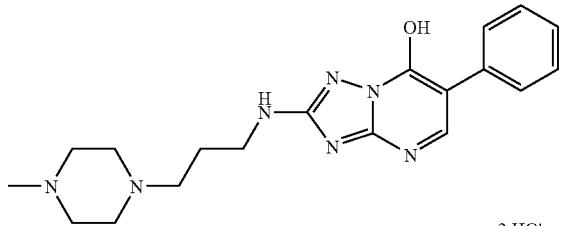 2 HCl | 368 |
| 32 | 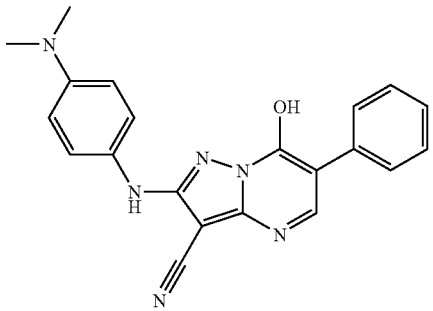 | 371 |

-continued

| No. | Structure | (M + H)+ |
|---|---|---|
| 33 | 2 HCl | 429 |
| 34 | HCl | 337 |
| 35 | HCl | 343 |
| 36 | 2 HCl | 306 |
| 37 | HCl | 335 |

-continued

| No. | Structure | (M + H)+ |
|---|---|---|
| 38 | (structure: methyl-piperazine-propyl-NH-[triazolopyrimidine with OH, CH3, and CH2C(=O)OCH3]) · 2 HCl | 378 |
| 39 | (structure: methyl-piperazine-propyl-NH-[triazolopyrimidine with OH and 2,6-dichlorophenyl]) · 2 HCl | 437 |
| 40 | (structure: methyl-piperazine-propyl-NH-[triazolo-tetrahydropyrido-pyrimidine with OH and N-methyl]) · 2 HCl | 361 |
| 41 | (structure: 4-(pyridin-4-yloxy)phenyl-NH-[triazolopyrimidine with OH and CF3]) · HCl | 389 |
| 42 | (structure: 4-(pyridin-4-yloxy)phenyl-NH-[pyrazolopyrimidine with OH, CN and CF3]) · HCl | 413 |

-continued

| No. | Structure | (M + H)+ |
|---|---|---|
| 43 | (structure) · HCl | 457 |
| 44 | (structure) | 421 |
| 45 | (structure) | 416 |
| 46 | (structure) | 359 |
| 47 | (structure) | 392 |
| 48 | (structure) · HCl | 322 |

-continued

| No. | Structure | (M + H)+ |
|---|---|---|
| 49 | 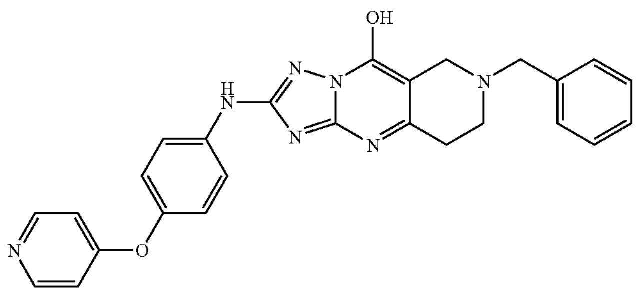 | |
| 50 | 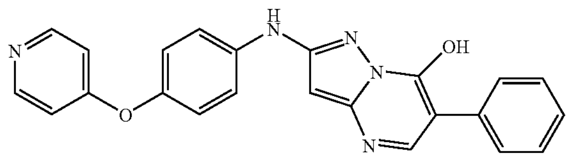 | 396 |
| 51 | 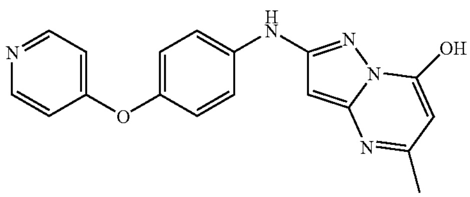 | 334 |
| 52 | 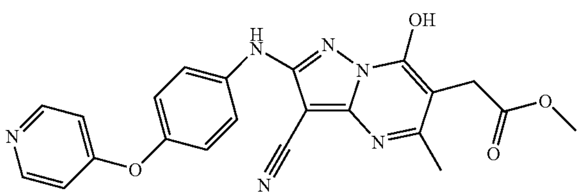 | 431 |
| 53 | 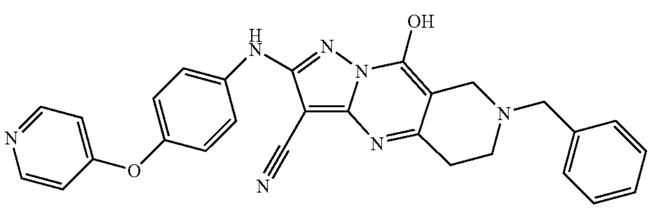 | 491 |
| 54 | 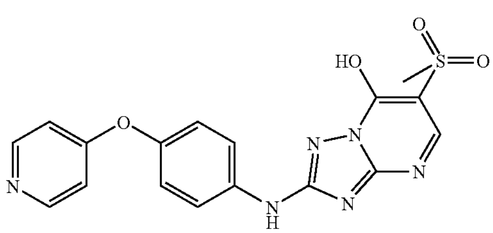 | 399 |
| 55 | 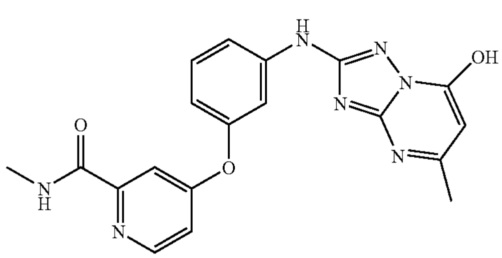 | 392 |

-continued

| No. | Structure | (M + H)⁺ |
|---|---|---|
| 56 | 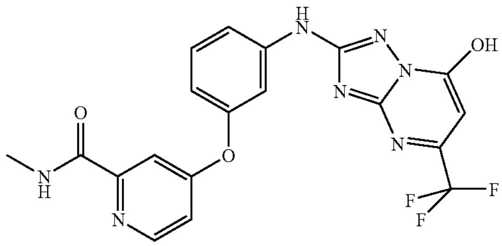 | 446 |
| 57 | 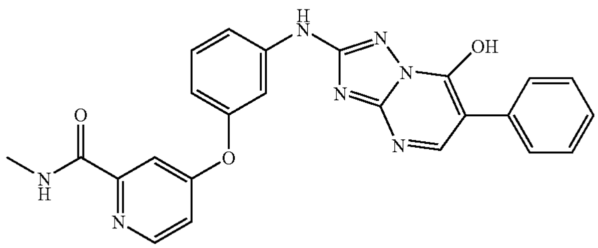 | 454 |
| 58 | 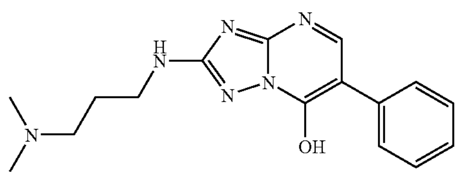 | 313 |
| 59 | 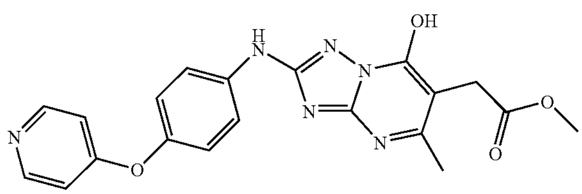 | 407 |
| 60 | 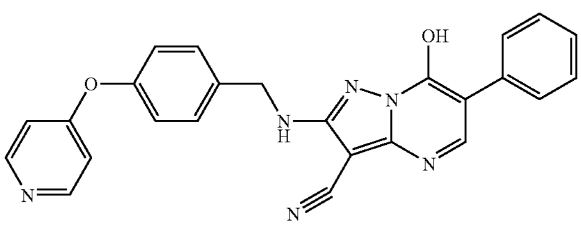 | 435 |
| 61 | 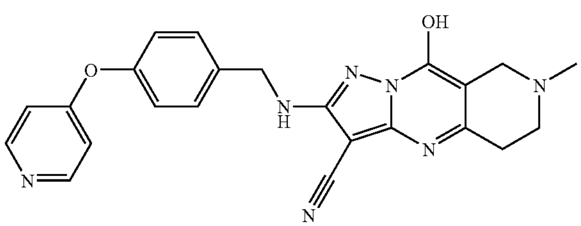 | 428 |
| 62 | 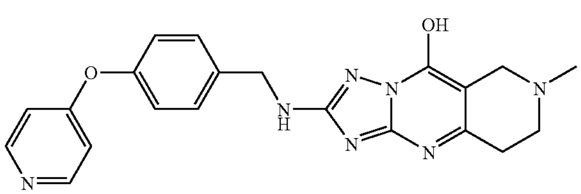 | 404 |

-continued

| No. | Structure | (M + H)+ |
|---|---|---|
| 63 | 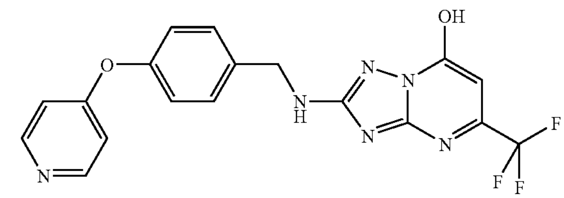 | 403 |
| 64 | 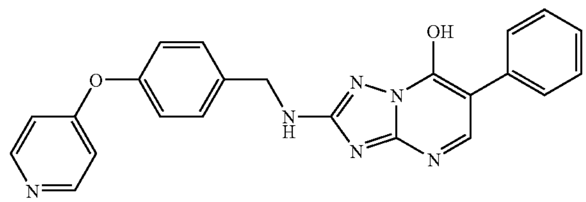 | 411 |
| 65 | 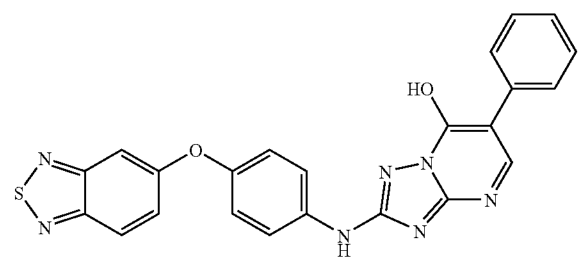 | 454 |
| 66 | 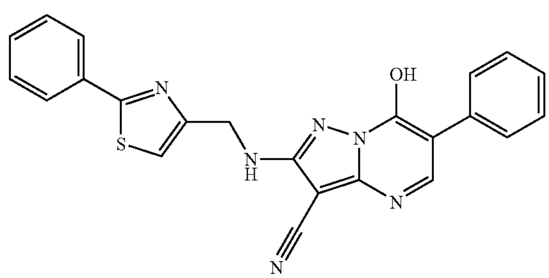 | 425 |
| 67 | 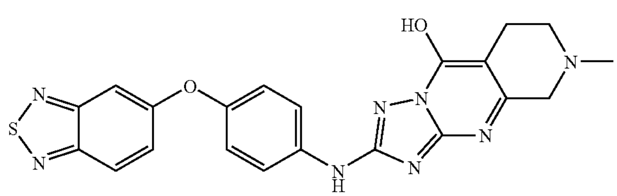 | 447 |
| 68 | 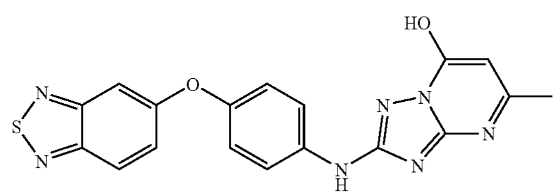 | 392 |

| No. | Structure | (M + H)+ |
|---|---|---|
| 69 | 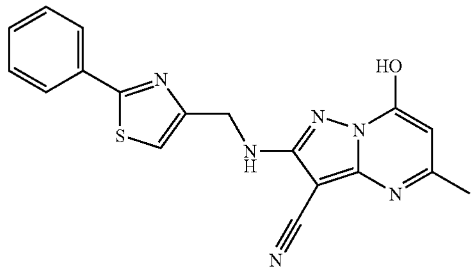 | 363 |
| 70 | 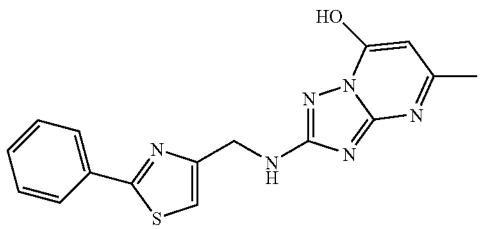 | 339 |
| 71 | 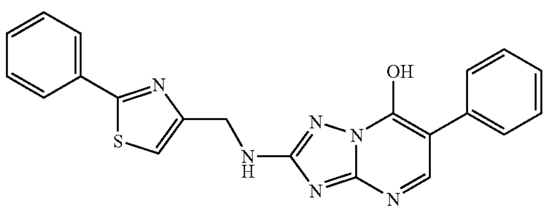 | 401 |
| 72 | 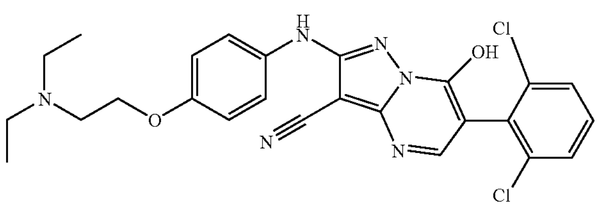 | 512 |
| 73 | 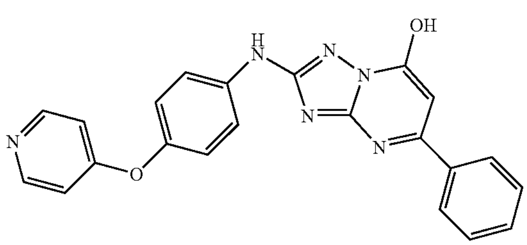 | 397 |
| 74 | 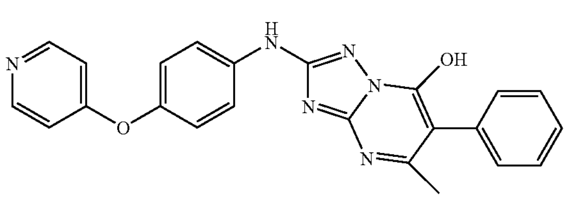 | 411 |
| 75 | 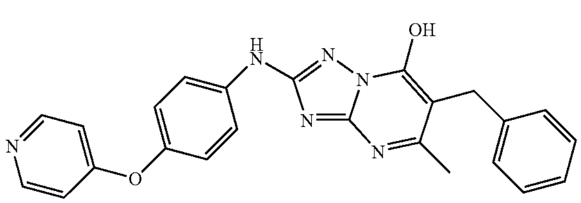 | 425 |

Example 5

Preparation of 7-(4-chlorophenyl)-5-methylsulfanyl-2-[4-(pyridin-4-yloxy)-phenylamino]-1,2,4-triazolo[1,5-a]pyrimidine-6-carbonitrile ("76")

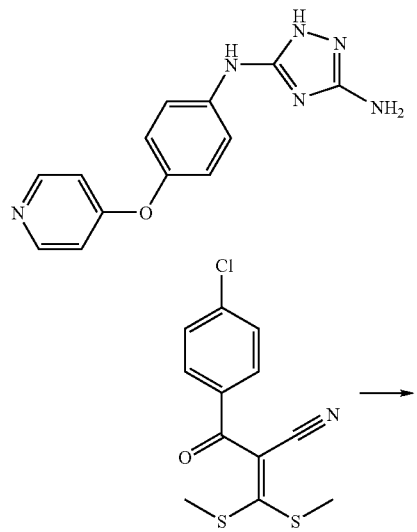

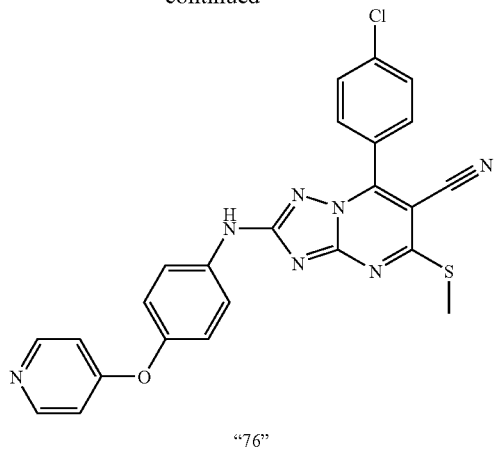

"1" (100 mg, 0.37 mol) and 2-(4-chlorobenzoyl)-3,3-bis-methylsulfanylacrylonitrile (114 mg, 0.40 mmol) are heated at 100° C. for 18 h in ethanol (1 ml) in a closed vessel. Ethyl acetate (5 ml) is added to the cooled solution, and the precipitate which forms is filtered off, washed with diethyl ether and dried, giving 125 mg (0.26 mmol, 69%) of "76", [M+H]⁺ 486, as pale-brownish solid.

The following compounds "77-125a" are obtained analogously

| No. | Structure | (M + H)⁺ |
|---|---|---|
| 77 | 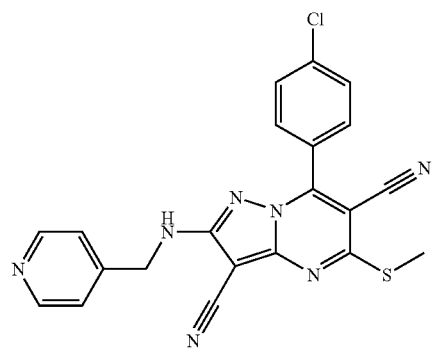 | 433 |
| 78 | 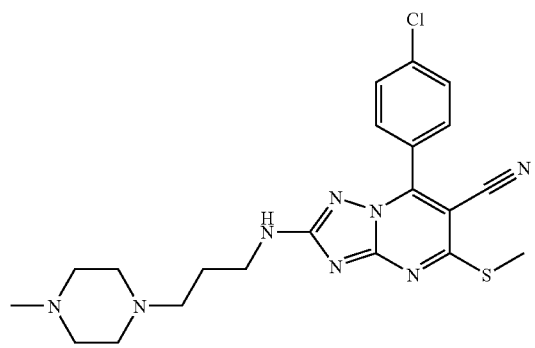 | 458 |

-continued

| No. | Structure | (M + H)+ |
|---|---|---|
| 79 | 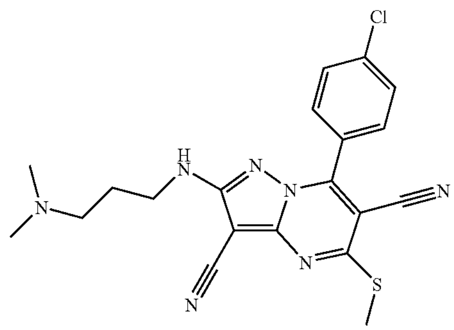 | 427 |
| 80 | 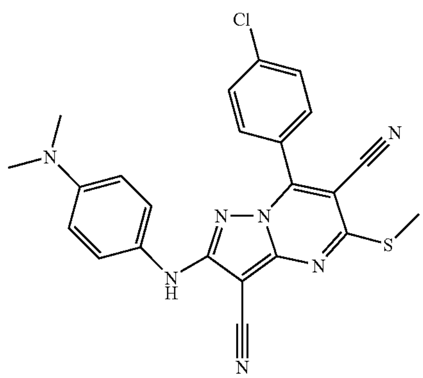 | 461 |
| 81 | 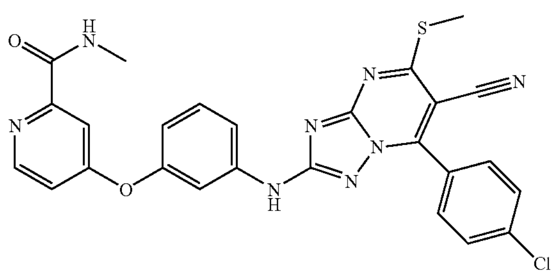 | 544 |
| 82 | 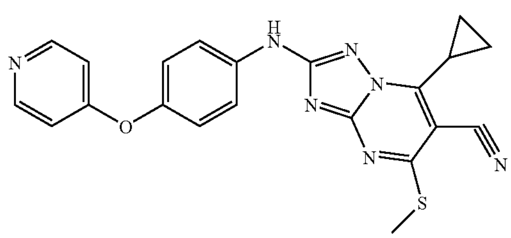 | 416 |
| 83 | 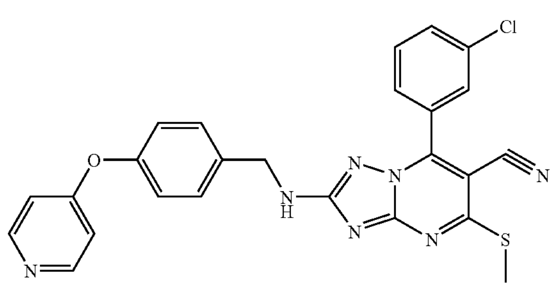 | 501 |

-continued

| No. | Structure | (M + H)+ |
|---|---|---|
| 84 | 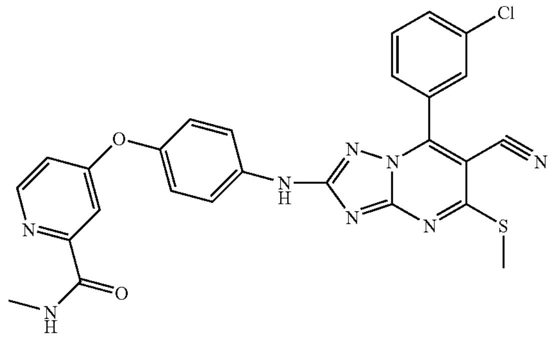 | 544 |
| 85 | 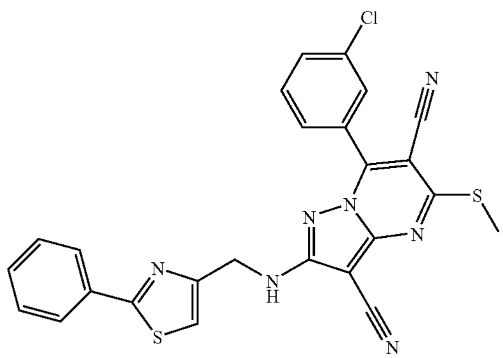 | 515 |
| 86 | 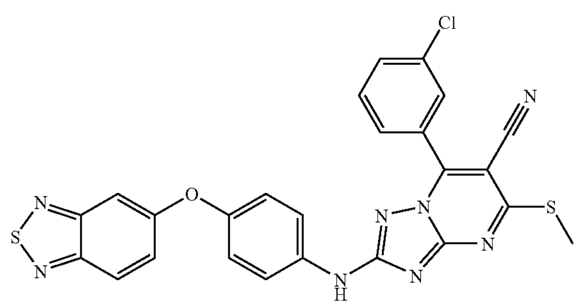 | 544 |
| 87 | 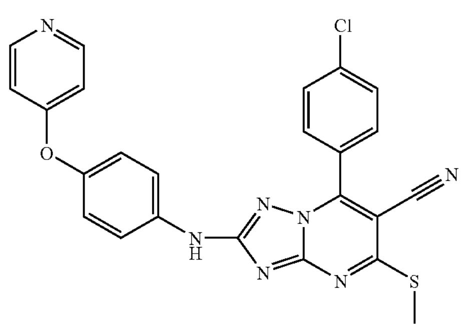 | 487 |

-continued

| No. | Structure | (M + H)+ |
|---|---|---|
| 88 | 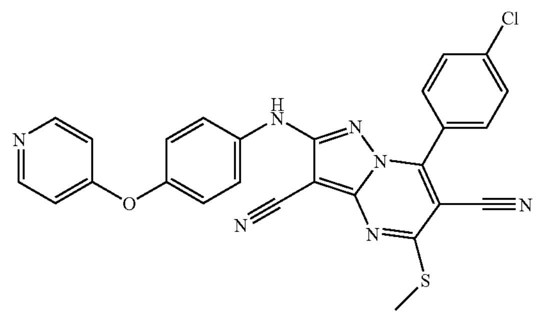 | 511 |
| 89 | 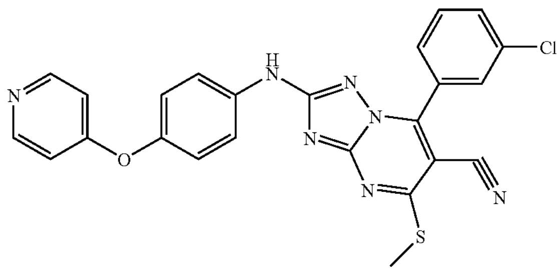 | 487 |
| 90 | 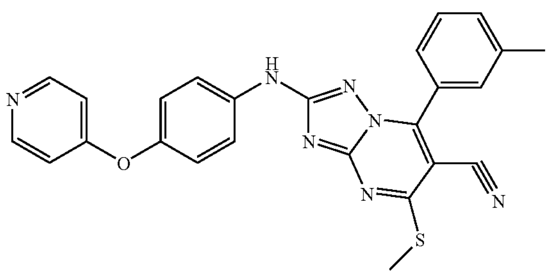 | 467 |
| 91 | 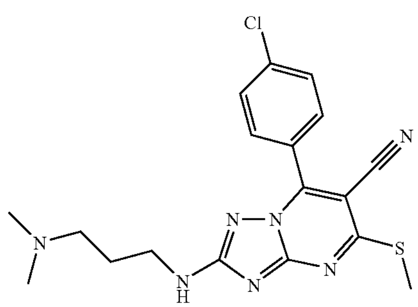 | 403 |
| 92 | 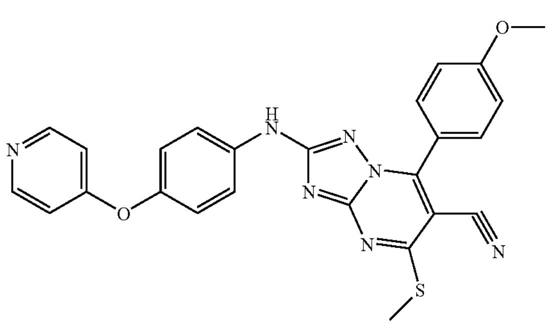 | 483 |

-continued

| No. | Structure | (M + H)+ |
|---|---|---|
| 93 | 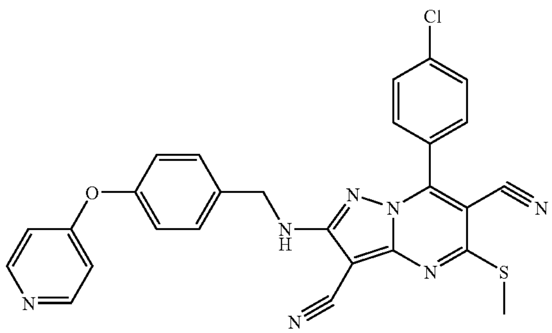 | 525 |
| 94 | 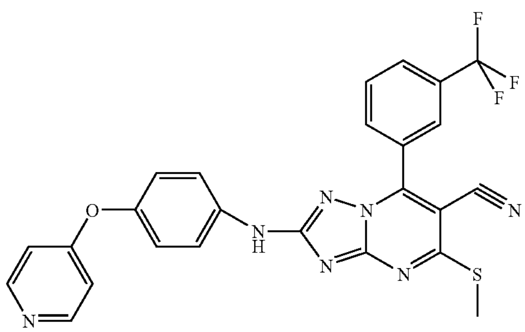 | 521 |
| 95 | 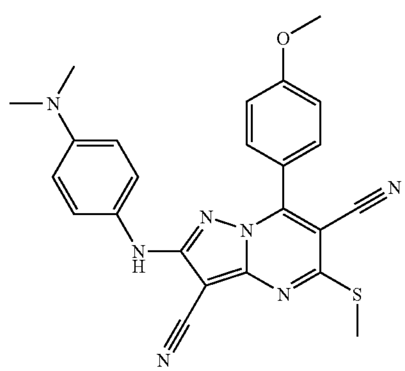 | 457 |
| 96 | 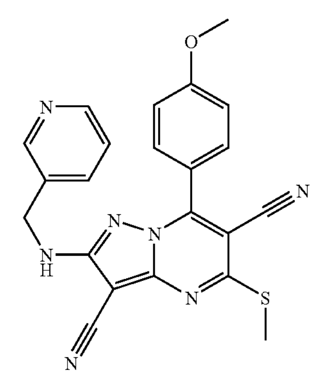 | 428 |

| No. | Structure | (M + H)⁺ |
|---|---|---|
| 97 | 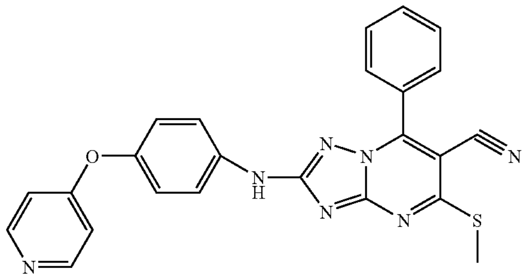 | 453 |
| 98 | 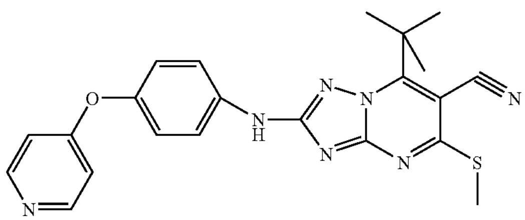 | 433 |
| 99 | 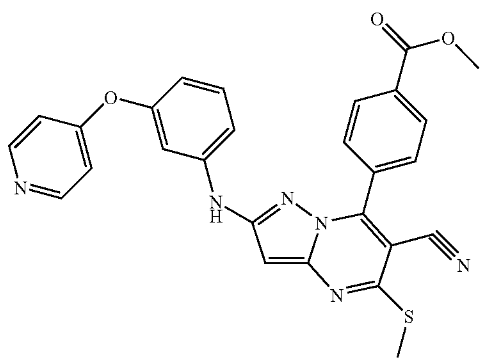 | 511 |
| 100 | 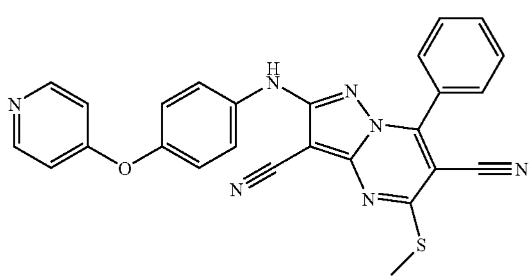 | 477 |
| 101 | 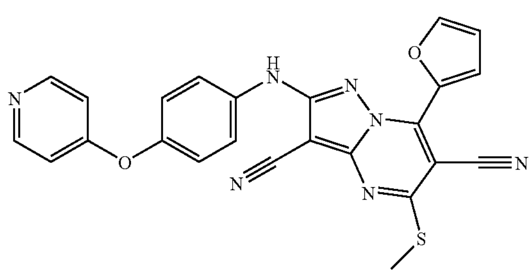 | 466 |

-continued

| No. | Structure | (M + H)+ |
|---|---|---|
| 102 | 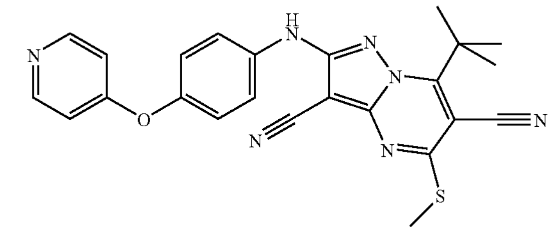 | 457 |
| 103 | 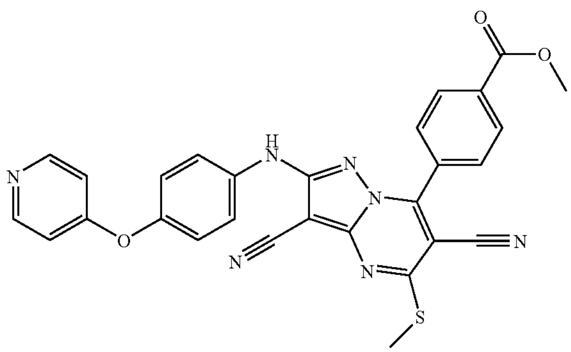 | 535 |
| 104 | 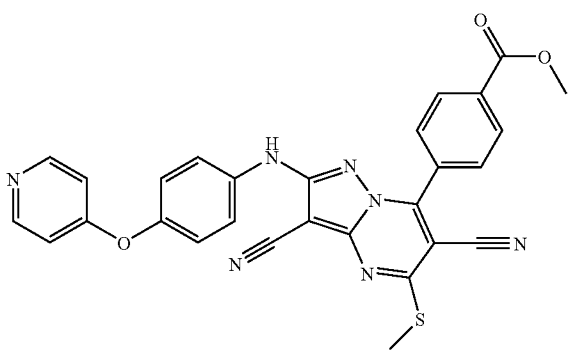 | 461 |
| 105 | 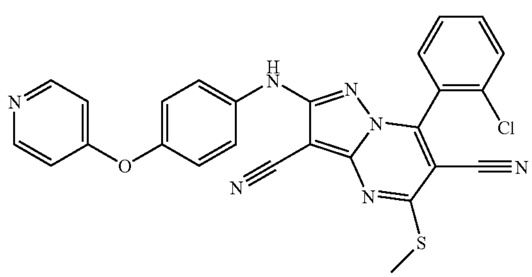 | 511 |
| 106 | 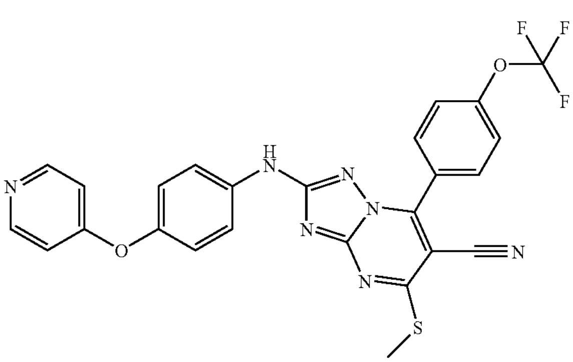 | 537 |

-continued
| No. | Structure | (M + H)+ |
|---|---|---|
| 107 | 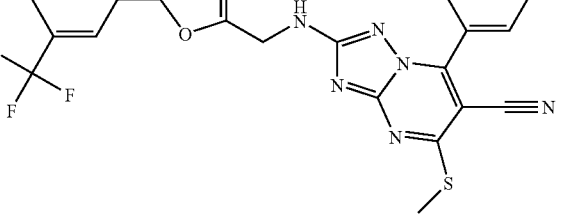 | 538 |
| 108 | 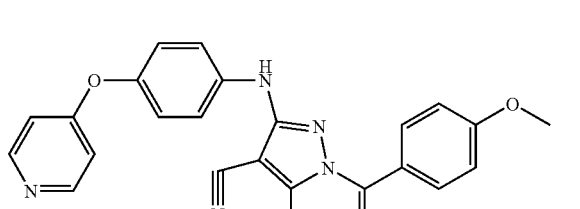 | 507 |
| 109 | 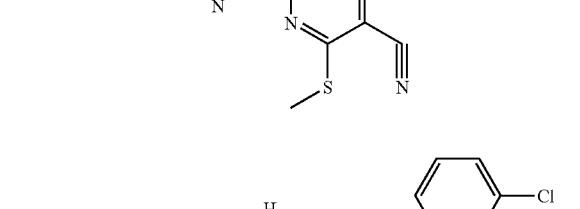 | 511 |
| 110 | 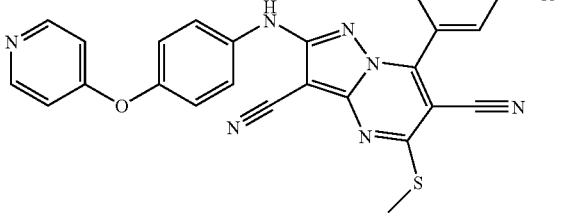 | 441 |
| 111 | 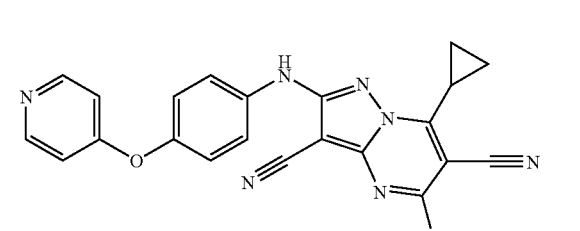 | 545 |

-continued

| No. | Structure | (M + H)+ |
|-----|-----------|----------|
| 112 | 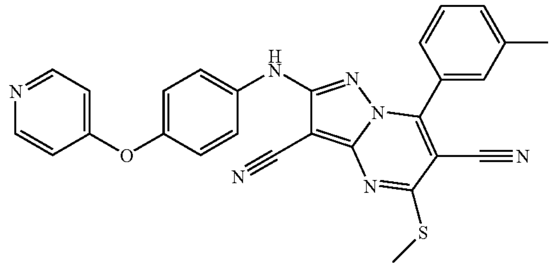 | 491 |
| 113 | 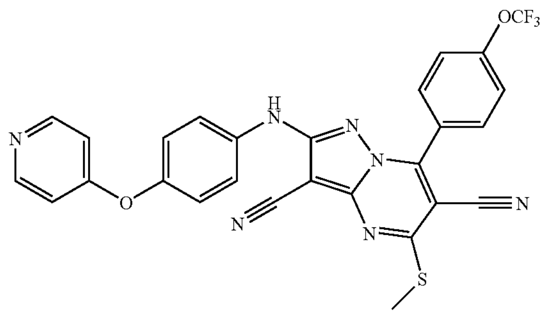 | 561 |
| 114 | 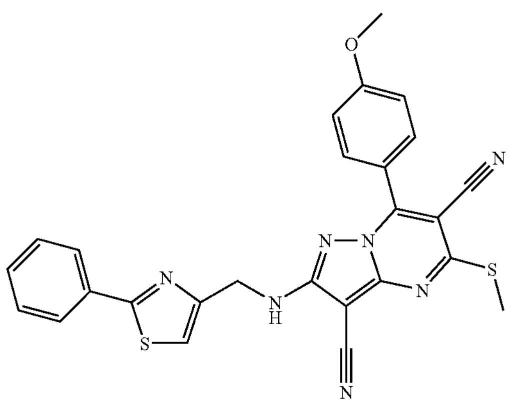 | 511 |
| 115 | 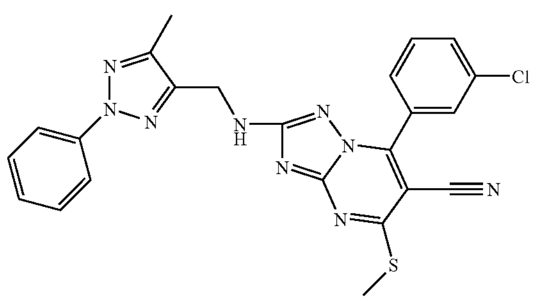 | 489 |
| 116 | 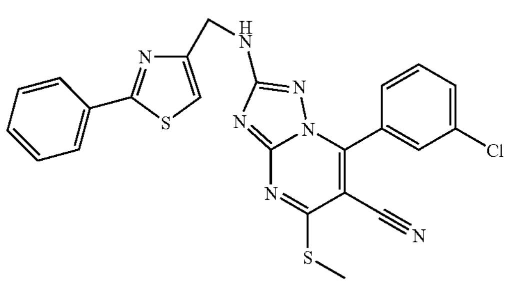 | 491 |

-continued
| No. | Structure | (M + H)+ |
|---|---|---|
| 117 | 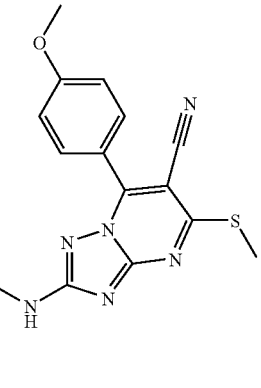 | 487 |
| 118 | 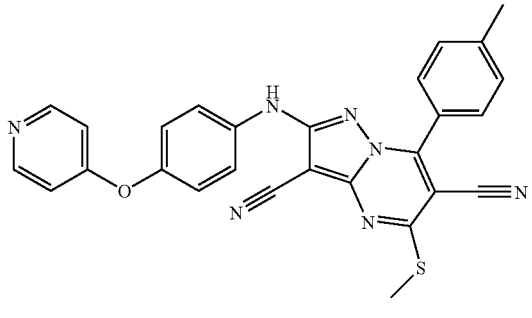 | 491 |
| 119 | 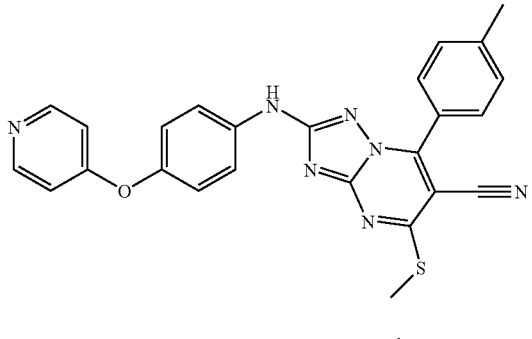 | 467 |
| 120 | 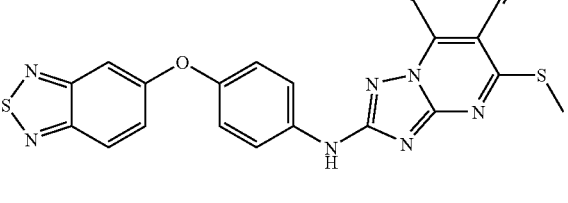 | 474 |
| 121 | 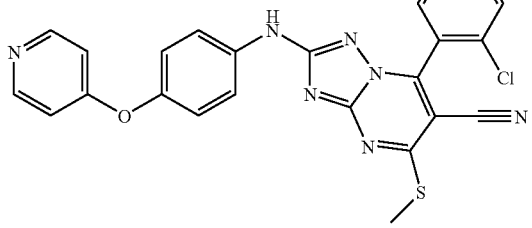 | 487 |

-continued

| No. | Structure | (M + H)+ |
|---|---|---|
| 122 | (structure) | 421 |
| 123 | (structure) | 545 |
| 124 | (structure) | 521 |
| 125 | (structure) | 504 |
| 125a | (structure) | 407 |

Example 6

Preparation of diethyl 7-(2-fluorophenyl)-2-[4-(pyridin-4-yloxy)phenylamino]-1,2,4-triazolo[1,5-a]pyrimidine-6-carboxylate ("126")

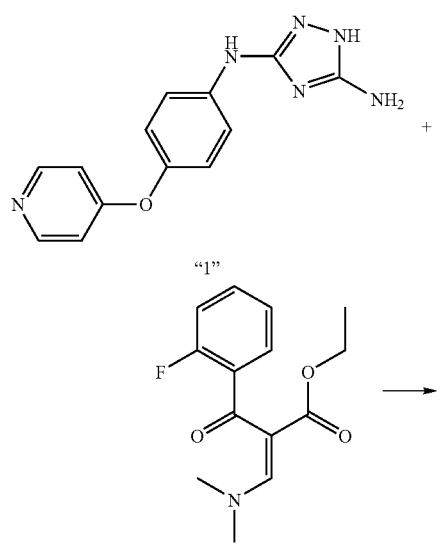

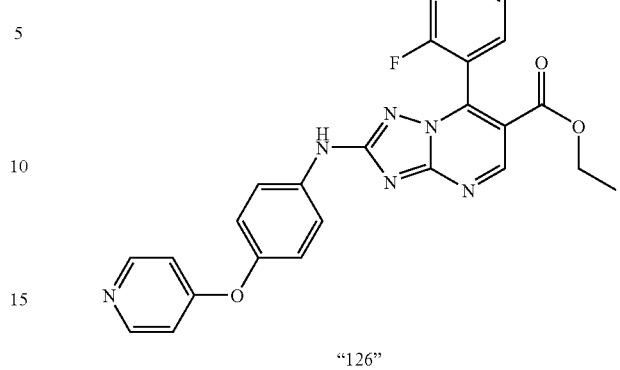

"126"

"1" (100 mg, 0.37 mol) and ethyl 3-dimethylamino-2-(2-fluorobenzoyl)acrylcarboxylate (135 mg, 0.51 mmol) are heated at 100° C. for 18 h in ethanol (1 ml) in a closed vessel. Ethyl acetate (5 ml) is added to the cooled solution, and the precipitate which forms is filtered off, washed with diethyl ether and dried, giving 109 mg (0.23 mmol, 62%) of "126", [M+H]⁺ 471, as colourless solid.

The following compounds "127-133" are obtained analogously

| No. | Structure | (M + H)⁺ |
|---|---|---|
| 127 | 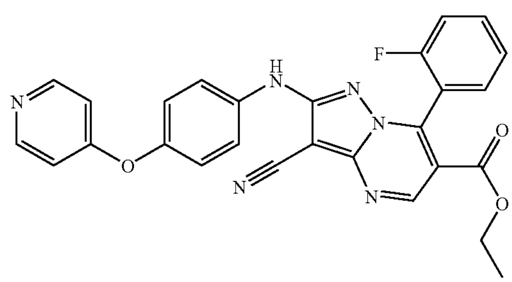 | 495 |
| 128 | 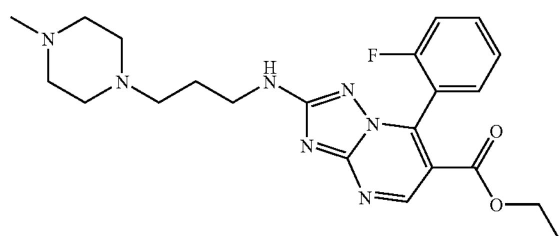 | 443 |
| 129 | 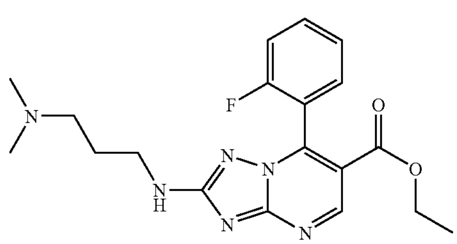 | 387 |

-continued
| No. | Structure | (M + H)+ |
|---|---|---|
| 130 | 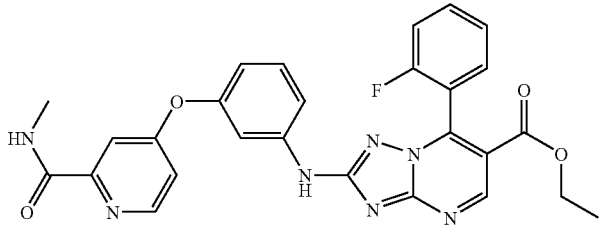 | 529 |
| 131 | 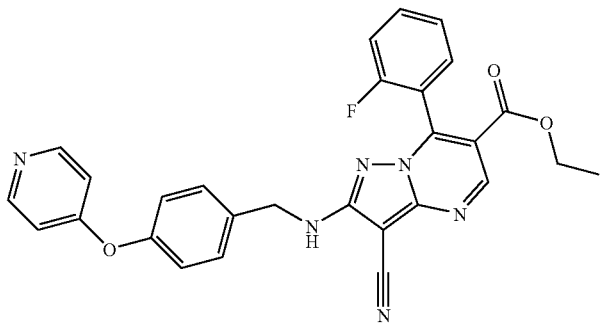 | 510 |
| 132 | 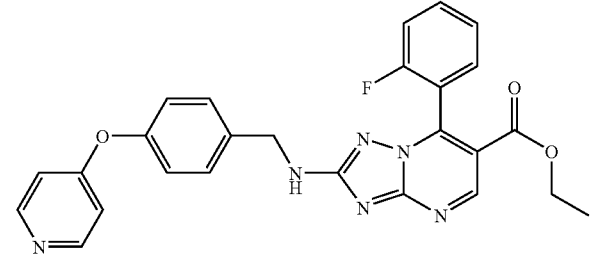 | 485 |
| 133 | 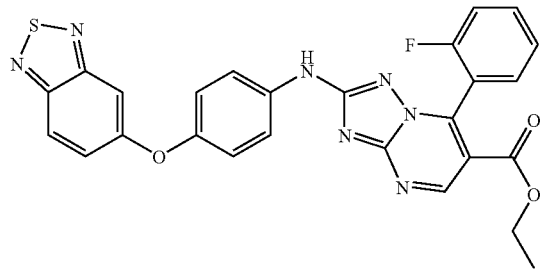 | |

Example 7

Preparation of 4-amino-2-methylsulfanyl-7-[4-(pyridin-4-yloxy)phenylamino]pyrazolo[1,5-a]-1,3,5-triazine-8-carbonitrile ("134")

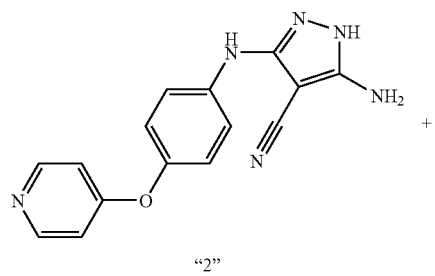

"2"

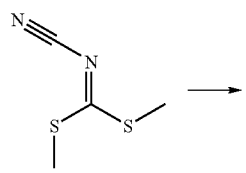

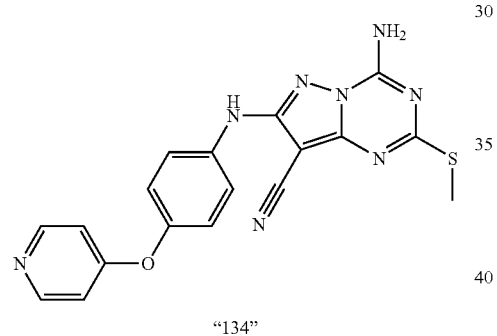

"134"

"2" (4.00, 13.7 mmol) and dimethyl N-cyanodithioiminocarbonate (2.00 g, 13.7 mmol) are dissolved in DMF (30 ml), diisopropylethylamine (23.3 ml, 137 mmol) is added, and the mixture is heated at 150° C. for 18 h. Water is added to the cooled solution, and the precipitate which forms is filtered off, washed with water and dried, giving 4.70 g (12.1 mmol, 88%) of "134", [M+H]⁺ 391, as colourless solid.

The following compounds "135" and "135a" are obtained analogously

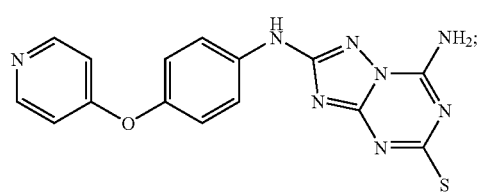

"135"

[M + H]⁺ 367

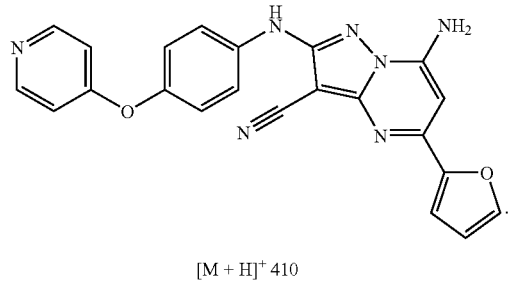

"135a"

[M + H]⁺ 410

Example 8

Preparation of 7-(3-chlorophenyl)-5-(4-methylpiperazin-1-yl)-2-[4-(pyridin-4-yloxy)phenylamino]-1,2,4-triazolo[1,5-a]pyrimidine-6-carbonitrile ("136")

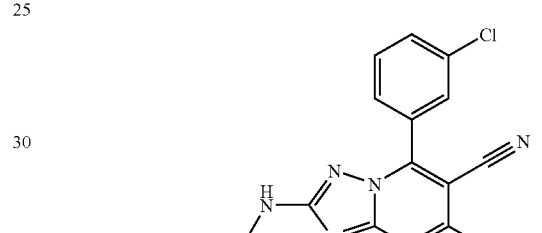

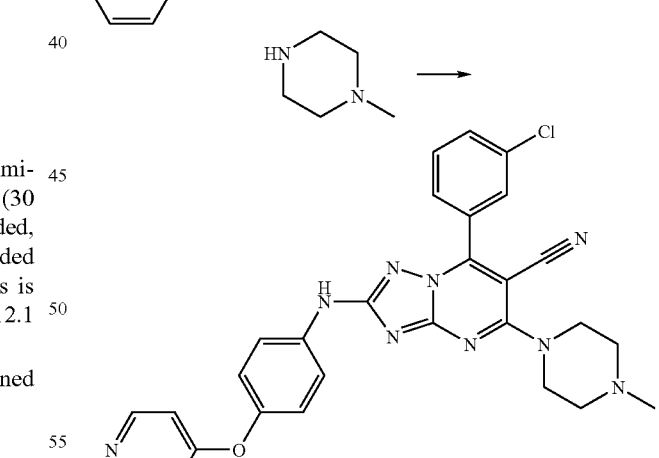

"136"

7-(3-Chlorophenyl)-5-methylsulfanyl-2-[4-(pyridin-4-yloxy)phenylamino]-1,2,4-triazolo[1,5-a]pyrimidine-6-carbonitrile (50 mg, 0.10 mol) is heated at 100° C. for 18 h in 1-methylpiperazine (1 ml) in a closed vessel. Ethyl acetate (5 ml) is added to the cooled solution, and the precipitate which forms is filtered off, washed with diethyl ether and dried, giving 32 mg (0.06 mmol, 55%) of "136", [M+H]⁺ 539.

The following compounds "137-139" are obtained analogously
| No. | Structure | (M + H)+ |
|---|---|---|
| 137 | 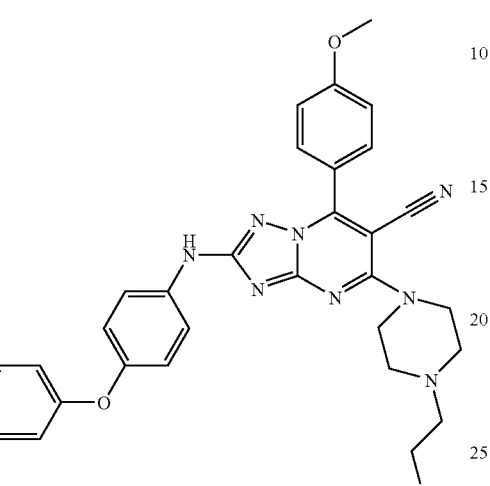 | 565 |
| 138 | 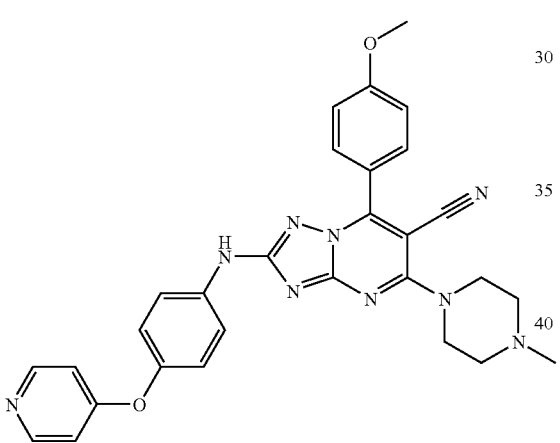 | 535 |
| 139 | 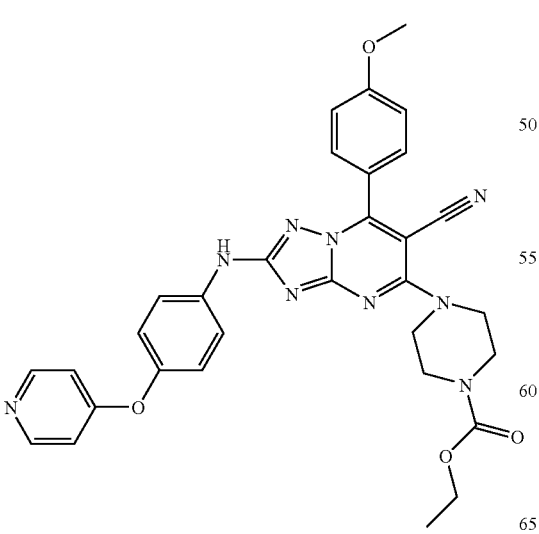 | 593 |

Example 9

Preparation of 4-amino-2-[(2-dimethylaminoethyl)methylamino]-7-[4-(pyridin-4-yloxy)phenylamino]pyrazolo[1,5-a]-1,3,5-triazine-8-carbonitrile ("140")

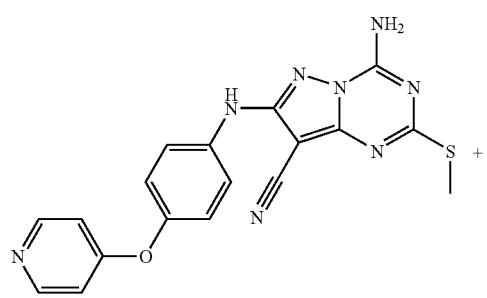

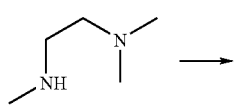

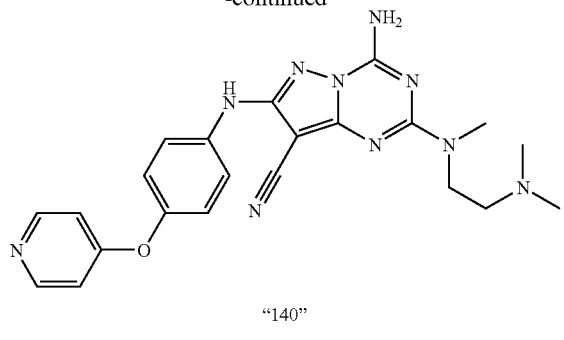

"140"

4-Amino-2-methylsulfanyl-7-[4-(pyridin-4-yloxy)phenylamino]pyrazolo-[1,5-a]-1,3,5-triazine-8-carbonitrile (60.3 mg, 0.15 mol) is initially introduced in DMF (0.5 mmol), 2-dimethylamino-N-methylethylamine (19.4 mg, 0.19 mmol) is added, and the mixture is heated at 100° C. for 18 h. Ethyl acetate (5 ml) is added to the cooled solution, and the precipitate which forms is filtered off, washed with diethyl ether and dried, giving 39 mg (0.09 mmol, 57%) of "140", $[M+H]^+$ 446 as colourless solid.

The following compounds "141-157" are obtained analogously

| No. | Structure | $(M + H)^+$ |
|---|---|---|
| 141 | 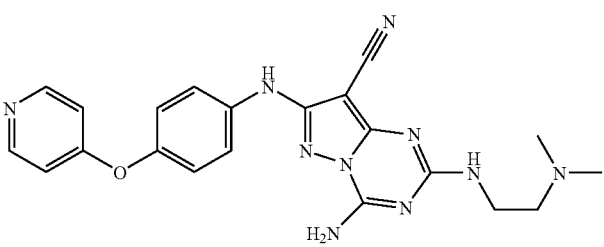 | 431 |
| 142 | 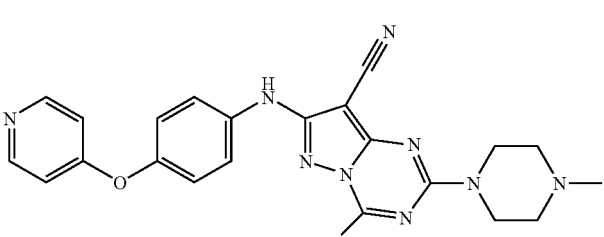 HCl | 443 |
| 143 | 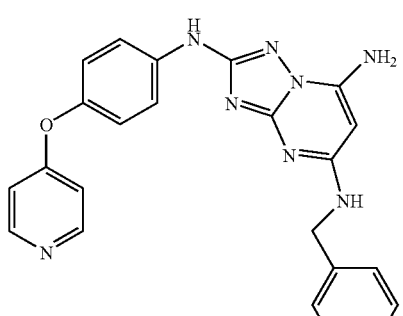 | 425 |

-continued

| No. | Structure | (M + H)+ |
|---|---|---|
| 144 | 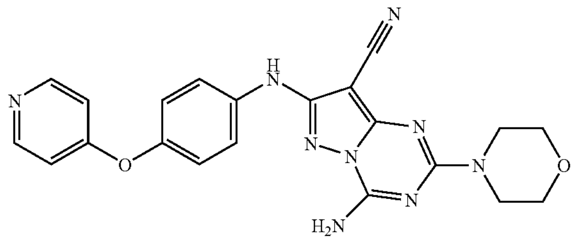 | 430 |
| 145 | 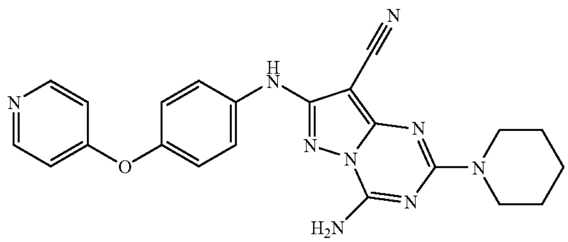 | 428 |
| 146 | 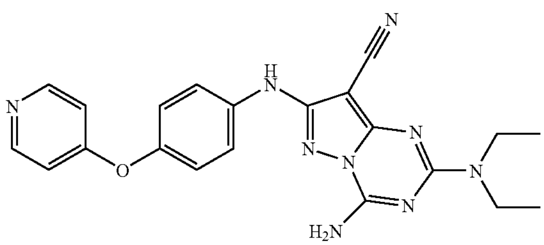 | 416 |
| 147 | 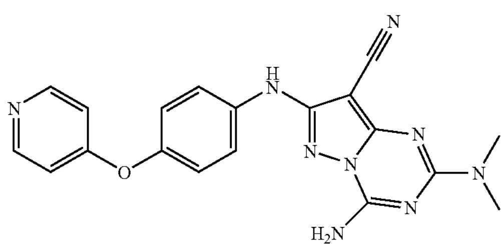 | 472 |
| 148 | 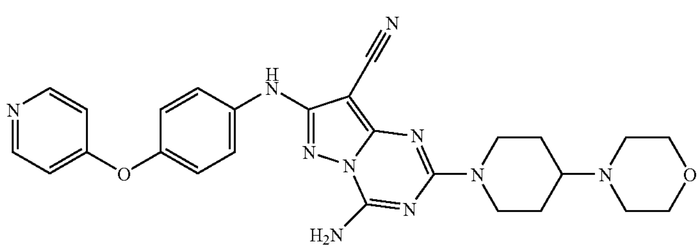 | 514 |
| 149 | 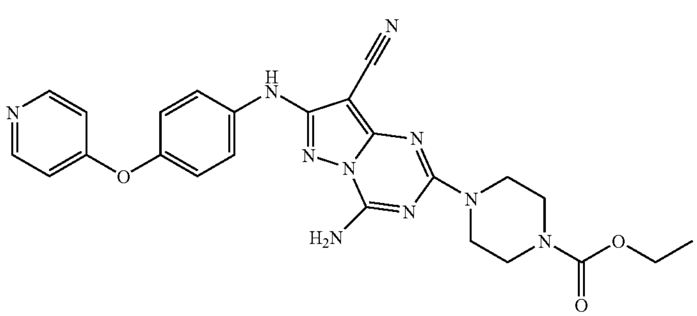 | 502 |

-continued
| No. | Structure | (M + H)+ |
|---|---|---|
| 150 | 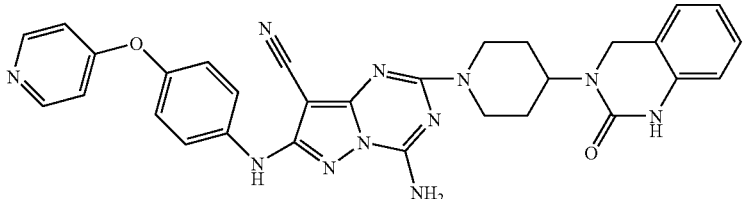 | 575 |
| 151 | 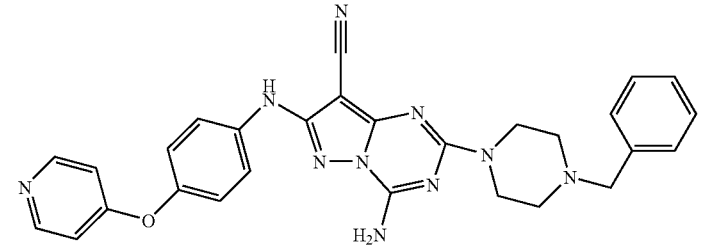 | 520 |
| 152 | 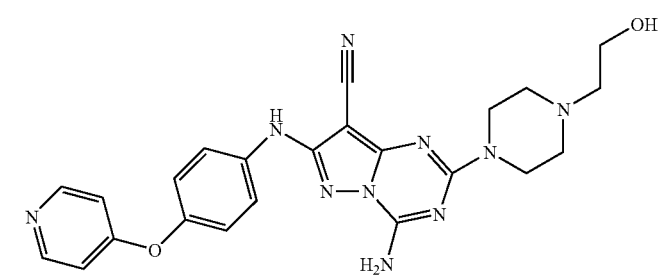 | 474 |
| 153 | 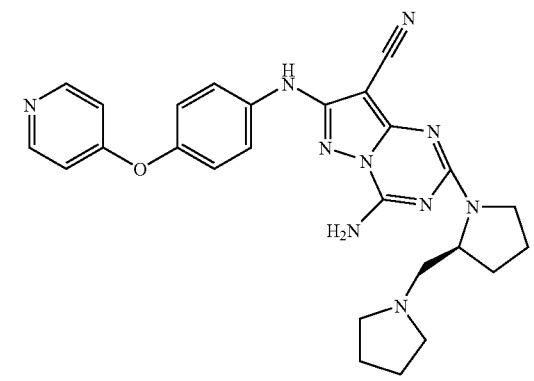 | 498 |
| 154 | 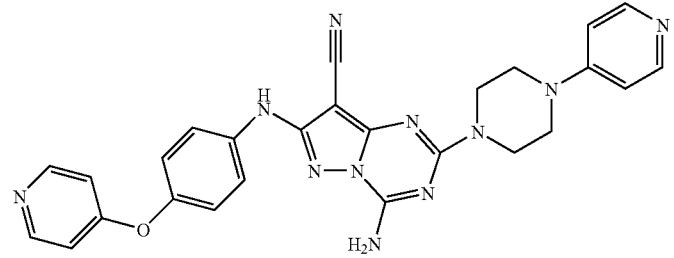 | 507 |

-continued

| No. | Structure | (M + H)+ |
|---|---|---|
| 155 | 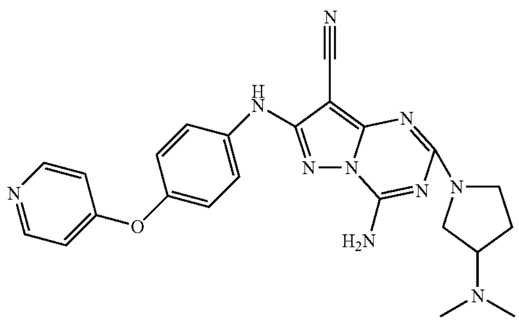 | 458 |
| 156 | 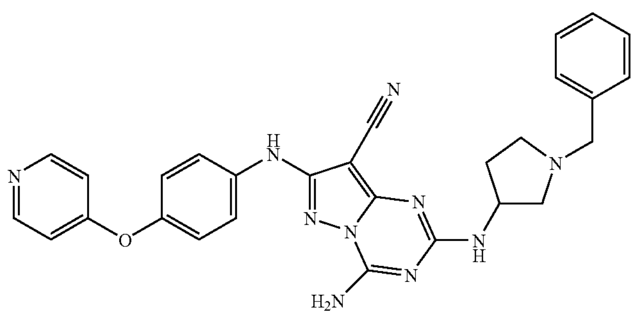 | 520 |
| 157 | 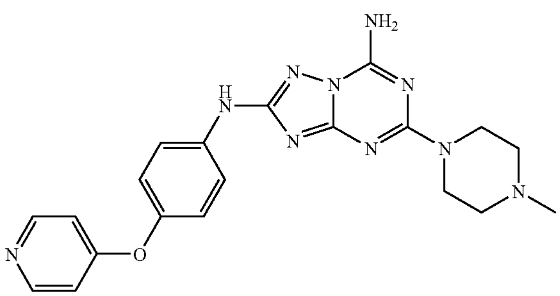 | 419 |

Example 10

The Preparation of (5-methylsulfanil-7-phenyl-1,2,4-triazolo[1,5-a]-1,3,5-triazin-2-yl)-[4-(pyridin-4-yloxy)phenyl]amine ("158") is Carried Out as Described Below

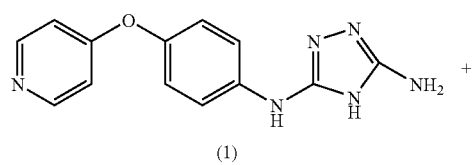

(1)

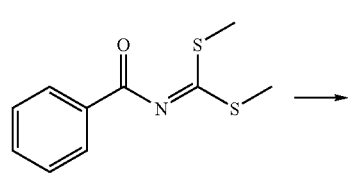

-continued

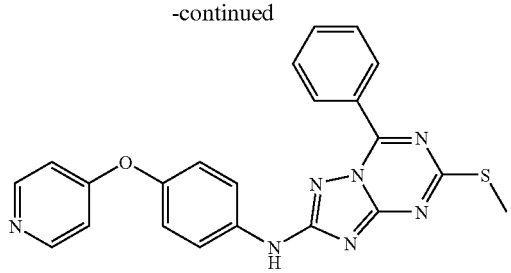

Compound 1 (268 mg, 1.00 mmol) is stirred at 80° C. for 18 h with N-(bis-methylsulfanylmethylene)benzamide* (225 mg, 1.00 mmol) in ethanol. The product is precipitated by addition of diethyl ether, filtered off, washed with diethyl ether and dried, giving 220 mg (0.51 mmol, 51%) of "158".

* *Synthesis* 1981, 554-557.

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of $NaH_2PO_4.2\ H_2O$, 28.48 g of $Na_2HPO_4.12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

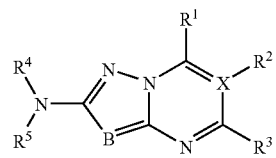

in which
X denotes C,
B denotes N, CH or C—CN,
$R^1$ denotes, A, —$(CH_2)_m$—Ar or —$(CH_2)_m$-$Het^2$,
$R^2$ denotes CN,
$R^3$ denotes H, A, —S-A, —$(CH_2)_p$—Ar, —$(CH_2)_p$-Het, NH—$(CH_2)_p$—Ar, NH—$(CH_2)_p$-Het, $NH_2$, NHA, $NA_2$, NH-alkylene-$NH_2$, NH-alkylene-NHA, NH-alkylene-$NA_2$ or NA-alkylene-$NA_2$,
$R^4$ denotes —$(CH_2)_s$—$(Ar^1)_n$—Y—$R^6$,
$R^5$ denotes H or $CH_3$, or
$R^4$ and $R^5$ together denote

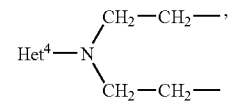

$R^6$ denotes $Het^4$, —$(CH_2)_r$—$NH_2$, —$(CH_2)_r$—NHA or —$(CH_2)_r$—$NA_2$,
Y denotes O, S, $(CH_2)_q$ or NH,
Ar denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or—$OCH_2$—COOH,
$Ar^1$ denotes phenylene or piperazinediyl,
Het denotes a mono- or bicyclic saturated, unsaturated or aromatic heterocycle having 1 to 4 N, O and/or S atoms, which may be unsubstituted or mono-, di- or trisubstituted by Hal, A, NHA, $NA_2$, OA, COOA, CN, —$(CH_2)_p$—Ar, —$(CH_2)_r$—OH, —$(CH_2)_p$-$Het^1$ or carbonyl oxygen (=O),
$Het^1$ denotes a mono- or bicyclic saturated, unsaturated or aromatic heterocycle having 1 to 4 N, O and/or S atoms, which may be unsubstituted or mono- or disubstituted by A or carbonyl oxygen (=O),
$Het^2$ denotes a monocyclic aromatic heterocycle having 1 to 3 N, O and/or S atoms, which may be unsubstituted or mono- or disubstituted by A,
$Het^3$ denotes a monocyclic saturated or aromatic heterocycle having 1 to 3 N, O and/or S atoms, which may be unsubstituted or mono- or disubstituted by A, Het⁴ denotes a mono- or bicyclic saturated, unsaturated or aromatic heterocycle having 1 to 4 N, O and/or S atoms, which may be unsubstituted or mono-, di- or trisubstituted by Hal, A, CONH$_2$, CONHA, CONA$_2$ or Ar², Ar² denotes phenyl which is unsubstituted or mono-, di- or trisubstituted by Hal, A, OH, OA, NH$_2$, NO$_2$, CN, COOH, COOA, CONH$_2$, NHCOA, NHCONH$_2$, NHSO$_2$A, CHO, COA, SO$_2$NH$_2$ or SO$_2$A, $R^7$, $R^8$, $R^9$, $R^{10}$ each, independently of one another, denote H, A or —(CH$_2$)$_p$—Ar, A denotes alkyl having 1 to 10 C atoms, where, in addition, 1-7 H atoms may be replaced by F and/or chlorine, m denotes 0, 1, 2, 3 or 4,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
Hal denotes F, Cl, Br or I,
and, if Ar¹ denotes piperazinediyl,
  R⁶ may also denote H or alkyl having 1-6 C atoms, or a pharmaceutically acceptable tautomer, salt or stereoisomer thereof.

2. A compound according to claim 1 in which
$R^1$ denotes A, —(CH$_2$)$_m$—Ar or —(CH$_2$)$_m$-Het²,
Ar denotes phenyl which is unsubstituted or mono-, di- or trisubstituted by Hal, A, OA, COOH or COOA,
m denotes 0.

3. A compound according to claim 1 in which
$R^4$ denotes —(CH$_2$)$_s$—(Ar¹)$_n$—Y—R⁶,
s denotes 0 or 1,
n denotes 1,
Ar¹ denotes phenylene,
R⁶ denotes Het⁴,
Y denotes O,
Het⁴ denotes pyridyl which is unsubstituted or monosubstituted by CONHA, or benzo-1,2,5-thiadiazol-5-yl.

4. A compound according to claim 1 in which
$R^4$ denotes —(CH$_2$)$_s$—(Ar¹)$_n$—Y—R⁶,
s denotes 1,
n denotes 0,
Y denotes (CH$_2$)$_q$,
q denotes 0,
R⁶ denotes Het⁴,
Het⁴ denotes pyridyl, benzo-1,2,5-thiadiazol-5-yl, thiazole, 1,2,3-triazole, thienyl or furyl, each of which is unsubstituted or monosubstituted by CONHA, A and/or Ar²,
Ar² denotes phenyl which is unsubstituted or mono-, di- or trisubstituted by A.

5. A compound according to claim 1 in which
$R^4$ denotes —(CH$_2$)$_s$—(Ar¹)$_n$—Y—R⁶,
s denotes 0,
n denotes 0,
Y denotes (CH$_2$)$_q$,
q denotes 0,
R⁶ denotes —(CH$_2$)$_r$—NH$_2$, —(CH$_2$)$_r$NHA or —(CH$_2$)$_r$—NA$_2$,
r denotes 1,2,3 or 4.

6. A compound according to claim 1 in which
$R^4$ denotes —(CH$_2$)$_s$—(Ar¹)$_n$—Y—R⁶,
s denotes 0,
n denotes 1,
Ar¹ denotes phenylene,
Y denotes O, (CH$_2$)$_q$ or NH,
R⁶ denotes —(CH$_2$)$_r$—NH$_2$, —(CH$_2$)$_r$—NHA or —(CH$_2$)$_r$—NA$_2$,
q denotes 0, 1, 2, 3 or 4,
r denotes 0, 1, 2, 3 or 4.

7. A compound according to claim 1 in which
$R^4$ denotes —(CH$_2$)$_s$—(Ar¹)$_n$—Y—R⁶,
s denotes 1, 2, 3 or 4,
n denotes 0,
Y denotes (CH$_2$)$_q$,
q denotes 0,
R⁶ denotes Het⁴,
Het⁴ denotes a monocyclic saturated heterocycle having 1 to 2 N and/or O atoms, which may be unsubstituted or mono- or disubstituted by A.

8. A compound according to claim 1 in which
$R^1$ denotes A, —(CH$_2$)$_m$—Ar,
m denotes 0,
Ar denotes phenyl which is unsubstituted or mono-, di- or trisubstituted by Hal, A, OA, COOH or COOA,
$R^2$ denotes CN,
$R^3$ denotes H, A, —S-A, phenyl or —(CH$_2$)$_p$-Het.

9. A compound according to claim 1 in which
$R^1$ denotes A, —(CH$_2$)$_m$—Ar,
m denotes 0,
Ar denotes phenyl which is unsubstituted or mono-, di- or trisubstituted by Hal, A, OA, COOH or COOA,
$R^2$ denotes CN,
$R^3$ denotes H, A, —S-A, phenyl or —(CH$_2$)$_p$-Het,
$R^4$ denotes —(CH$_2$)$_s$—(Ar¹)$_n$—Y—R⁶,
s denotes 0,
n denotes 0,
Y denotes (CH$_2$)$_q$,
q denotes 0,
R⁶ denotes —(CH$_2$)$_r$—NH$_2$,—(CH$_2$)$_r$—NHA or —(CH$_2$)$_r$—NA$_2$,
r denotes 1, 2, 3 or 4.

10. A compound according to claim 1 in which
$R^4$ denotes —(CH$_2$)$_s$—(Ar¹)$_n$—Y—R⁶,
s denotes 0,
n denotes 1,
Y denotes (CH$_2$)$_q$,
q denotes 0,
R⁶ denotes —(CH$_2$)$_r$—NH$_2$,—(CH$_2$)$_r$—NHA or —(CH$_2$)$_r$—NA$_2$,
r denotes 0.

11. A compound according to claim 1 in which
$R^4$ denotes —(CH$_2$)$_s$—(Ar¹)$_n$—Y—R⁶,
s denotes 0,
n denotes 0 or 1,
Y denotes (CH$_2$)$_q$,
q denotes 0,
R⁶ denotes —(CH$_2$)$_r$—NH$_2$,—(CH$_2$)$_r$—NHA or —(CH$_2$)$_r$—NA$_2$,
r denotes 0, 1, 2, 3 or 4.

12. A compound according to claim 1 in which
$R^4$ denotes —(CH$_2$)$_s$—(Ar¹)$_n$—Y—R⁶,
s denotes 0,
n denotes 0 or 1,
Y denotes (CH$_2$)$_q$,
R⁶ denotes —(CH$_2$)$_r$—NH$_2$,—(CH$_2$)$_r$—NHA or —(CH$_2$)$_r$—NA$_2$,
Ar¹ denotes phenylene,
Y denotes O, (CH$_2$)$_q$ or NH,
q denotes 0, 1, 2, 3 or 4,
r denotes 0, 1, 2, 3 or 4.

13. A compound according to claim 1 in which $R^1$ denotes A, —(CH$_2$)$_m$—Ar,
m denotes 0,
Ar denotes phenyl which is unsubstituted or mono-, di- or trisubstituted by Hal, A, OA, COOH or COOA,
$R^2$ denotes CN,
$R^3$ denotes H, A, —S-A, phenyl or —(CH$_2$)$_p$-Het,
$R^4$ denotes —(CH$_2$)$_s$—(Ar$^1$)$_n$—Y—R$^6$,
s denotes 0,
n denotes 0 or 1,
Y denotes (CH$_2$)$_q$,
$R^6$ denotes —(CH$_2$)$_r$—NH$_2$,—(CH$_2$)$_r$—NHA or —(CH$_2$)$_r$—NA$_2$,
Ar$^1$ denotes phenylene,
Y denotes O, (CH$_2$)$_q$ or NH,
q denotes 0, 1, 2, 3 or 4,
r denotes 0, 1, 2, 3 or 4.

14. A compound according to claim 1 in which
$R^1$ denotes A, —(CH$_2$)$_m$—Ar,
m denotes 0,
Ar denotes phenyl which is unsubstituted or mono-, di- or trisubstituted by Hal, A, OA, COOH or COOA,
$R^2$ denotes CN,
$R^3$ denotes H, A, —S-A, phenyl or —(CH$_2$)$_p$-Het,
$R^4$ denotes —(CH$_2$)$_s$—(Ar$^1$)$_n$—Y—R$^6$,
s denotes 0,
n denotes 1,
Ar$^1$ denotes phenylene,
$R^6$ denotes Het$^4$,
Y denotes O,
Het$^4$ denotes pyridyl which is unsubstituted or monosubstituted by CONHA, or benzo-1,2,5-thiadiazol-5-yl.

15. A compound according to claim 1 in which
$R^4$ denotes —(CH$_2$)$_s$—(Ar$^1$)$_n$—Y—R$^6$,
s denotes 0 or 1,
n denotes 0 or 1,
Y denotes O or (CH$_2$)$_q$,
q denotes 0,
$R^6$ denotes Het$^4$,
Het$^4$ denotes pyridyl, benzo-1,2,5-thiadiazol-5-yl, thiazole, 1,2,3-triazole, thienyl or furyl, each of which is unsubstituted or monosubstituted by CONHA, A and/or Ar$^2$,
Ar$^2$ denotes phenyl which is unsubstituted or mono-, di- or trisubstituted by A,
Ar$^1$ denotes phenylene.

16. A compound according to claim 1 in which
Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —(CH$_2$)$_t$—OH or —(CH$_2$)$_p$-Het$^1$,
Het$^1$ denotes an unsubstituted monocyclic saturated or aromatic heterocycle having 1 to 3 N and/or O atoms,
or

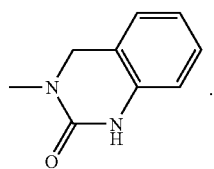

17. A compound according to claim 1 in which
Het denotes piperazinyl, piperidinyl, morpholinyl, pyrrolidinyl, pyridyl or furyl, which are unsubstituted or may be mono-, di- or trisubstituted by Hal, A, NHA, NA$_2$, COOA, benzyl, —(CH$_2$)$_t$—OH or —(CH$_2$)$_p$-Het$^1$,
Het$^1$ denotes morpholinyl, pyrrolidinyl, pyridyl
or

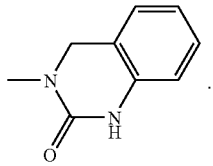

18. A compound according to claim 1 in which
$R^4$ denotes —(CH$_2$)$_s$—(Ar$^1$)$_n$—Y—R$^6$,
s denotes 0 or 1,
n denotes 0 or 1,
Y denotes O, (CH$_2$)$_q$ or NH,
Ar$^1$ denotes phenylene,
q denotes 0,1,2,3 or 4,
$R^6$ denotes Het$^4$, —(CH$_2$)$_r$—NH$_2$, —(CH$_2$)$_r$—NHA or —(CH$_2$)$_r$—NA$_2$,
r denotes 0,1,2,3or 4,
Het$^4$ denotes pyridyl, benzo-1,2,5-thiadiazol-5-yl, thiazole, 1,2,3-triazole, thienyl or furyl, each of which is unsubstituted or monosubstituted by CONHA, A or Ar$^2$,
Ar$^2$ denotes phenyl which is unsubstituted or mono-, di- or trisubstituted by A.

19. A compound according to claim 1 in which
$R^1$ denotes A, —(CH$_2$)$_m$—Ar,
m denotes 0,
Ar denotes phenyl which is unsubstituted or mono-, di- or trisubstituted by Hal, A, OA, COOH or COOA,
$R^2$ denotes CN,
$R^3$ denotes H, A, —S-A, phenyl or —(CH$_2$)$_p$-Het,
Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —(CH$_2$)$_t$—OH or —(CH$_2$)$_p$-Het$^1$,
Het$^1$ denotes an unsubstituted monocyclic saturated or aromatic heterocycle having 1 to 2 N and/or O atoms,
or

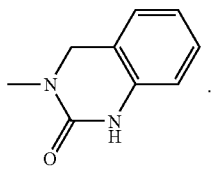

20. A compound according to claim 1 in which
$R^4$ denotes —(CH$_2$)$_s$—(Ar$^1$)$_n$—Y—R$^6$,
s denotes 0, 1, 2, 3 or 4,
n denotes 0 or 1,
Y denotes O or (CH$_2$)$_q$,
Ar$^1$ denotes phenylene,
q denotes 0,
$R^6$ denotes Het$^4$,—(CH$_2$)$_r$—NH$_2$, —(CH$_2$)$_r$—NHA or —(CH$_2$)$_r$—NA$_2$,
r denotes 0, 1, 2, 3 or 4,-

Het⁴ denotes a monocyclic saturated or aromatic heterocycle having 1 to 3 N, O and/or S atoms, which may be unsubstituted or mono-, di- or trisubstituted by A, CONH₂, CONHA, CONA₂ or Ar², Ar² denotes phenyl which is unsubstituted or mono-, di- or trisubstituted by A.

21. A compound according to claim 1 in which
Het⁴ denotes pyridyl, benzo-1,2,5-thiadiazol-5-yl, piperazine, thiazole or imidazole, each of which is unsubstituted or monosubstituted by CONHA, A or Ar².

22. A compound according to claim 1 in which
R⁴ denotes 4-(pyridin-4-yloxy)phenyl, 4-(pyridin-4-yloxy)-phenylmethyl or 4-(benzo-1,2,5-thiadiazol-5-yloxy)phenyl, where the pyridine radical may be substituted by CONHCH₃.

23. A compound according to claim 1 in which Het¹ denotes an unsubstituted monocyclic saturated or aromatic heterocycle having 1 to 2 N and/or O atoms,
or

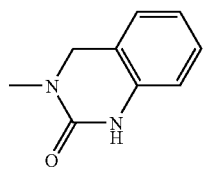

24. A compound according to claim 1 in which
Het¹ denotes morpholinyl, pyrrolidinyl, piperidinyl, pyridyl
or

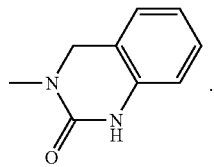

25. A compound according to claim 1 in which
Het² denotes an unsubstituted monocyclic aromatic heterocycle having 1-2 N, O and/or S atoms.

26. A compound according to claim 1 in which
R¹ denotes A, —(CH₂)ₘ—Ar or —(CH₂)ₘ-Het²,
m denotes 0,
Ar denotes phenyl which is unsubstituted or mono-, di- or trisubstituted by Hal, A, OA, COOH or COOA,
R² denotes CN,
R³ denotes H, A, —S-A, phenyl, NH-benzyl, —(CH₂)ₚ-Het, NH—(CH₂)ₚ-Het, NA₂, NH-alkylene-NA₂ or NA-alkylene-NA₂.

27. A compound according to claim 1 in which
R² denotes CN,
Ar" denotes phenyl which is unsubstituted or mono-, di- or trisubstituted by Hal or OA,
o denotes 0 or 1.

28. A compound according to claim 1 in which
R¹ denotes A, —(CH₂)ₘ—Ar' or —(CH₂)ₘ-Het²,
Ar' denotes phenyl which is unsubstituted or mono-, di- or trisubstituted by Hal, OA, A or COOA,
m denotes 0,
Het² denotes thienyl, furyl, imidazolyl, pyrrolyl, thiazolyl or pyridyl.

29. A compound according to claim 1 in which
X denotes C,
B denotes N, CH or C—CN,
R¹ denotes A, —(CH₂)ₘ—Ar' or —(CH₂)ₘ-Het²,
Ar' denotes phenyl which is unsubstituted or mono-, di- or trisubstituted by Hal, OA, A or COOA,
m denotes 0,
Het² denotes thienyl, furyl, imidazolyl, pyrrolyl, thiazolyl or pyridyl,
R² denotes CN,
Ar" denotes phenyl which is unsubstituted or mono-, di- or trisubstituted by Hal or OA,
o denotes 0 or 1,
R³ denotes H, A, —S-A, phenyl, NH-benzyl, —(CH₂)ₚ-Het, NH—(CH₂)ₚ-Het, NA₂, NH-alkylene-NA₂ or NA-alkylene-NA₂,
Het denotes piperazinyl, piperidinyl, morpholinyl, pyrrolidinyl, pyridyl or furyl, which are unsubstituted or may be mono-, di- or trisubstituted by Hal, A, NHA, NA₂, COOA, benzyl, —(CH₂)ₜ—OH or —(CH₂)ₚ-Het¹,
Het¹ denotes morpholinyl, pyrrolidinyl, pyridyl
or

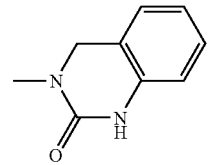

R⁴ denotes —(CH₂)ₛ—(Ar¹)ₙ—Y—R⁶,
Y denotes O or (CH₂)_q,
R⁵ denotes H or CH₃, or
R⁴ and R⁵ together denote

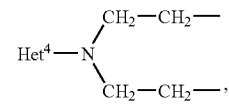

R⁶ denotes Het⁴, —(CH₂)ᵣ—NH₂, —(CH₂)ᵣ—NHA or —(CH₂)ᵣ—NA₂,
Het⁴ denotes pyridyl, benzo-1, 2, 5-thiadiazol-5-yl, piperazine, thiazole or imidazole, each of which is unsubstituted or monosubstituted by CONHA, A and/or Ar²,
Ar¹ denotes phenylene or piperazinediyl,
Ar² denotes phenyl which is unsubstituted or mono-, di- or trisubstituted by A,
R⁷, R⁸, R⁹, R¹⁰ each, independently of one another, denote H, A or —(CH₂)ₚ—Ar,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if Ar¹ denotes piperazinediyl, R⁶ may also denote H or alkyl having 1-6 C atoms.

30. A compound according to claim 1 in which
X denotes C,
B denotes N, CH or C—CN,
$R^1$ denotes A, —$(CH_2)_m$—Ar' or —$(CH_2)_m$-Het$^2$,
Ar' denotes phenyl which is unsubstituted or mono-, di- or trisubstituted by Hal, OA, A or COOA,
m denotes 0,
Het$^2$ denotes an unsubstituted monocyclic aromatic heterocycle having 1-2 N, O and/or S atoms,
$R^2$ denotes CN,
Ar'' denotes phenyl which is unsubstituted or mono-, di- or trisubstituted by Hal or OA,
o denotes 0 or 1,
$R^3$ denotes H, A, —S-A, phenyl, NH-benzyl, —$(CH_2)_p$-Het, NH—$(CH_2)_p$-Het, NA$_2$, NH-alkylene-NA$_2$ or NA-alkylene-NA$_2$,
Het denotes a monocyclic saturated or aromatic heterocycle having 1 to 3 N and/or O atoms, which may be unsubstituted or mono-, di- or trisubstituted by Hal, A, NHA, NA$_2$, COOA, benzyl, —$(CH_2)_t$—OH or —$(CH_2)_p$-Het$^1$,
Het$^1$ denotes morpholinyl, pyrrolidinyl, pyridyl or

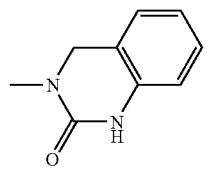

$R^4$ denotes —$(CH_2)_s$—$(Ar^1)_n$—Y—$R^6$,
Y denotes O or $(CH_2)_q$,
$R^5$ denotes H or CH$_3$, or
$R^4$ and $R^5$ together denote

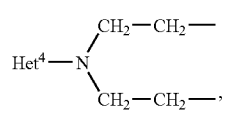

$R^6$ denotes Het$^4$, —$(CH_2)_r$—NH$_2$, —$(CH_2)_r$—NHA or —$(CH_2)_r$—NA$_2$,
Het$^4$ denotes a monocyclic saturated or aromatic heterocycle having 1 to 3 N, O and/or S atoms, which may be unsubstituted or mono-, di- or trisubstituted by A, CONH$_2$, CONHA, CONA$_2$ or Ar$^2$,
Ar$^1$ denotes phenylene or piperazinediyl,
Ar$^2$ denotes phenyl which is unsubstituted or mono-, di- or trisubstituted by A,
$R^7$, $R^8$, $R^9$, $R^{10}$ each, independently of one another, denote H, A or —$(CH_2)_p$—Ar,
A denotes alkyl having 1 to 10 C atoms, where, in addition, 1-7 H atoms may be replaced by F and/or chlorine,
n denotes 0 or 1,
p denotes 0, 1, 2, 3 or 4,
q denotes 0, 1, 2, 3 or 4,
r denotes 0, 1, 2, 3 or 4,
s denotes 0, 1, 2, 3 or 4,
t denotes 1, 2, 3 or 4,
Hal denotes F, Cl, Br or I,
and, if Ar$^1$ denotes piperazinediyl, $R^6$ may also denote H or alkyl having 1-6 C atoms.

31. A compound, which is

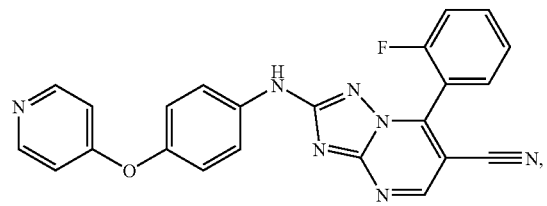

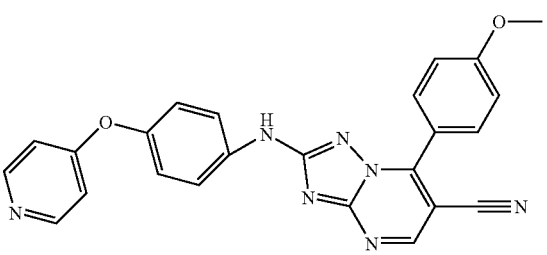

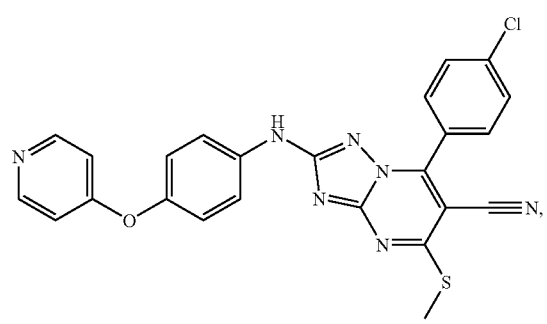

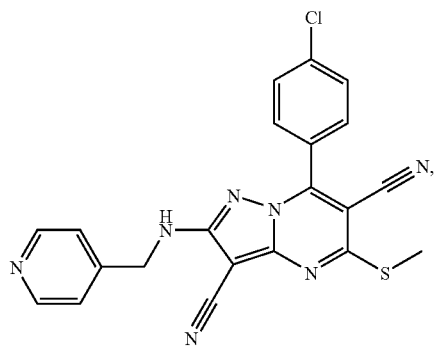

-continued
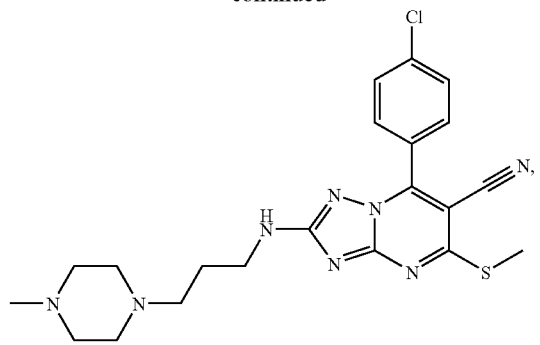
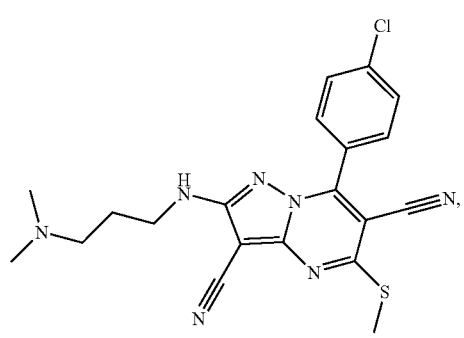
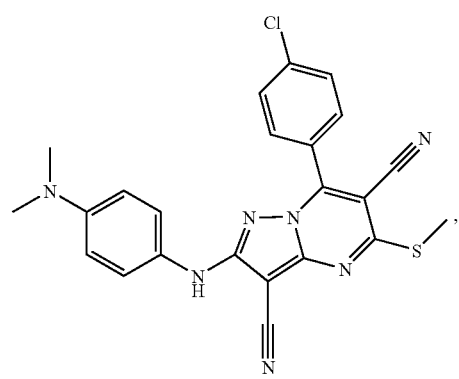
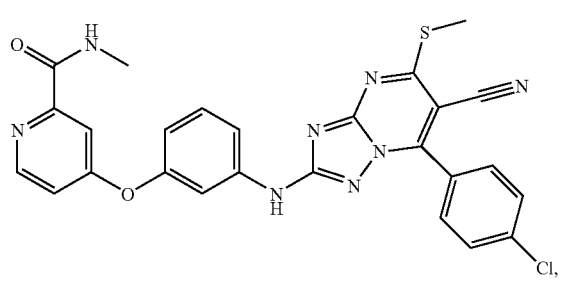
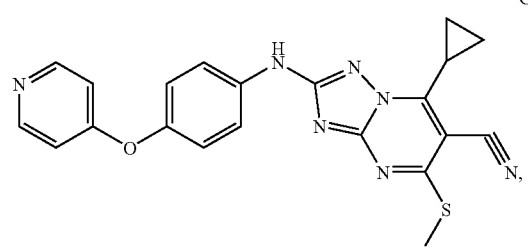
-continued
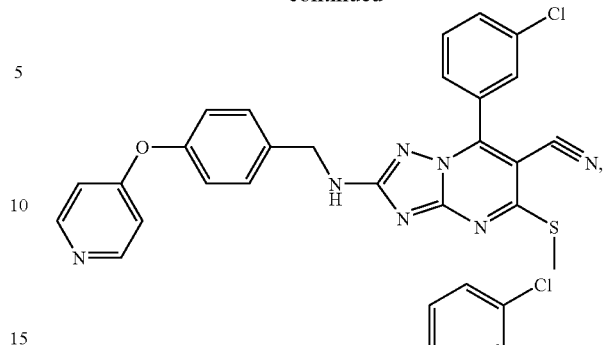
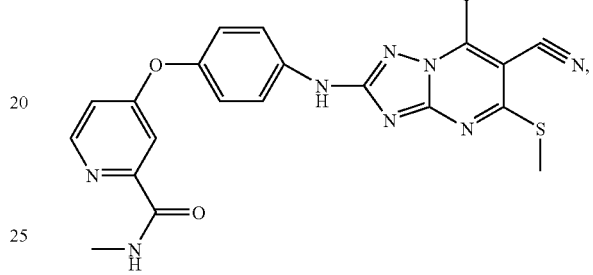
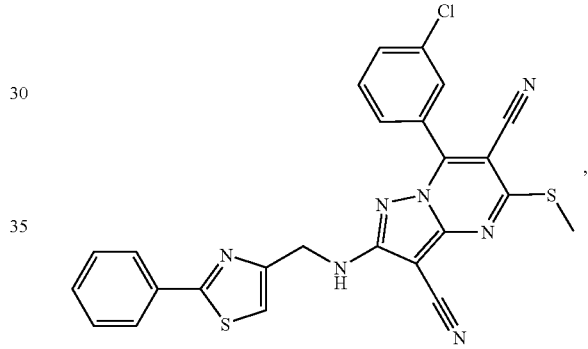
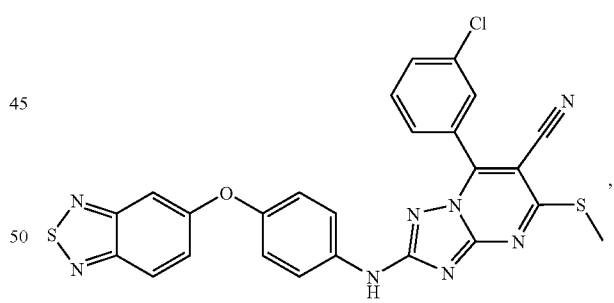
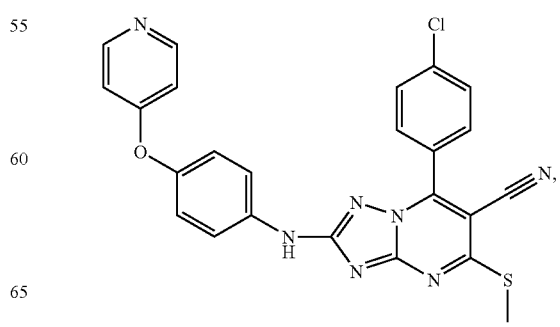

-continued
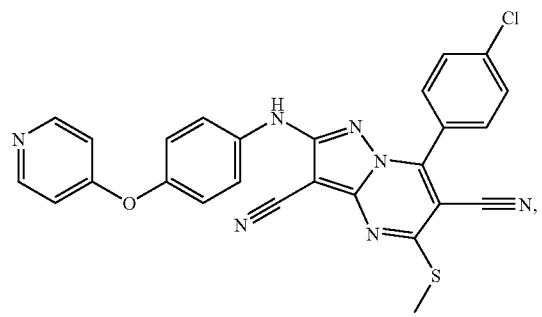
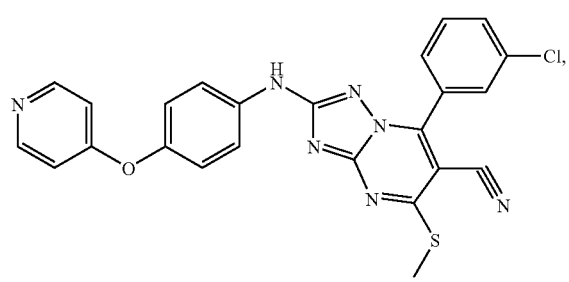
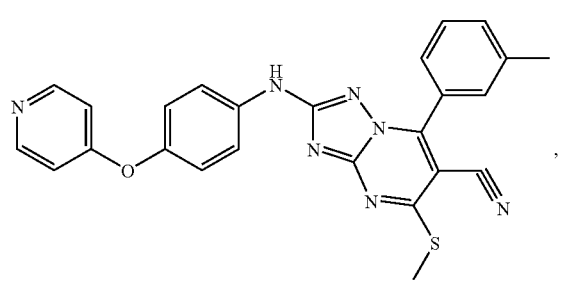
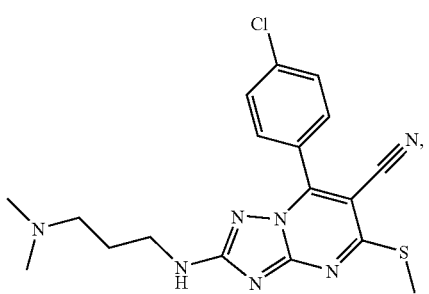
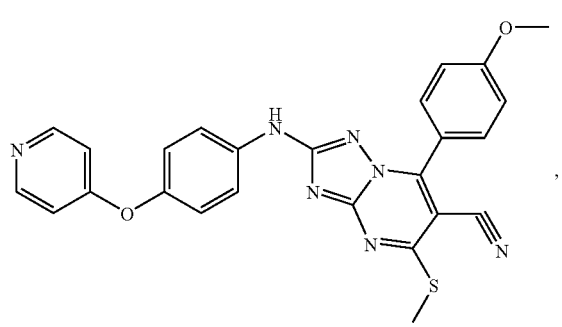
-continued
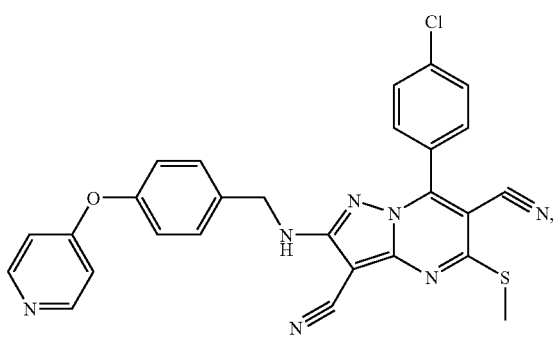
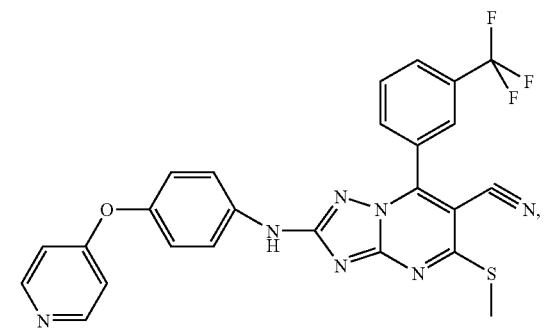
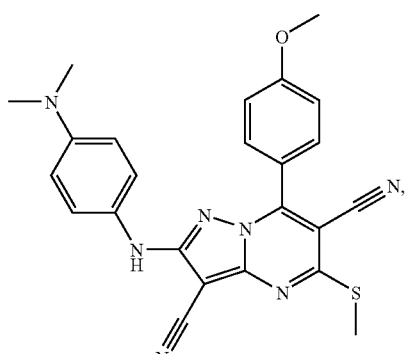
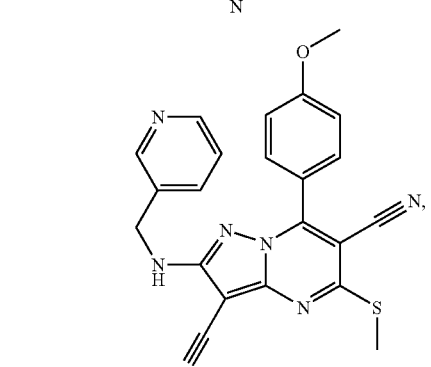
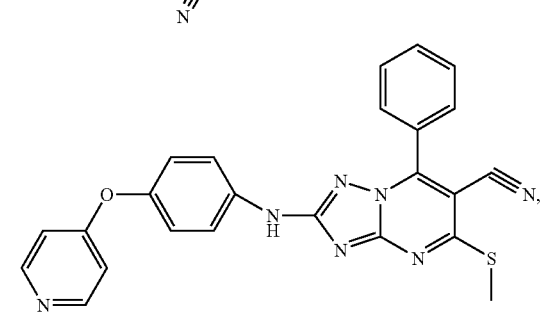

-continued
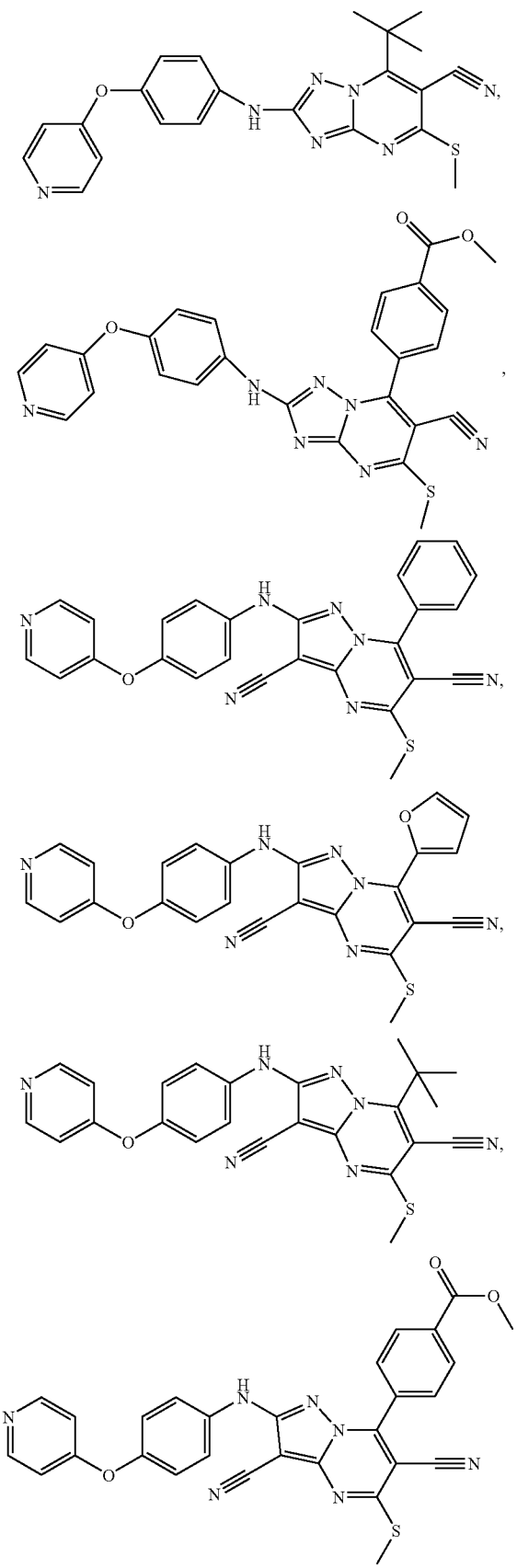
-continued
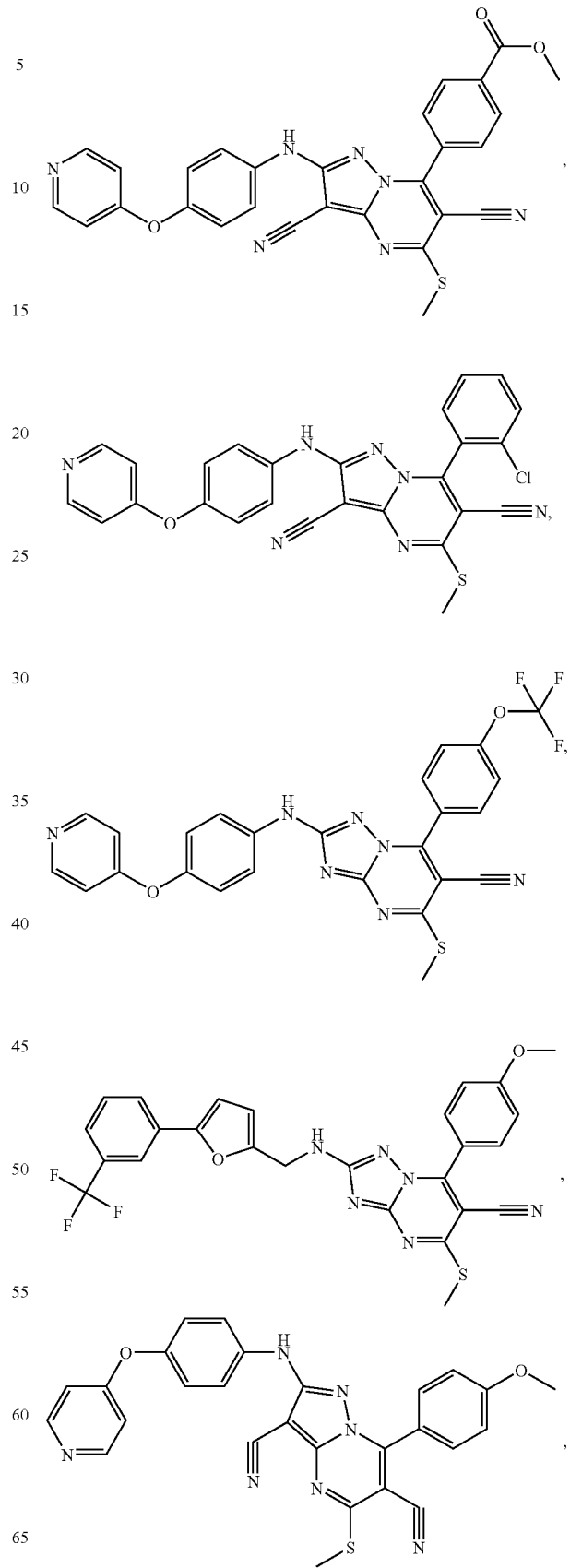

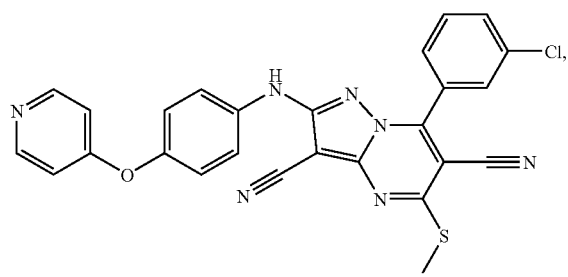
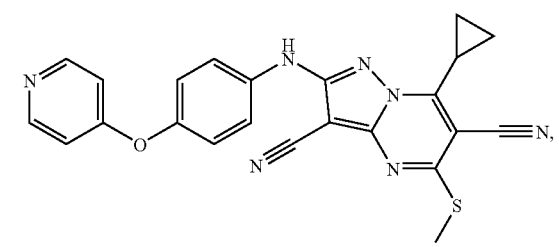
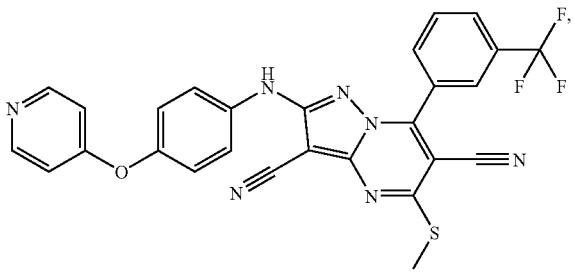
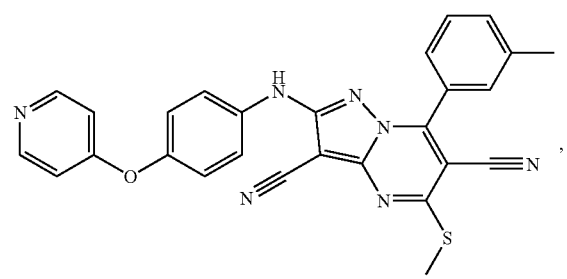
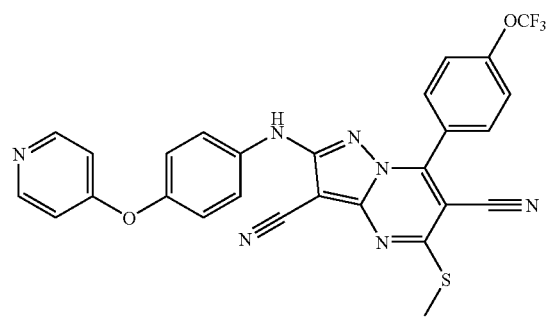
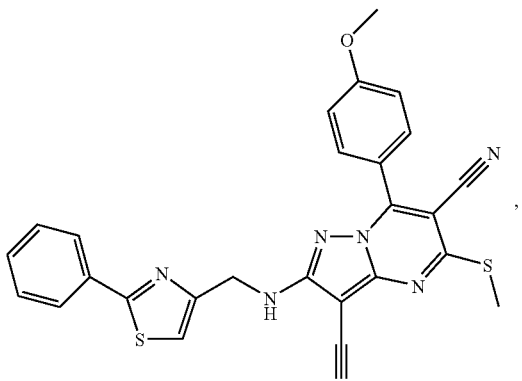
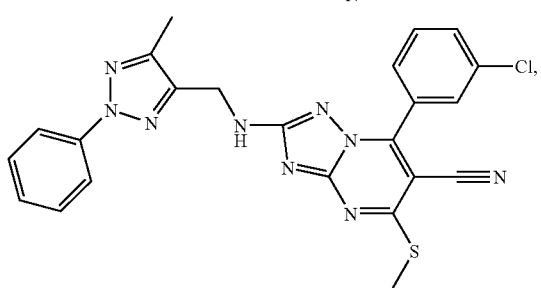
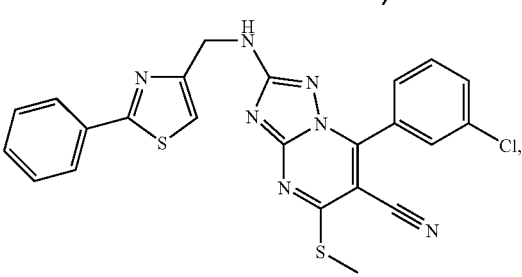
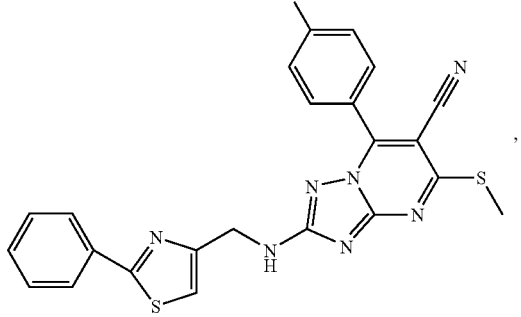
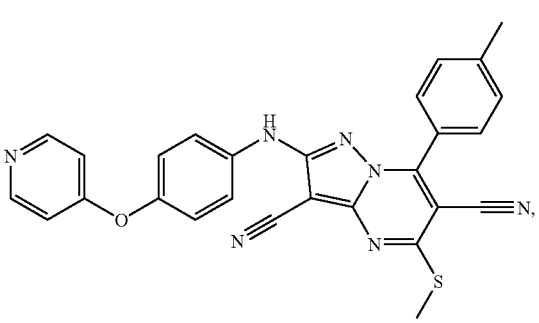

-continued
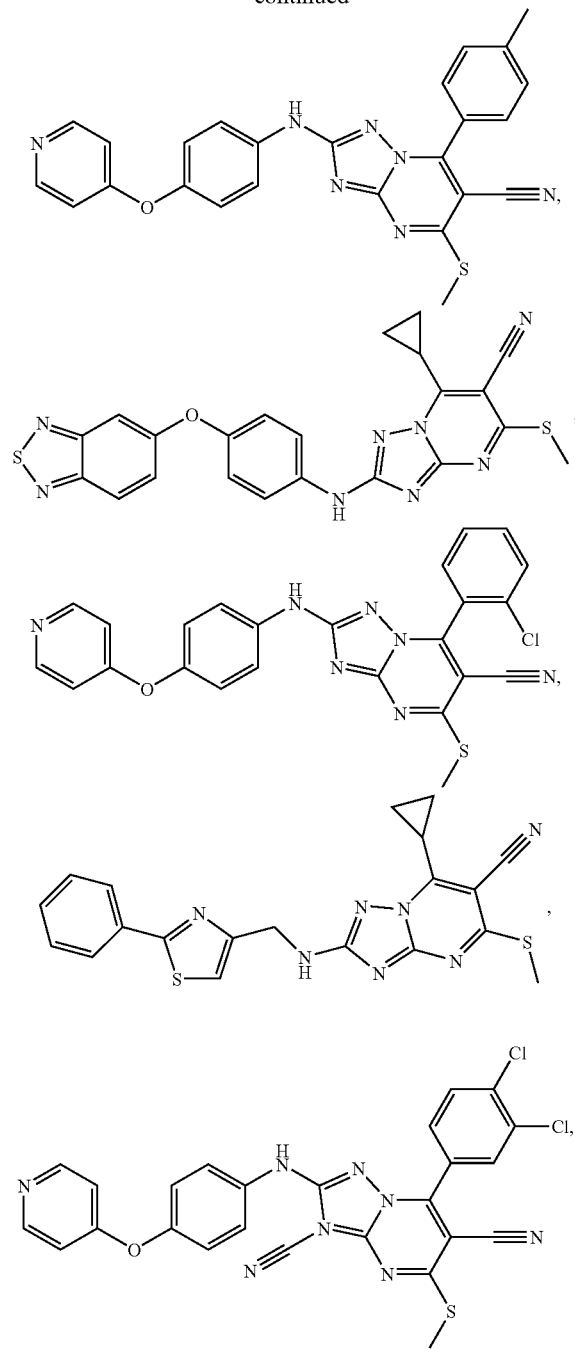
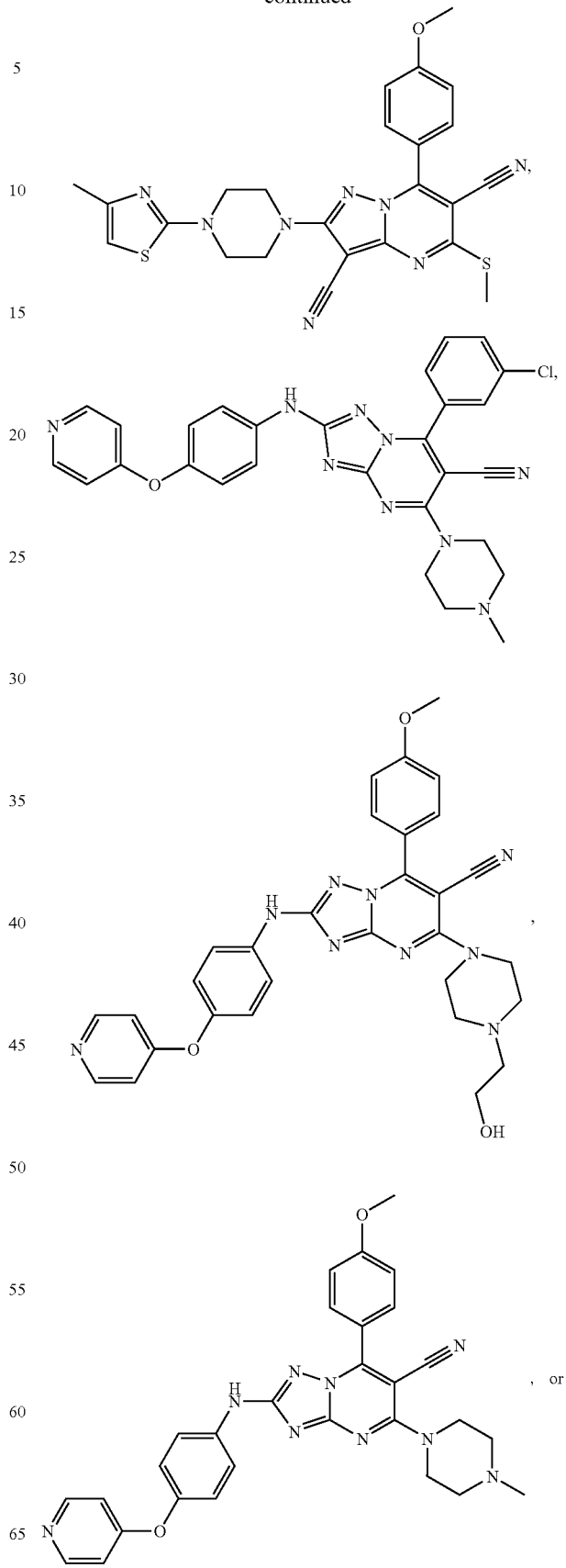

-continued

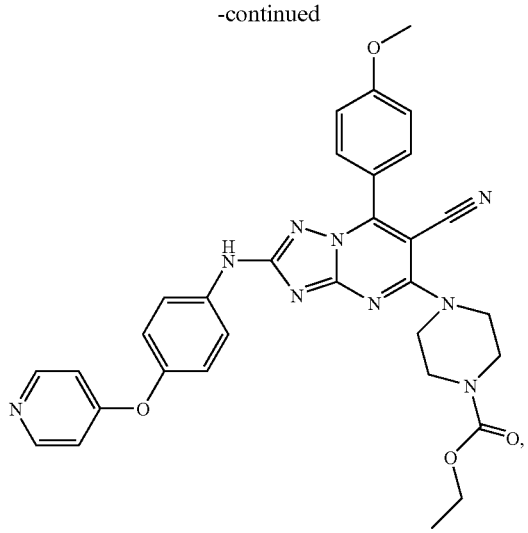

or a pharmaceutically acceptable tautomer, salt or stereoisomer thereof.

32. A process for preparing a compound according to claim 1 or a pharmaceutically acceptable tautomer, salt or stereoisomer thereof, comprising
a) for the preparation of compounds of the formula I in which X denotes C, reacting a compound of formula II

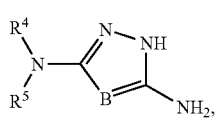

in which $R^4$, $R^5$ and B have the meanings indicated for the compound of formula I,
i) with a compound of formula IIIa

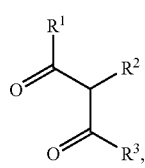

in which $R^1$ OA and $R^2$ and $R^3$ have the meanings indicated for the compound of formula I,
or
ii) with a compound of formula IIIb

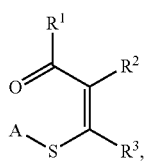

in which $R^1$, $R^2$ and $R^3$ have the meanings indicated for the compound of formula I,
and A denotes alkyl having 1, 2, 3 or 4 C atoms,
or
iii) with a compound of formula IIIc

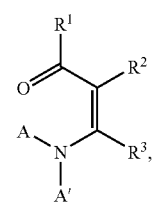

in which
$R^1$, besides the meanings indicated for the compound of formula I, also denotes OA,
$R^2$ and $R^3$ have the meanings indicated for the compound of formula I, and A, A' each, independently of one another, denote alkyl having 1, 2, 3 or 4 C atoms, or A and A' together form a butylene or pentylene chain,
and/or
a base or acid of a compound of formula I is converted into one of its salts.

33. A pharmaceutical composition comprising a compound according to claim 1 and a pharmaceutically acceptable carrier.

34. A process according to claim 32, wherein one or more radical(s) $R^1$, $R^2$ and/or $R^3$ in a compound of formula I is (are) converted into one or more other radical(s) $R^1$, $R^2$ and/or $R^3$, by
i) converting an alkylsulfanyl group into an amine,
ii) hydrolysing an ester to the acid, reducing it to the aldehyde or alcohol, or
iii) reducing a nitrite to the aldehyde or amine.

35. A pharmaceutical composition comprising a compound according to claim 31 and a pharmaceutically acceptable carrier.

36. A compound of formula I according to claim 1,
in which
X denotes C,
B denotes N, CH or C—CN,
$R^1$ denotes A, —$(CH_2)_m$—Ar or —$(CH_2)_m$-Het$^2$,
$R^2$ denotes CN,
$R^3$ denotes H, A, —S-A, —$(CH_2)_p$—Ar, —$(CH_2)_p$-Het, NH—$(CH_2)_p$—Ar, NH—$(CH_2)_p$-Het, NH$_2$, NHA, NA$_2$, NH-alkylene-NH$_2$, NH-alkylene-NHA, NH-alkylene-NA$_2$ or NA-alkylene-NA$_2$,
$R^4$ denotes —$(CH_2)_s$—$(Ar^1)_n$—Y—$R^6$,
$R^5$ denotes H or CH$_3$, or
$R^4$ and $R^5$ together denote

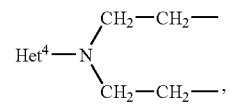

$R^6$ denotes Het$^4$, —$(CH_2)_r$—NH$_2$, —$(CH_2)_r$—NHA or —$(CH_2)_r$—NA$_2$,
Y denotes O, S, $(CH_2)_q$ or NH,
Ar denotes phenyl, naphthyl or biphenyl, each of which is unsubstituted or mono-, di- or trisubstituted by Hal, A, OH, OA, NH$_2$, NO$_2$, CN, COOH, COOA, CONH$_2$, NHCOA, NHCONH$_2$, NHSO$_2$A, CHO, COA, SO$_2$NH$_2$, SO$_2$A, —CH$_2$—COOH or —OCH$_2$—COOH, Ar¹ denotes phenylene or piperazinediyl, Het denotes a mono- or bicyclic saturated, unsaturated or aromatic heterocycle having 1 to 4 N, O and/or S atoms, which may be unsubstituted or mono-, di- or trisubstituted by Hal, A, NHA, NA$_2$, OA, COOA, CN, —(CH$_2$)$_p$—Ar, —(CH$_2$)$_t$—OH, —(CH$_2$)$_p$-Het¹ or carbonyl oxygen (=O), Het¹ denotes a mono- or bicyclic saturated, unsaturated or aromatic heterocycle having 1 to 4 N, O and/or S atoms, which may be unsubstituted or mono- or disubstituted by A or carbonyl oxygen (=O), Het² denotes a monocyclic aromatic heterocycle having 1 to 3 N, O and/or S atoms, which may be unsubstituted or mono- or disubstituted by A, Het³ denotes a monocyclic saturated or aromatic heterocycle having 1 to 3 N, O and/or S atoms, which may be unsubstituted or mono- or disubstituted by A, Het⁴ denotes a mono- or bicyclic saturated, unsaturated or aromatic heterocycle having 1 to 4 N, O and/or S atoms, which may be unsubstituted or mono-, di- or trisubstituted by Hal, A, CONH$_2$, CONHA, CONA$_2$ or Ar², Ar² denotes phenyl which is unsubstituted or mono-, di- or trisubstituted by Hal, A, OH, OA, NH$_2$, NO$_2$, CN, COOH, COOA, CONH$_2$, NHCOA, NHCONH$_2$, NHSO$_2$A, CHO, COA, SO$_2$NH$_2$ or SO$_2$A, R⁷, R⁸, R⁹, R¹⁰ each, independently of one another, denote H, A or —(CH$_2$)$_p$—Ar, A denotes alkyl having 1 to 10 C atoms, where, in addition, 1-7 H atoms may be replaced by F and/or chlorine, m denotes 0, 1, 2, 3 or 4, n denotes 0 or 1, p denotes 0, 1, 2, 3 or 4, q denotes 0, 1, 2, 3 or 4, r denotes 0, 1, 2, 3 or 4, s denotes 0, 1, 2, 3 or 4, Hal denotes F, Cl, Br or I, and, if Ar¹ denotes piperazinediyl, R⁶ may also denote H or alkyl having 1-6 C atoms, or a pharmaceutically acceptable salt thereof.

37. A pharmaceutical composition comprising a compound according to claim 36 and a pharmaceutically acceptable carrier.

38. A compound according to claim 31, which is

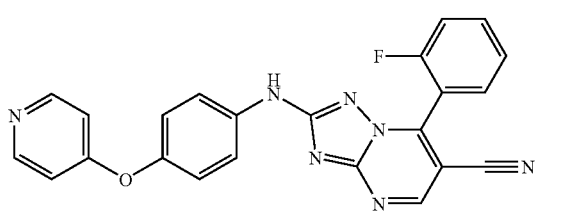

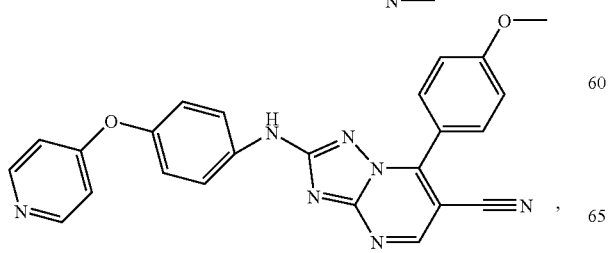

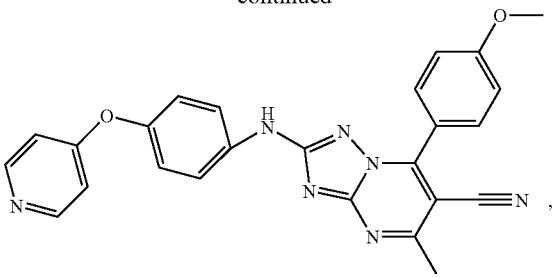

-continued

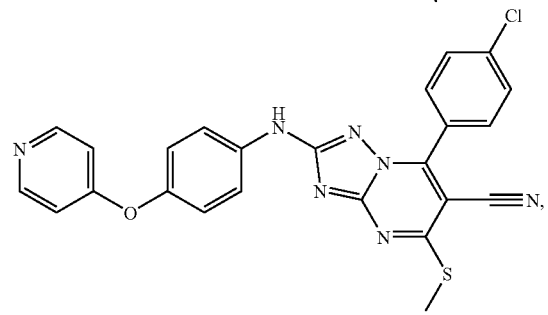

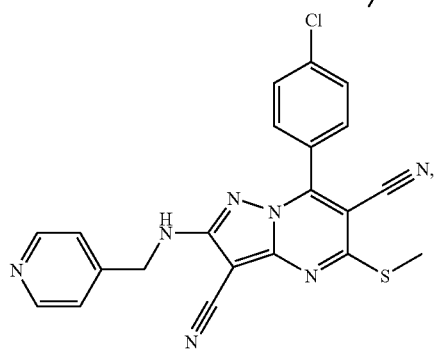

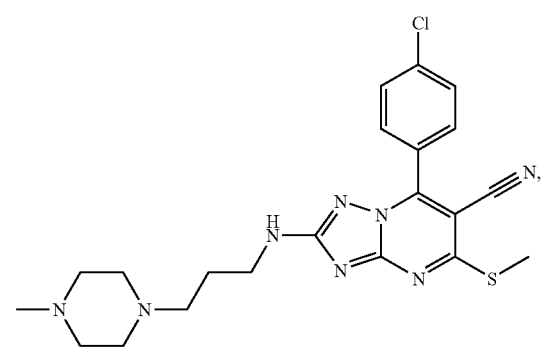

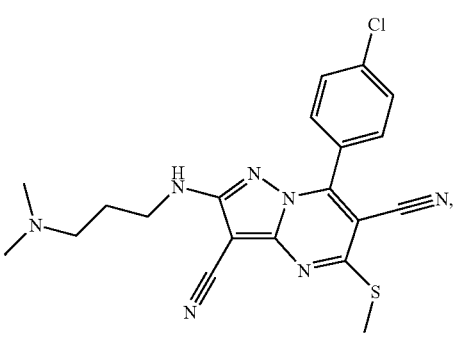

171 172
-continued -continued
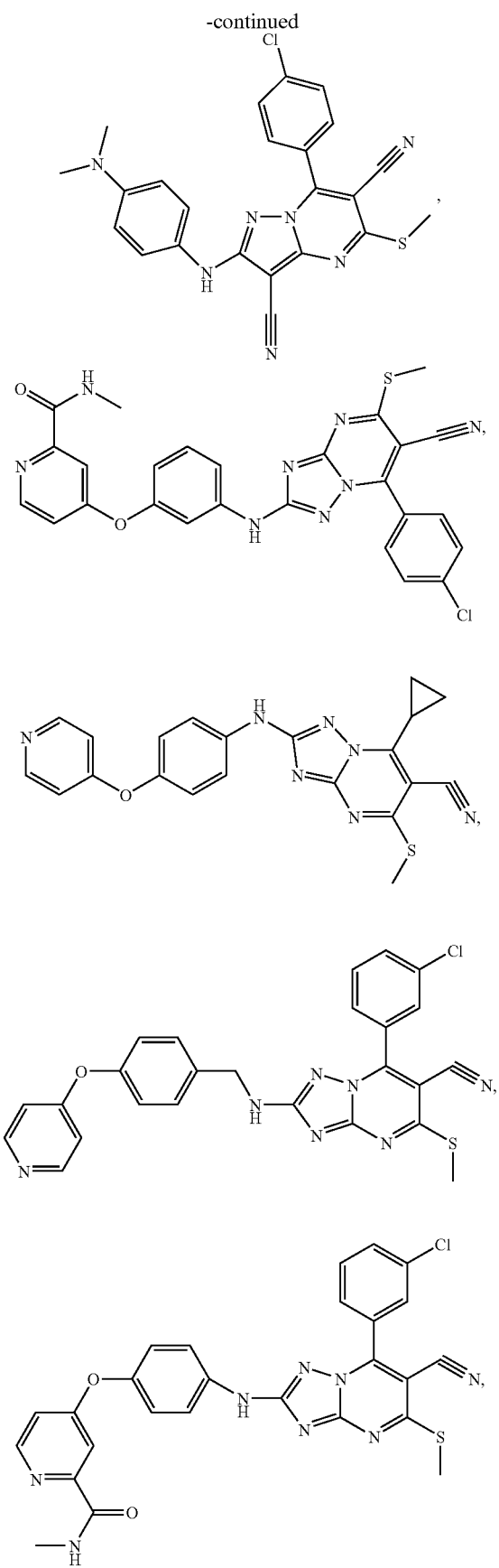
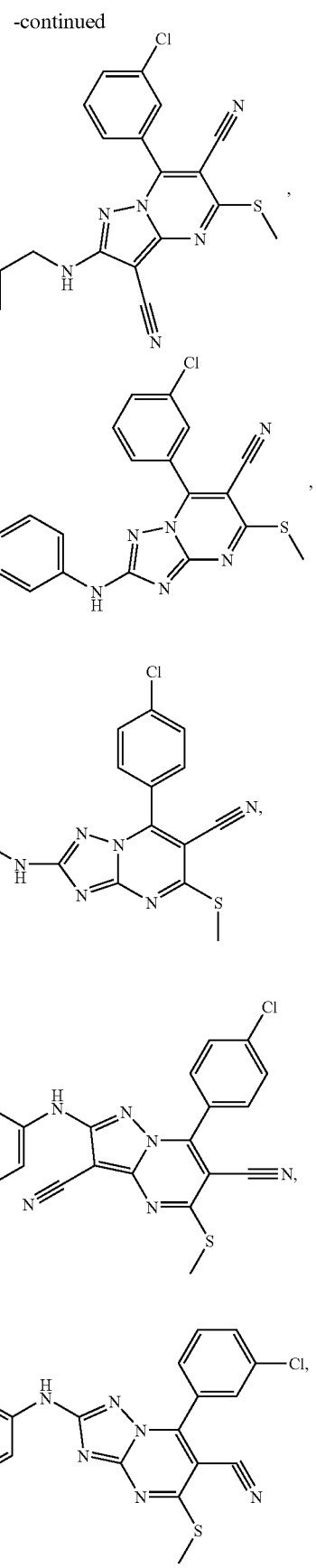

-continued
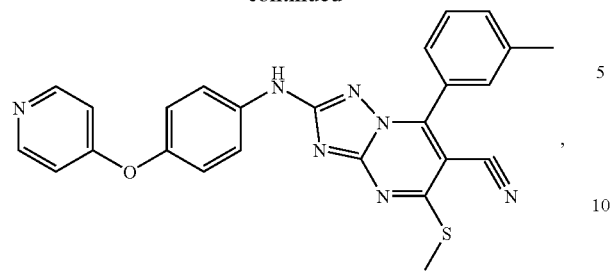
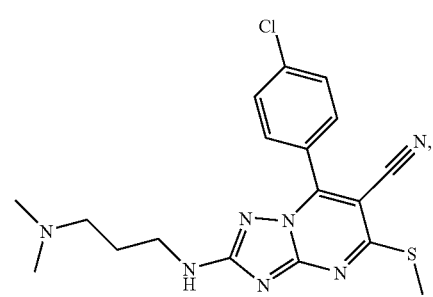
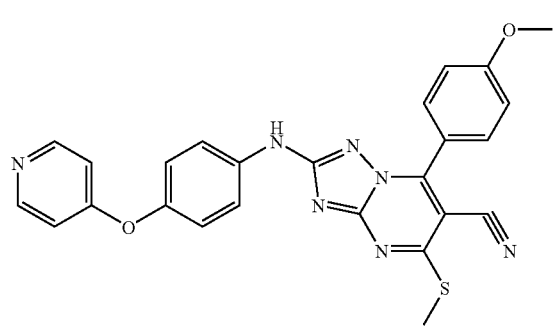
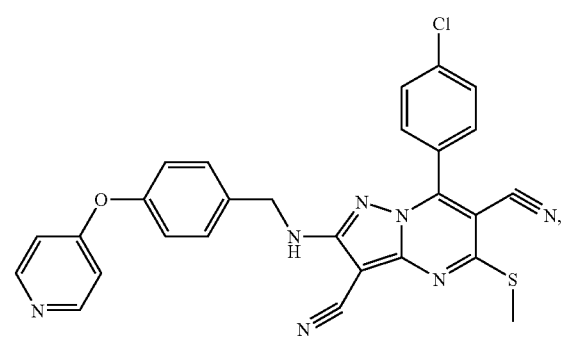
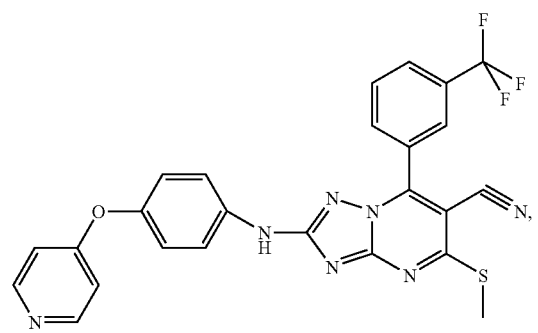
-continued
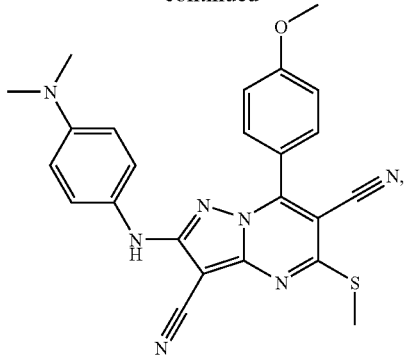
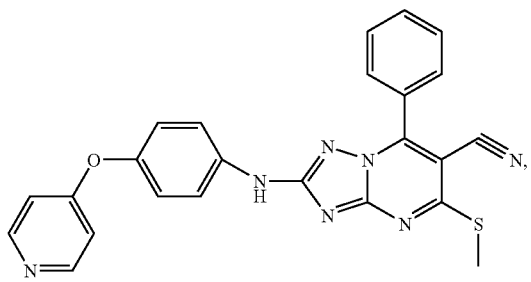
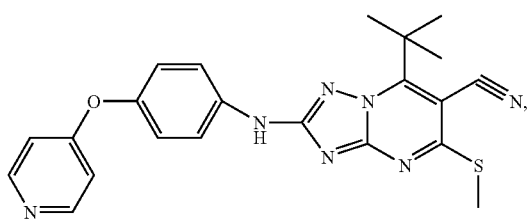
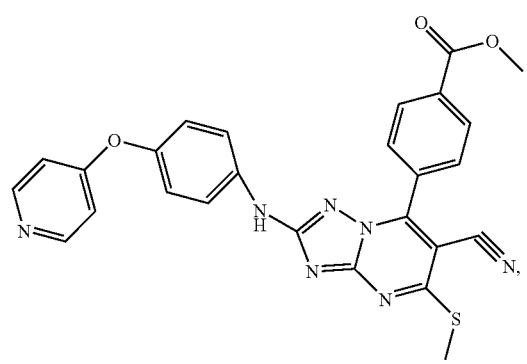

175
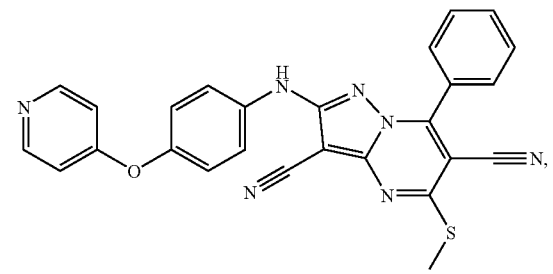
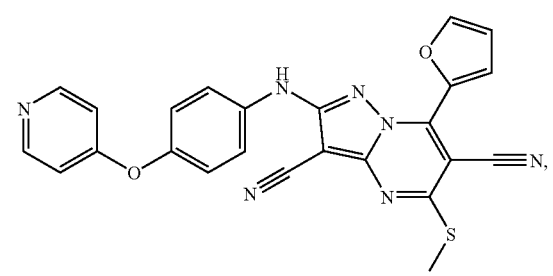
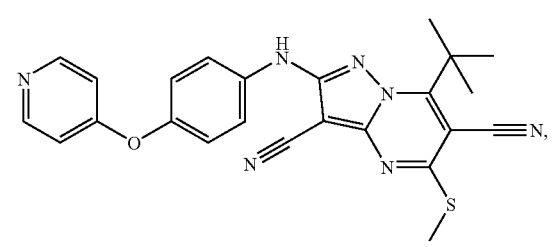
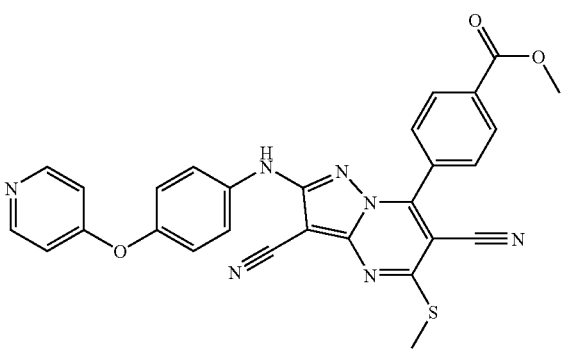
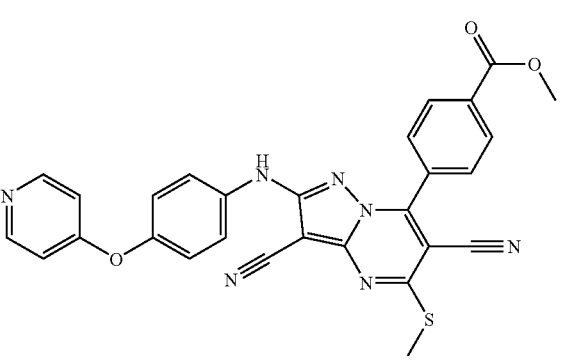
176
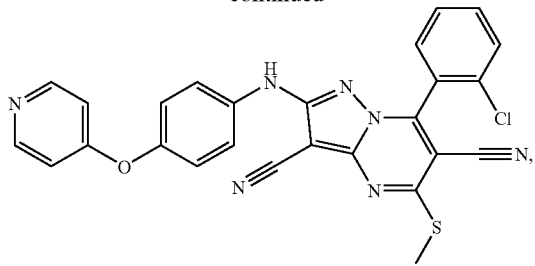
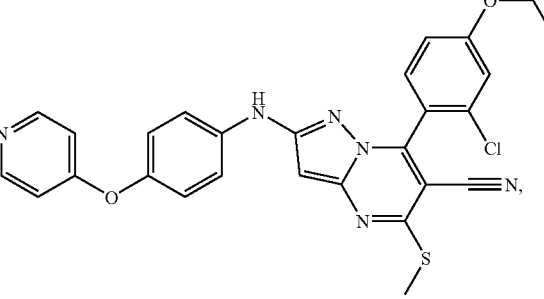
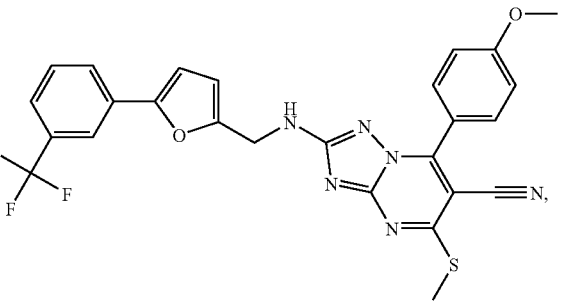
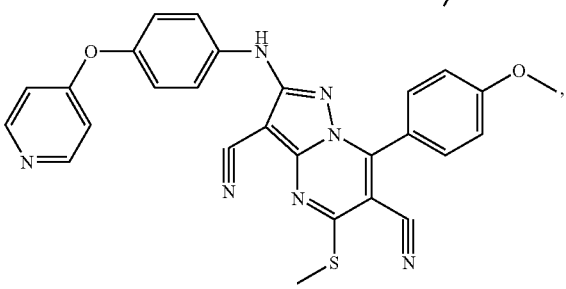
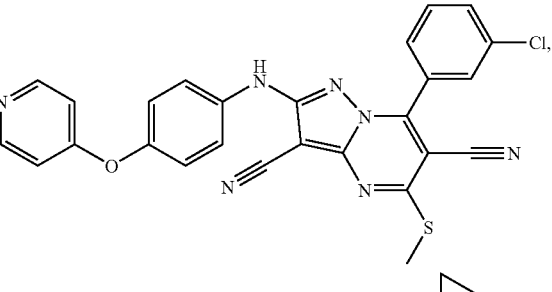
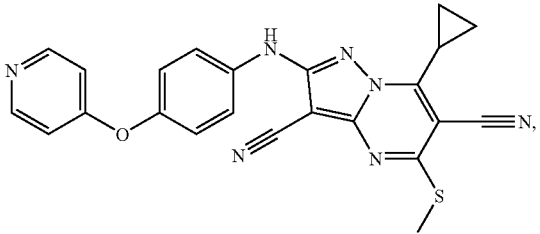

-continued
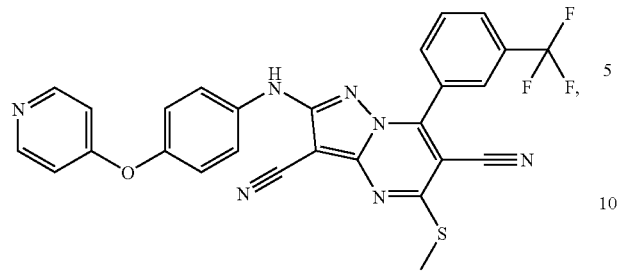
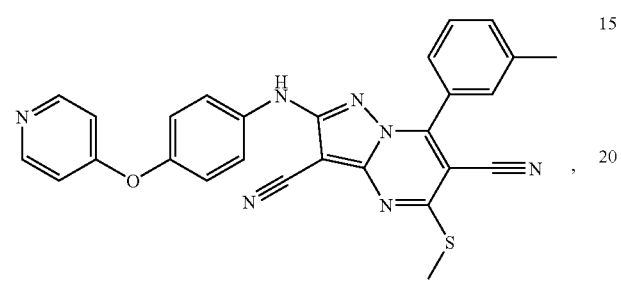
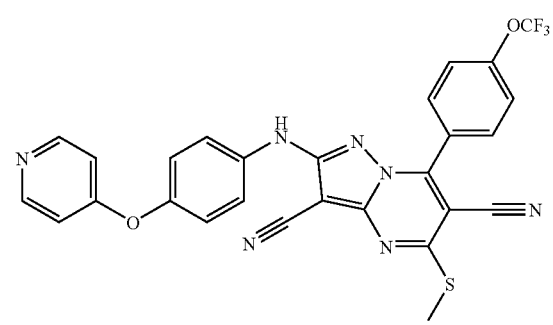
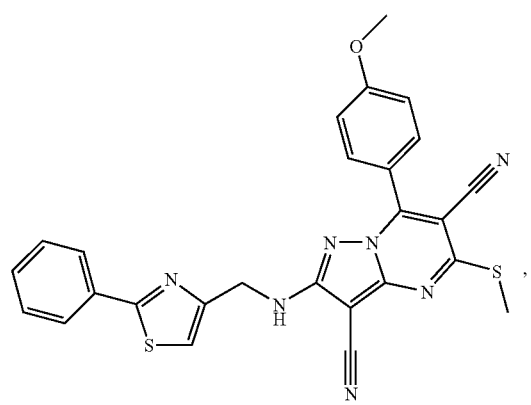
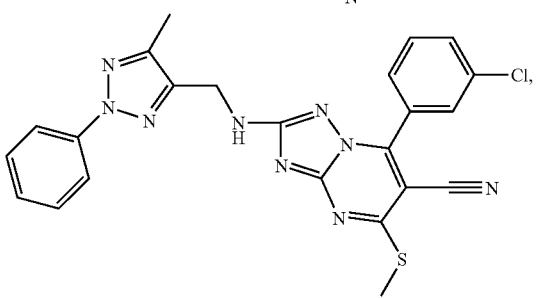
-continued
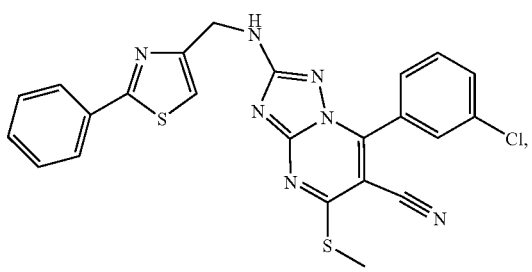
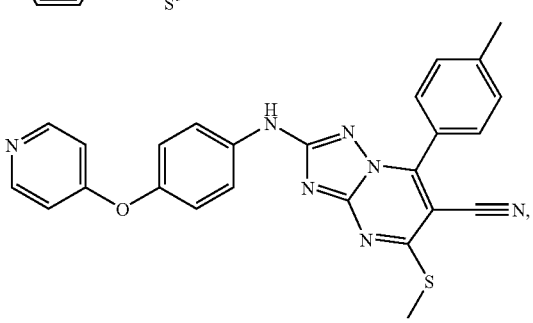
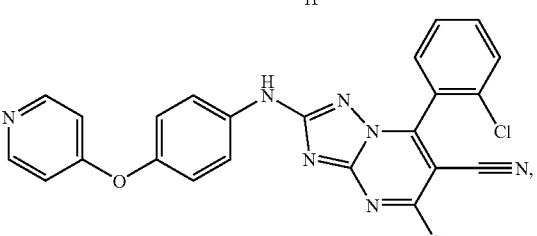

-continued

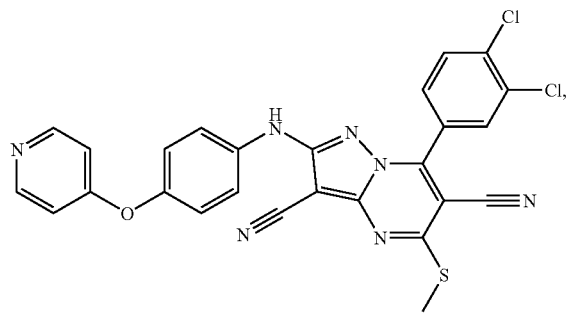

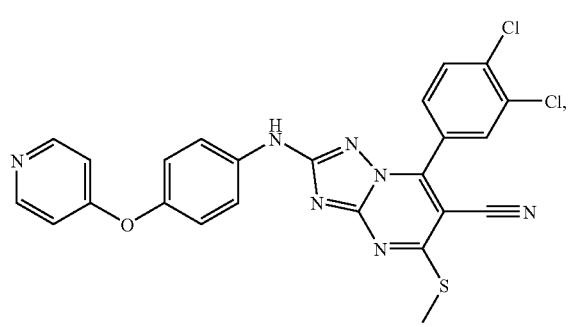

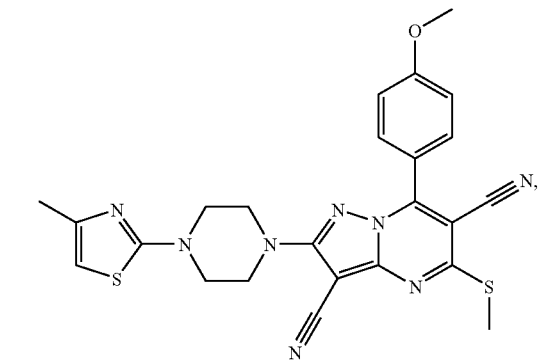

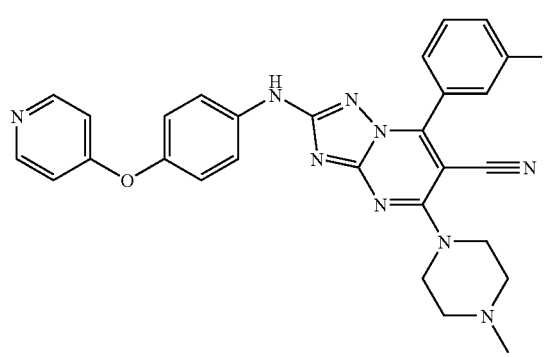

-continued

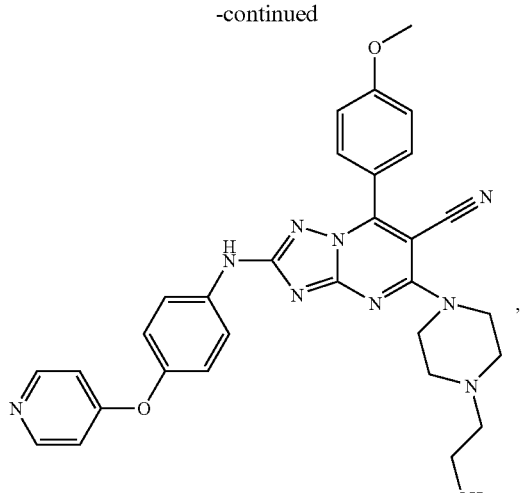

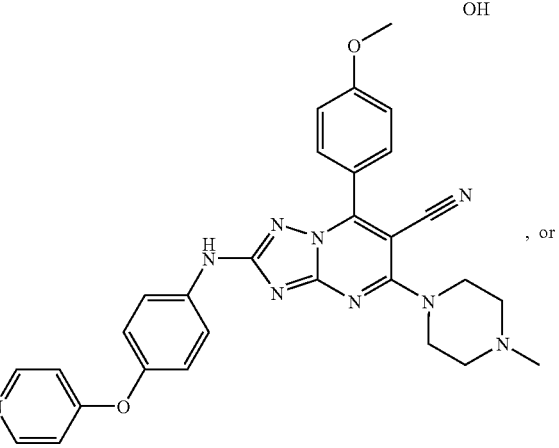, or

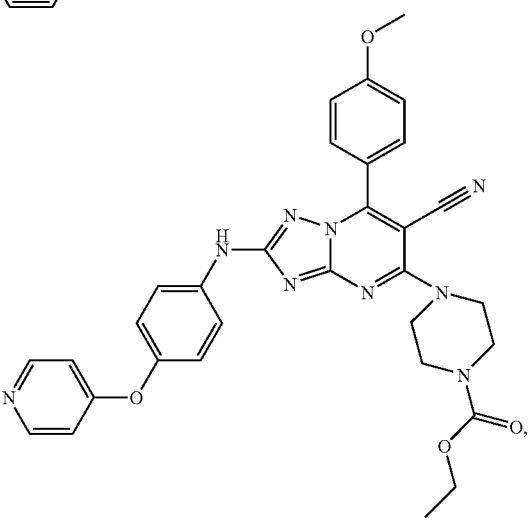

or a pharmaceutically acceptable salt thereof.

39. A pharmaceutical composition comprising a compound according to claim 38 and a pharmaceutically acceptable carrier.

40. A pharmaceutical composition comprising a compound according to claim 2 and a pharmaceutically acceptable carrier.

41. A pharmaceutical composition comprising a compound according to claim 29 and a pharmaceutically acceptable carrier.

42. A pharmaceutical composition comprising a compound according to claim 30 and a pharmaceutically acceptable carrier.

43. A compound according to claim 1, in which $R^1$ denotes A.

44. A compound according to claim 1, in which $R^1$ denotes $-(CH_2)_m-Ar$.

45. A compound according to claim 1, in which $R^1$ denotes $-(CH_2)_m\text{-Het}^2$.

46. A compound according to claim 1, in which B denotes N.

47. A compound according to claim 1, in which B denotes C—CN.

* * * * *

UNITED STATES PATENT AND TRADEMARK OFFICE
CERTIFICATE OF CORRECTION

PATENT NO. : 7,816,365 B2
APPLICATION NO. : 10/581499
DATED : October 19, 2010
INVENTOR(S) : Kai Schiemann Page 1 of 1

It is certified that error appears in the above-identified patent and that said Letters Patent is hereby corrected as shown below:

Column 176, line 14-24 read:

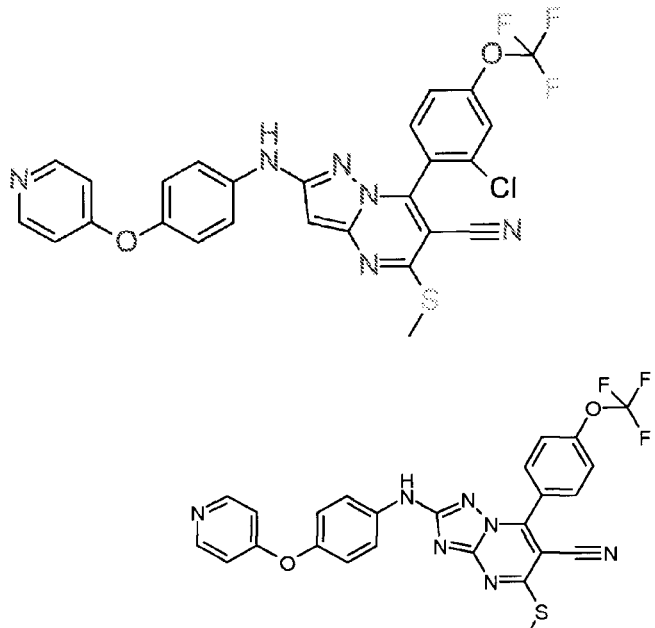

Should read: --                                                                 --

Column 178, line 27 reads: (MISSING FORMULA)

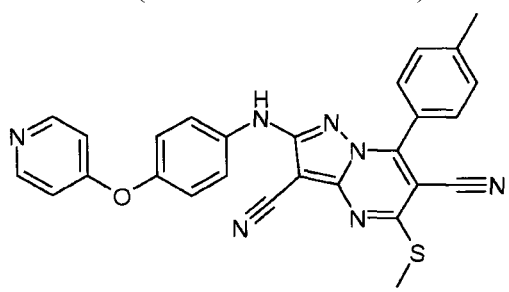

Should read: --                                                                 --

Signed and Sealed this
Eighth Day of May, 2012

David J. Kappos
*Director of the United States Patent and Trademark Office*